US010421729B2

(12) United States Patent
Wilson et al.

(10) Patent No.: US 10,421,729 B2
(45) Date of Patent: Sep. 24, 2019

(54) MICROCRYSTALLINE DIKETOPIPERAZINE COMPOSITIONS AND METHODS

(71) Applicant: MannKind Corporation, Valencia, CA (US)

(72) Inventors: Bryan R. Wilson, Brewster, NY (US); Joseph J. Guarneri, Stamford, CT (US); Marshall L. Grant, Newtown, CT (US)

(73) Assignee: MannKind Corporation, Westlake Village, CA (US)

( * ) Notice: Subject to any disclaimer, the term of this patent is extended or adjusted under 35 U.S.C. 154(b) by 383 days.

(21) Appl. No.: 14/774,311

(22) PCT Filed: Mar. 14, 2014

(86) PCT No.: PCT/US2014/029491
§ 371 (c)(1),
(2) Date: Sep. 10, 2015

(87) PCT Pub. No.: WO2014/144895
PCT Pub. Date: Sep. 18, 2014

(65) Prior Publication Data

US 2016/0031833 A1 Feb. 4, 2016

Related U.S. Application Data

(60) Provisional application No. 61/800,520, filed on Mar. 15, 2013.

(51) Int. Cl.
*C07D 241/08* (2006.01)
*B01D 1/18* (2006.01)
(Continued)

(52) U.S. Cl.
CPC .............. *C07D 241/08* (2013.01); *A61K 9/14* (2013.01); *A61K 9/5015* (2013.01); *A61K 38/26* (2013.01); *A61K 38/28* (2013.01); *B01D 1/18* (2013.01)

(58) Field of Classification Search
CPC ...... C07D 241/08; B01D 1/18; A61K 9/5015; A61K 9/14; A61K 38/26; A61K 38/28
See application file for complete search history.

(56) References Cited

U.S. PATENT DOCUMENTS 2,549,303 A 4/1951 Friden
2,754,276 A 7/1956 Joseph et al.
(Continued)

FOREIGN PATENT DOCUMENTS

CA 2536047 A1 3/2005
CA 2551182 C 8/2010
(Continued)

OTHER PUBLICATIONS

Hache et al, Inhaled prostacyclin (PGI2) is an effective addition to the treatment of pulmonary hypertension and hypoxia in the operating room and intensive care unit, 2001, Can J Anesth, 48:9, pp. 924-929. (Year: 2001).*
(Continued)

*Primary Examiner* — Trevor Love
(74) *Attorney, Agent, or Firm* — K&L Gates LLP; Louis C. Cullman; Hal Gibson

(57) ABSTRACT

Disclosed herein are DKP microcrystals made by an improved method where they do not irreversibly self-assemble into microparticles. The microcrystals can be dispersed by atomization and re-formed by spray drying into particles having spherical shell morphology. Active agents and excipients can be incorporated into the particles by spray drying a solution containing the components to be
(Continued)

incorporated into microcrystalline diketopiperazine particles. In particular, the microcrystalline particle compositions are suitable for pulmonary drug delivery of one or more peptides, proteins, nucleic acids and/or small organic molecules.

21 Claims, 7 Drawing Sheets

(51) Int. Cl.

| | |
|---|---|
| *A61K 9/50* | (2006.01) |
| *A61K 9/14* | (2006.01) |
| *A61K 38/26* | (2006.01) |
| *A61K 38/28* | (2006.01) |

(56) References Cited

U.S. PATENT DOCUMENTS

| | | | |
|---|---|---|---|
| D189,076 | S | 10/1960 | Altman |
| 3,337,740 | A | 8/1967 | Gray et al. |
| 3,407,203 | A | 10/1968 | Buijle |
| 3,518,340 | A | 6/1970 | Raper |
| 3,622,053 | A | 11/1971 | Ryden |
| 3,673,698 | A | 7/1972 | Guerard |
| 3,669,113 | A | 8/1972 | Altounyan et al. |
| 3,823,816 | A | 7/1974 | Controullis et al. |
| 3,823,843 | A | 7/1974 | Stephens et al. |
| 3,856,142 | A | 12/1974 | Vessalo |
| 3,873,651 | A | 3/1975 | Mosley, Jr. et al. |
| 3,906,950 | A | 9/1975 | Cocozza |
| 3,921,637 | A | 11/1975 | Bennie et al. |
| 3,976,773 | A | 8/1976 | Curran et al. |
| 3,980,074 | A | 9/1976 | Watt et al. |
| 3,998,226 | A | 12/1976 | Harris |
| 4,013,075 | A | 3/1977 | Cocozza |
| 4,018,619 | A | 4/1977 | Webster et al. |
| 4,022,749 | A | 5/1977 | Kuechler |
| 4,040,536 | A | 8/1977 | Schwarz |
| 4,047,525 | A | 9/1977 | Kulessa et al. |
| 4,066,756 | A | 1/1978 | Orr et al. |
| 4,078,128 | A | 3/1978 | Hoyt et al. |
| 4,091,077 | A | 5/1978 | Smith et al. |
| 4,098,273 | A | 7/1978 | Glenn |
| 4,102,953 | A | 7/1978 | Johnson et al. |
| 4,110,240 | A | 8/1978 | Leo et al. |
| 4,148,308 | A | 4/1979 | Sayer |
| 4,153,689 | A | 5/1979 | Hirai |
| D252,707 | S | 8/1979 | Besnard |
| 4,168,002 | A | 9/1979 | Crosby |
| 4,171,000 | A | 10/1979 | Uhle |
| 4,175,556 | A | 11/1979 | Freezer |
| 4,187,129 | A | 2/1980 | Bost et al. |
| 4,196,196 | A | 4/1980 | Tiholiz |
| 4,206,758 | A | 6/1980 | Hallworth et al. |
| 4,210,140 | A | 7/1980 | James et al. |
| 4,211,769 | A | 7/1980 | Okada |
| 4,268,460 | A | 5/1981 | Boiarski et al. |
| 4,272,398 | A | 6/1981 | Jaffe |
| 4,275,820 | A | 6/1981 | LeBlond |
| 4,289,759 | A | 9/1981 | Heavener |
| 4,294,829 | A | 10/1981 | Suzuki |
| 4,300,546 | A | 11/1981 | Kruber |
| 4,356,167 | A | 10/1982 | Kelly |
| D269,463 | S | 6/1983 | Young et al. |
| 4,407,525 | A | 10/1983 | Hoppe |
| 4,456,007 | A | 6/1984 | Nakao et al. |
| 4,483,922 | A | 11/1984 | Carpenter |
| D276,654 | S | 12/1984 | Snellman-Wasenius et al. |
| 4,487,327 | A | 12/1984 | Grayson |
| 4,524,769 | A | 6/1985 | Wetterlin |
| 4,526,804 | A | 7/1985 | Escallon |
| 4,534,345 | A | 8/1985 | Wetterlin |
| D282,209 | S | 1/1986 | Newell et al. |
| 4,581,020 | A | 4/1986 | Mittleman |
| 4,592,348 | A | 6/1986 | Waters, IV et al. |
| 4,613,500 | A | 9/1986 | Suzuki |
| 4,615,817 | A | 10/1986 | McCoy |
| 4,624,861 | A | 11/1986 | Yale et al. |
| 4,637,996 | A | 1/1987 | Konishi |
| D288,852 | S | 3/1987 | Miyoshi |
| 4,659,696 | A | 4/1987 | Hirai et al. |
| 4,668,218 | A | 5/1987 | Virtanen |
| 4,681,752 | A | 7/1987 | Melillo |
| D295,321 | S | 4/1988 | Hallworth |
| 4,757,066 | A | 7/1988 | Shiokari et al. |
| 4,792,451 | A | 12/1988 | Kim |
| 4,811,731 | A | 3/1989 | Newell et al. |
| D301,273 | S | 5/1989 | Leonard |
| 4,835,312 | A | 5/1989 | Itoh et al. |
| 4,841,964 | A | 6/1989 | Hurka et al. |
| 4,847,091 | A | 7/1989 | Illum |
| 4,849,227 | A | 7/1989 | Cho |
| 4,861,627 | A | 8/1989 | Mathiowitz |
| 4,866,051 | A | 9/1989 | Hunt et al. |
| 4,873,087 | A | 10/1989 | Morishita et al. |
| 4,887,722 | A | 12/1989 | Greenward, Sr. |
| 4,900,730 | A | 2/1990 | Miyauchi |
| 4,907,583 | A | 3/1990 | Wetterlin et al. |
| 4,925,673 | A | 5/1990 | Steiner |
| 4,926,852 | A | 5/1990 | Zoltan et al. |
| 4,927,555 | A | 5/1990 | Colarusso, Jr. |
| 4,927,928 | A | 5/1990 | Shroot et al. |
| 4,946,828 | A | 8/1990 | Markussen |
| 4,981,295 | A | 1/1991 | Belman et al. |
| 4,981,625 | A | 1/1991 | Rhim et al. |
| 4,983,402 | A | 1/1991 | Steiner et al. |
| 4,984,158 | A | 1/1991 | Hillsman |
| 4,991,605 | A | 2/1991 | Keritsis |
| 4,998,624 | A | 3/1991 | Capes et al. |
| 5,006,343 | A | 4/1991 | Benson |
| D316,902 | S | 5/1991 | Hoefling |
| 5,017,383 | A | 5/1991 | Ozawa et al. |
| 5,019,400 | A | 5/1991 | Gombotz et al. |
| 5,021,376 | A | 6/1991 | Nienburg et al. |
| 5,027,806 | A | 7/1991 | Zoltan et al. |
| 5,042,975 | A | 8/1991 | Chien |
| D321,570 | S | 11/1991 | Blasdell et al. |
| 5,067,500 | A | 11/1991 | Keritsis |
| 5,069,204 | A | 12/1991 | Smith et al. |
| 5,074,418 | A | 12/1991 | Buan et al. |
| 5,075,027 | A | 12/1991 | Dixit et al. |
| 5,098,590 | A | 3/1992 | Dixit et al. |
| 5,105,291 | A | 4/1992 | Matsumoto et al. |
| D326,517 | S | 5/1992 | Funai et al. |
| 5,110,007 | A | 5/1992 | Law et al. |
| 5,110,823 | A | 5/1992 | Hamaguchi et al. |
| 5,118,666 | A | 6/1992 | Habener |
| 5,120,712 | A | 6/1992 | Habener |
| 5,124,291 | A | 6/1992 | Bremer et al. |
| 5,131,539 | A | 7/1992 | Karita et al. |
| 5,139,878 | A | 8/1992 | Kim |
| 5,145,684 | A | 9/1992 | Liversidge et al. |
| 5,152,284 | A | 10/1992 | Valentini et al. |
| D331,106 | S | 11/1992 | Fuchs |
| 5,167,506 | A | 12/1992 | Kilis et al. |
| 5,170,801 | A | 12/1992 | Casper et al. |
| 5,188,837 | A | 2/1993 | Domb |
| 5,196,049 | A | 3/1993 | Coombs et al. |
| 5,201,308 | A | 4/1993 | Newhouse |
| 5,203,768 | A | 4/1993 | Haak et al. |
| 5,204,108 | A | 4/1993 | Ilium |
| 5,208,998 | A | 5/1993 | Dyler, Jr. |
| 5,215,739 | A | 6/1993 | Kamishita et al. |
| D337,636 | S | 7/1993 | Kocinski |
| D338,062 | S | 8/1993 | Yair |
| D338,268 | S | 8/1993 | Kobayashi et al. |
| 5,239,992 | A | 8/1993 | Bougamont et al. |
| 5,244,653 | A | 9/1993 | Berke et al. |
| 5,250,287 | A | 10/1993 | Cocozza |
| D340,975 | S | 11/1993 | Sladek |
| 5,260,306 | A | 11/1993 | Boardman et al. |
| 5,270,305 | A | 12/1993 | Palmer |
| 5,287,850 | A | 2/1994 | Haber et al. |

(56) References Cited

U.S. PATENT DOCUMENTS

| | | | |
|---|---|---|---|
| D344,796 S | 3/1994 | Sochon et al. | |
| D344,797 S | 3/1994 | Sochon et al. | |
| D345,013 S | 3/1994 | Huck et al. | |
| 5,301,666 A | 4/1994 | Lerk et al. | |
| 5,306,453 A | 4/1994 | Shulman | |
| D347,057 S | 5/1994 | Yair | |
| D348,100 S | 6/1994 | Clarke | |
| 5,320,094 A | 6/1994 | Laube et al. | |
| D348,928 S | 7/1994 | Ashley et al. | |
| D348,929 S | 7/1994 | Paton | |
| 5,327,883 A | 7/1994 | Williams et al. | |
| 5,328,464 A | 7/1994 | Kriesel et al. | |
| 5,331,953 A | 7/1994 | Andersson et al. | |
| 5,333,106 A | 7/1994 | Lanpher et al. | |
| D349,572 S | 8/1994 | Jagnandan et al. | |
| D350,193 S | 8/1994 | Huck et al. | |
| 5,337,740 A | 8/1994 | Armstrong et al. | |
| D350,602 S | 9/1994 | Hobbs et al. | |
| D350,821 S | 9/1994 | Wright et al. | |
| 5,351,683 A | 10/1994 | Chiesi et al. | |
| 5,352,461 A | 10/1994 | Feldstein et al. | |
| 5,354,562 A | 10/1994 | Platz | |
| 5,358,734 A | 10/1994 | Lenox et al. | |
| D352,107 S | 11/1994 | Meier et al. | |
| 5,360,614 A | 11/1994 | Fox et al. | |
| 5,363,842 A | 11/1994 | Mishelevich et al. | |
| 5,364,838 A | 11/1994 | Rubsamen | |
| 5,372,128 A | 12/1994 | Haber et al. | |
| D355,029 S | 1/1995 | Kinneir et al. | |
| 5,385,904 A | 1/1995 | Andersson et al. | |
| 5,394,868 A | 3/1995 | Ambrosio et al. | |
| 5,401,516 A | 3/1995 | Milstein et al. | |
| D357,603 S | 4/1995 | Wolff | |
| 5,404,871 A | 4/1995 | Goodman et al. | |
| D358,880 S | 5/1995 | Mulhauser et al. | |
| 5,413,804 A | 5/1995 | Rhodes | |
| 5,415,162 A | 5/1995 | Casper et al. | |
| D359,153 S | 6/1995 | Viggiano | |
| D359,555 S | 6/1995 | Funai et al. | |
| 5,424,286 A | 6/1995 | Eng | |
| 5,437,271 A | 8/1995 | Hodson et al. | |
| 5,443,841 A | 8/1995 | Milstein et al. | |
| D362,500 S | 9/1995 | Cook et al. | |
| 5,447,150 A | 9/1995 | Bacon | |
| 5,447,151 A | 9/1995 | Bruna et al. | |
| 5,447,728 A | 9/1995 | Milstein et al. | |
| 5,451,410 A | 9/1995 | Milstein et al. | |
| D363,775 S | 10/1995 | Hobbs | |
| 5,454,871 A | 10/1995 | Liaw et al. | |
| 5,455,335 A | 10/1995 | Kahne et al. | |
| 5,458,135 A | 10/1995 | Patton et al. | |
| 5,469,750 A | 11/1995 | Lloyd et al. | |
| 5,469,971 A | 11/1995 | Chilton et al. | |
| 5,476,093 A | 12/1995 | Laniken | |
| 5,477,285 A | 12/1995 | Riddle et al. | |
| D365,876 S | 1/1996 | Chawla | |
| 5,482,032 A | 1/1996 | Smith et al. | |
| 5,482,927 A | 1/1996 | Maniar et al. | |
| 5,483,954 A | 1/1996 | Mecikalski | |
| 5,484,606 A | 1/1996 | Dhaber et al. | |
| 5,487,378 A | 1/1996 | Robertson et al. | |
| 5,492,112 A | 2/1996 | Mecikalski et al. | |
| D368,364 S | 4/1996 | Reitano et al. | |
| 5,503,144 A | 4/1996 | Bacon | |
| 5,503,852 A | 4/1996 | Steiner et al. | |
| 5,505,194 A | 4/1996 | Adjei et al. | |
| 5,506,203 A | 4/1996 | Backstorm et al. | |
| D370,255 S | 5/1996 | Yamamoto et al. | |
| 5,514,646 A | 5/1996 | Chance et al. | |
| 5,518,998 A | 5/1996 | Backstorm et al. | |
| 5,524,613 A | 6/1996 | Haber et al. | |
| 5,532,461 A | 7/1996 | Crummenauer et al. | |
| 5,533,502 A | 7/1996 | Piper | |
| 5,533,505 A | 7/1996 | Kallstrand et al. | |
| 5,541,155 A | 7/1996 | Leone-Bay | |
| 5,542,411 A | 8/1996 | Rex | |
| 5,542,539 A | 8/1996 | Early | |
| 5,545,618 A | 8/1996 | Buckley et al. | |
| 5,547,929 A | 8/1996 | Anderson, Jr. et al. | |
| 5,562,909 A | 10/1996 | Allcock et al. | |
| 5,562,918 A | 10/1996 | Stimpson | |
| 5,568,884 A | 10/1996 | Bruna | |
| 5,570,810 A | 11/1996 | Lambelet, Jr. et al. | |
| 5,571,795 A | 11/1996 | Kahne et al. | |
| 5,574,008 A | 11/1996 | Johnson et al. | |
| 5,577,497 A | 11/1996 | Mecikalski et al. | |
| 5,578,323 A | 11/1996 | Milstein et al. | |
| 5,584,417 A | 12/1996 | Graf et al. | |
| D377,215 S | 1/1997 | Rand | |
| D377,686 S | 1/1997 | Waldeck et al. | |
| 5,595,175 A | 1/1997 | Malcher et al. | |
| 5,596,701 A | 1/1997 | Augusteijn et al. | |
| D377,861 S | 2/1997 | Jacober | |
| 5,598,835 A | 2/1997 | von Schrader | |
| 5,601,846 A | 2/1997 | Milstein et al. | |
| 5,610,271 A | 3/1997 | Dooley et al. | |
| 5,614,492 A | 3/1997 | Habener | |
| 5,615,670 A | 4/1997 | Rhodes et al. | |
| 5,617,844 A | 4/1997 | King | |
| 5,619,984 A | 4/1997 | Hodson et al. | |
| 5,622,164 A | 4/1997 | Kilis et al. | |
| 5,622,166 A | 4/1997 | Eisele et al. | |
| 5,623,724 A | 4/1997 | Gurkovich et al. | |
| 5,623,920 A | 4/1997 | Bryant | |
| D379,506 S | 5/1997 | Maher | |
| 5,629,020 A | 5/1997 | Leone-Bay | |
| 5,631,224 A | 5/1997 | Efendic et al. | |
| 5,632,971 A | 5/1997 | Yang | |
| 5,634,900 A | 6/1997 | Makino et al. | |
| 5,639,441 A | 6/1997 | Sievers et al. | |
| 5,641,861 A | 6/1997 | Dooley et al. | |
| D381,416 S | 7/1997 | Hansson et al. | |
| 5,642,727 A | 7/1997 | Datta et al. | |
| 5,642,728 A | 7/1997 | Andersson et al. | |
| 5,643,957 A | 7/1997 | Leone-Bay et al. | |
| 5,645,051 A | 7/1997 | Schultz | |
| 5,651,359 A | 7/1997 | Bougamont et al. | |
| 5,653,961 A | 8/1997 | McNally et al. | |
| 5,655,516 A | 8/1997 | Goodman et al. | |
| 5,655,523 A | 8/1997 | Hodson et al. | |
| 5,657,748 A | 8/1997 | Braithwaite | |
| 5,658,878 A | 8/1997 | Backstrom et al. | |
| 5,660,169 A | 8/1997 | Kallstrand et al. | |
| 5,672,581 A | 9/1997 | Rubsamen et al. | |
| 5,673,686 A | 10/1997 | Villax et al. | |
| 5,679,377 A | 10/1997 | Bernstein et al. | |
| 5,687,710 A | 11/1997 | Ambrosio et al. | |
| 5,690,910 A | 11/1997 | Ahmed et al. | |
| 5,693,338 A | 12/1997 | Milstein | |
| 5,699,789 A | 12/1997 | Hendricks | |
| D389,238 S | 1/1998 | Kirk, III et al. | |
| D389,570 S | 1/1998 | Savolainen | |
| 5,705,483 A | 1/1998 | Galloway et al. | |
| D390,651 S | 2/1998 | Smith et al. | |
| D390,653 S | 2/1998 | Blasdell et al. | |
| 5,714,007 A | 2/1998 | Pletcher et al. | |
| 5,714,167 A | 2/1998 | Milstein et al. | |
| 5,727,333 A | 3/1998 | Folan | |
| 5,727,546 A | 3/1998 | Clarke et al. | |
| 5,740,793 A | 4/1998 | Hodson et al. | |
| 5,740,794 A | 4/1998 | Smith et al. | |
| 5,746,197 A | 5/1998 | Williams | |
| 5,746,227 A | 5/1998 | Rose et al. | |
| 5,747,445 A | 5/1998 | Backstrom et al. | |
| 5,752,505 A | 5/1998 | Ohki et al. | |
| 5,755,218 A | 5/1998 | Johansson et al. | |
| D395,147 S | 6/1998 | Vidgren et al. | |
| D395,499 S | 6/1998 | Eisele et al. | |
| 5,758,638 A | 6/1998 | Kreamer | |
| 5,763,396 A | 6/1998 | Weiner et al. | |
| 5,766,620 A | 6/1998 | Heiber et al. | |
| 5,766,633 A | 6/1998 | Milstein et al. | |
| 5,769,073 A | 6/1998 | Eason et al. | |
| 5,772,085 A | 6/1998 | Bryant et al. | |

(56) References Cited

U.S. PATENT DOCUMENTS

| | | | |
|---|---|---|---|
| RE35,862 | E | 7/1998 | Steiner et al. |
| 5,775,320 | A | 7/1998 | Patton et al. |
| 5,785,049 | A | 7/1998 | Smith et al. |
| 5,785,989 | A | 7/1998 | Stanley et al. |
| D397,435 | S | 8/1998 | Naumann |
| 5,792,451 | A | 8/1998 | Sarubbi et al. |
| 5,794,613 | A | 8/1998 | Piskorski |
| 5,797,391 | A | 8/1998 | Cook et al. |
| D398,992 | S | 9/1998 | Feret |
| 5,799,821 | A | 9/1998 | Lambelet, Jr. et al. |
| 5,807,315 | A | 9/1998 | Va Antwerp et al. |
| 5,809,997 | A | 9/1998 | Wolf |
| 5,811,127 | A | 9/1998 | Milstein et al. |
| 5,813,397 | A | 9/1998 | Goodman et al. |
| 5,817,343 | A | 10/1998 | Burke |
| 5,824,345 | A | 10/1998 | Milstein et al. |
| 5,839,429 | A | 11/1998 | Marnfeldt et al. |
| 5,840,279 | A | 11/1998 | Narodylo et al. |
| 5,840,340 | A | 11/1998 | Milstein et al. |
| 5,846,447 | A | 12/1998 | Beatty |
| 5,848,589 | A | 12/1998 | Welnetz |
| 5,849,322 | A | 12/1998 | Ebert et al. |
| 5,857,457 | A | 1/1999 | Hyppola |
| 5,858,099 | A | 1/1999 | Sun et al. |
| 5,865,012 | A | 2/1999 | Hansson et al. |
| 5,868,774 | A | 2/1999 | Reil |
| 5,874,064 | A | 2/1999 | Edwards et al. |
| 5,875,776 | A | 3/1999 | Vaghefi |
| 5,877,174 | A | 3/1999 | Ono et al. |
| 5,881,719 | A | 3/1999 | Gottenauer et al. |
| 5,881,721 | A | 3/1999 | Bunce et al. |
| 5,884,620 | A | 3/1999 | Gonda et al. |
| 5,888,477 | A | 3/1999 | Gonda et al. |
| 5,896,855 | A | 4/1999 | Hobbs et al. |
| 5,901,703 | A | 5/1999 | Ohki et al. |
| 5,904,139 | A | 5/1999 | Hauser |
| D410,541 | S | 6/1999 | Moulin |
| D411,005 | S | 6/1999 | Coe |
| 5,908,639 | A | 6/1999 | Simpkin et al. |
| 5,912,011 | A | 6/1999 | Makino et al. |
| 5,918,594 | A | 7/1999 | Asking et al. |
| 5,919,897 | A | 7/1999 | Dooley et al. |
| 5,921,237 | A | 7/1999 | Eisele et al. |
| 5,922,253 | A | 7/1999 | Herbert et al. |
| 5,924,419 | A | 7/1999 | Kotliar |
| 5,929,027 | A | 7/1999 | Takama et al. |
| D412,572 | S | 8/1999 | Gray |
| D412,744 | S | 8/1999 | Braithwaite |
| D412,978 | S | 8/1999 | Cameron |
| D412,979 | S | 8/1999 | Weinstein et al. |
| 5,934,273 | A | 8/1999 | Andersson et al. |
| 5,942,242 | A | 8/1999 | Mizushima et al. |
| 5,972,242 | A | 8/1999 | Mizushima et al. |
| 5,948,749 | A | 9/1999 | Igarashi et al. |
| 5,952,008 | A | 9/1999 | Backstrom et al. |
| 5,954,047 | A | 9/1999 | Armer et al. |
| 5,965,701 | A | 10/1999 | Junien |
| 5,971,951 | A | 10/1999 | Ruskewicz |
| D416,085 | S | 11/1999 | Forssell et al. |
| D416,621 | S | 11/1999 | Forssell et al. |
| D416,998 | S | 11/1999 | Hodson et al. |
| D417,271 | S | 11/1999 | Denyer et al. |
| 5,975,347 | A | 11/1999 | Lambelet, Jr. et al. |
| 5,976,569 | A | 11/1999 | Milstein |
| 5,976,574 | A | 11/1999 | Gordon |
| 5,977,071 | A | 11/1999 | Galloway et al. |
| 5,980,865 | A | 11/1999 | Ahmed et al. |
| 5,981,488 | A | 11/1999 | Hoffman |
| 5,983,893 | A | 11/1999 | Wetterlin |
| 5,985,248 | A | 11/1999 | Gordon et al. |
| 5,985,309 | A | 11/1999 | Edwards et al. |
| 5,990,077 | A | 11/1999 | Drucker |
| D417,732 | S | 12/1999 | Dagsland et al. |
| D417,912 | S | 12/1999 | Dagsland et al. |
| 5,996,577 | A | 12/1999 | Ohki et al. |
| 5,997,848 | A | 12/1999 | Patton et al. |
| 6,001,336 | A | 12/1999 | Gordon |
| 6,006,747 | A | 12/1999 | Eisele et al. |
| 6,006,753 | A | 12/1999 | Efendic |
| D418,600 | S | 1/2000 | Haerle |
| D420,736 | S | 2/2000 | Moulin |
| 6,026,809 | A | 2/2000 | Abrams et al. |
| 6,029,663 | A | 2/2000 | Eisele et al. |
| D421,800 | S | 3/2000 | Doat |
| 6,039,208 | A | 3/2000 | Lambelet et al. |
| 6,043,214 | A | 3/2000 | Jensen et al. |
| 6,045,828 | A | 4/2000 | Bystorm et al. |
| 6,051,256 | A | 4/2000 | Platz et al. |
| 6,051,551 | A | 4/2000 | Hughes et al. |
| 6,055,980 | A | 5/2000 | Mecikalski et al. |
| 6,056,169 | A | 5/2000 | Bruna et al. |
| 6,060,069 | A | 5/2000 | Hill et al. |
| 6,063,910 | A | 5/2000 | Debenedetti et al. |
| 6,071,497 | A | 6/2000 | Steiner et al. |
| 6,073,629 | A | 6/2000 | Hardy et al. |
| 6,076,521 | A | 6/2000 | Lindahl et al. |
| 6,077,543 | A | 6/2000 | Gordon et al. |
| 6,080,762 | A | 6/2000 | Allen et al. |
| 6,085,745 | A | 6/2000 | Levander et al. |
| D428,486 | S | 7/2000 | Schuckmann |
| 6,087,334 | A | 7/2000 | Beeley et al. |
| 6,087,351 | A | 7/2000 | Nye |
| 6,089,228 | A | 7/2000 | Smith et al. |
| 6,095,136 | A | 8/2000 | Virtanen |
| 6,098,618 | A | 8/2000 | Jennings et al. |
| 6,098,619 | A | 8/2000 | Britto et al. |
| 6,102,035 | A | 8/2000 | Asking et al. |
| 6,105,571 | A | 8/2000 | Coffee |
| 6,105,574 | A | 8/2000 | Jahnsson |
| 6,109,261 | A | 8/2000 | Clarke et al. |
| 6,109,481 | A | 8/2000 | Alexander et al. |
| 6,099,517 | A | 9/2000 | Daughtery |
| 6,116,237 | A | 9/2000 | Schultz |
| 6,116,238 | A | 9/2000 | Jackson et al. |
| 6,116,239 | A | 9/2000 | Volgyesi |
| 6,119,684 | A | 9/2000 | Nohl et al. |
| 6,119,688 | A | 9/2000 | Whaley et al. |
| 6,131,567 | A | 10/2000 | Gonda et al. |
| 6,132,766 | A | 10/2000 | Sankaram et al. |
| 6,133,235 | A | 10/2000 | Galloway et al. |
| 6,142,145 | A | 11/2000 | Dagsland |
| 6,152,130 | A | 11/2000 | Abrams |
| 6,153,613 | A | 11/2000 | Ono et al. |
| 6,155,423 | A | 12/2000 | Katzne et al. |
| 6,156,114 | A | 12/2000 | Bell et al. |
| 6,158,431 | A | 12/2000 | Poole |
| 6,159,360 | A | 12/2000 | Gerteis et al. |
| RE37,053 | E | 2/2001 | Hanes et al. |
| 6,182,655 | B1 | 2/2001 | Keller et al. |
| 6,187,291 | B1 | 2/2001 | Weinstein et al. |
| 6,191,102 | B1 | 2/2001 | DiMarchi et al. |
| 6,192,876 | B1 | 2/2001 | Denyer et al. |
| 6,193,844 | B1 | 2/2001 | McLaughlin et al. |
| 6,193,957 | B1 | 2/2001 | Ahmed |
| D438,612 | S | 3/2001 | Suh |
| D439,325 | S | 3/2001 | Frost |
| D439,656 | S | 3/2001 | Andersson et al. |
| 6,198,847 | B1 | 3/2001 | Washizawa |
| D441,446 | S | 5/2001 | Dagsland et al. |
| D441,859 | S | 5/2001 | Pera |
| D442,685 | S | 5/2001 | Sladek |
| 6,235,725 | B1 | 5/2001 | Ahmed |
| D444,226 | S | 6/2001 | Geert-Jensen et al. |
| 6,250,300 | B1 | 6/2001 | Andersson et al. |
| 6,254,854 | B1 | 7/2001 | Edwards et al. |
| 6,257,232 | B1 | 7/2001 | Andersson et al. |
| 6,258,816 | B1 | 7/2001 | Singh et al. |
| 6,263,871 | B1 | 7/2001 | Brown et al. |
| 6,269,952 | B1 | 8/2001 | Watt et al. |
| 6,273,084 | B1 | 8/2001 | Frid |
| 6,273,085 | B1 | 8/2001 | Eisele et al. |
| 6,273,086 | B1 | 8/2001 | Ohki et al. |
| 6,277,819 | B1 | 8/2001 | Efendic |
| 6,279,511 | B1 | 8/2001 | Loughnane |

(56) References Cited

U.S. PATENT DOCUMENTS

| | | | |
|---|---|---|---|
| D448,076 | S | 9/2001 | von Shuckmann |
| 6,286,506 | B1 | 9/2001 | MacAndrew et al. |
| 6,286,507 | B1 | 9/2001 | Jahnsson |
| 6,294,204 | B1 | 9/2001 | Rossling et al. |
| D449,684 | S | 10/2001 | Christup et al. |
| 6,298,846 | B1 | 10/2001 | Ohki et al. |
| 6,298,847 | B1 | 10/2001 | Datta et al. |
| D450,117 | S | 11/2001 | Braithwaite et al. |
| D451,597 | S | 12/2001 | Suh |
| 6,328,034 | B1 | 12/2001 | Eisele et al. |
| 6,331,318 | B1 | 12/2001 | Milstein |
| D452,910 | S | 1/2002 | Braithwaite et al. |
| 6,335,316 | B1 | 1/2002 | Hughes et al. |
| D453,264 | S | 2/2002 | Acevedo, Jr. |
| 6,347,629 | B1 | 2/2002 | Braithwaite |
| 6,348,447 | B1 | 2/2002 | Hellstorm et al. |
| 6,357,442 | B1 | 3/2002 | Casper et al. |
| 6,358,058 | B1 | 3/2002 | Strupat et al. |
| 6,358,924 | B1 | 3/2002 | Hoffman |
| 6,360,743 | B1 | 3/2002 | Andersson et al. |
| 6,360,929 | B1 | 3/2002 | McCarthy |
| D455,208 | S | 4/2002 | Bacon et al. |
| 6,363,932 | B1 | 4/2002 | Forchione et al. |
| 6,365,190 | B1 | 4/2002 | Gordon et al. |
| 6,372,258 | B1 | 4/2002 | Platz et al. |
| 6,375,975 | B1 | 4/2002 | Modi |
| 6,380,357 | B2 | 4/2002 | Hermeling et al. |
| 6,386,195 | B1 | 5/2002 | Coffee |
| 6,388,053 | B1 | 5/2002 | Galloway et al. |
| 6,394,085 | B1 | 5/2002 | Hardy et al. |
| 6,395,300 | B1 | 5/2002 | Straub et al. |
| 6,395,744 | B1 | 5/2002 | Adams et al. |
| 6,395,774 | B1 | 5/2002 | Milstein |
| 6,410,513 | B1 | 6/2002 | Galloway et al. |
| D460,173 | S | 7/2002 | Harrison et al. |
| 6,415,784 | B1 | 7/2002 | Christup et al. |
| 6,418,926 | B1 | 7/2002 | Chawla |
| 6,423,344 | B1 | 7/2002 | Platz et al. |
| D461,239 | S | 8/2002 | Cassidy |
| 6,427,688 | B1 | 8/2002 | Ligotke et al. |
| 6,428,771 | B1 | 8/2002 | Steiner et al. |
| 6,428,805 | B1 | 8/2002 | Dohi et al. |
| 6,432,383 | B1 | 8/2002 | Modi |
| 6,436,443 | B2 | 8/2002 | Edwards et al. |
| 6,439,227 | B1 | 8/2002 | Myrman et al. |
| 6,440,463 | B1 | 8/2002 | Feldstein et al. |
| 6,441,172 | B1 | 8/2002 | Nefzi et al. |
| D463,544 | S | 9/2002 | Engelberth et al. |
| 6,443,143 | B1 | 9/2002 | Ishida et al. |
| 6,444,226 | B1 | 9/2002 | Steiner et al. |
| 6,446,626 | B1 | 9/2002 | Virtanen |
| 6,446,627 | B1 | 9/2002 | Bowman et al. |
| 6,447,750 | B1 | 9/2002 | Cutie et al. |
| 6,447,751 | B1 | 9/2002 | Weinstein et al. |
| 6,447,753 | B2 | 9/2002 | Edwards et al. |
| 6,451,337 | B1 | 9/2002 | Smith et al. |
| 6,457,470 | B1 | 10/2002 | Coffee |
| 6,468,507 | B1 | 10/2002 | Cutie et al. |
| 6,470,884 | B2 | 10/2002 | Horlin |
| 6,479,049 | B1 | 11/2002 | Platz et al. |
| 6,484,715 | B1 | 11/2002 | Ritsche et al. |
| 6,484,717 | B1 | 11/2002 | Dagsland et al. |
| D469,527 | S | 1/2003 | Keller et al. |
| 6,503,480 | B1 | 1/2003 | Edwards et al. |
| 6,509,006 | B1 | 1/2003 | Platz et al. |
| 6,509,313 | B1 | 1/2003 | Smith |
| D469,866 | S | 2/2003 | Albulet et al. |
| 6,514,482 | B1 | 2/2003 | Bartus et al. |
| 6,518,239 | B1 | 2/2003 | Kuo et al. |
| 6,523,536 | B2 | 2/2003 | Fugelsang et al. |
| D471,273 | S | 3/2003 | Albulet et al. |
| 6,528,096 | B1 | 3/2003 | Musa et al. |
| 6,532,437 | B1 | 3/2003 | Clardy et al. |
| 6,536,427 | B2 | 3/2003 | Davies et al. |
| D473,298 | S | 4/2003 | Bowman et al. |
| D473,640 | S | 4/2003 | Cuffaro et al. |
| 6,540,672 | B1 | 4/2003 | Simonsen et al. |
| 6,540,982 | B1 | 4/2003 | Adjei et al. |
| 6,540,983 | B1 | 4/2003 | Adjei et al. |
| 6,543,448 | B1 | 4/2003 | Smith et al. |
| 6,546,929 | B2 | 4/2003 | Burr et al. |
| 6,555,127 | B2 | 4/2003 | Steiner |
| 6,555,521 | B2 | 4/2003 | Hermeling et al. |
| D474,536 | S | 5/2003 | Albulet et al. |
| D475,133 | S | 5/2003 | McLuckie |
| 6,557,549 | B2 | 5/2003 | Schmidt et al. |
| 6,561,186 | B2 | 5/2003 | Casper et al. |
| 6,567,686 | B2 | 5/2003 | Sexton |
| 6,568,390 | B2 | 5/2003 | Nichols et al. |
| 6,569,406 | B2 | 5/2003 | Stevenson et al. |
| 6,571,793 | B1 | 6/2003 | Nilsson et al. |
| 6,572,893 | B2 | 6/2003 | Gordon et al. |
| 6,575,160 | B1 | 6/2003 | Volgyesi |
| 6,575,162 | B1 | 6/2003 | Rand |
| 6,578,571 | B1 | 6/2003 | Watt |
| 6,582,728 | B1 | 6/2003 | Platz et al. |
| 6,583,111 | B1 | 6/2003 | DiMarchi |
| D477,665 | S | 7/2003 | Myrman et al. |
| 6,589,560 | B2 | 7/2003 | Foster et al. |
| 6,591,832 | B1 | 7/2003 | DeJonge |
| 6,592,904 | B2 | 7/2003 | Platz et al. |
| 6,595,205 | B2 | 7/2003 | Andersson et al. |
| 6,595,208 | B1 | 7/2003 | Coffee et al. |
| D478,983 | S | 8/2003 | Whitehall et al. |
| 6,606,992 | B1 | 8/2003 | Schuler et al. |
| D479,745 | S | 9/2003 | Albulet et al. |
| 6,613,308 | B2 | 9/2003 | Bartus et al. |
| 6,615,987 | B1 | 9/2003 | Greenhill et al. |
| 6,620,910 | B1 | 9/2003 | Calas et al. |
| 6,626,173 | B2 | 9/2003 | Genova et al. |
| D480,806 | S | 10/2003 | Engelberth et al. |
| 6,630,169 | B1 | 10/2003 | Bot et al. |
| 6,632,258 | B1 | 10/2003 | Wheelock et al. |
| 6,632,456 | B1 | 10/2003 | Backstrom et al. |
| 6,635,283 | B2 | 10/2003 | Edwards et al. |
| 6,637,431 | B2 | 10/2003 | Ekelius et al. |
| 6,640,050 | B2 | 10/2003 | Nichols et al. |
| 6,644,309 | B2 | 11/2003 | Casper et al. |
| 6,645,468 | B2 | 11/2003 | Cutie et al. |
| 6,645,504 | B1 | 11/2003 | Weiner et al. |
| 6,652,838 | B2 | 11/2003 | Weinstein et al. |
| 6,652,885 | B2 | 11/2003 | Steiner et al. |
| D483,860 | S | 12/2003 | Knoch |
| 6,655,379 | B2 | 12/2003 | Clark et al. |
| 6,655,380 | B1 | 12/2003 | Andersson et al. |
| 6,655,381 | B2 | 12/2003 | Keane et al. |
| 6,660,716 | B1 | 12/2003 | Yakubu-Madus et al. |
| 6,663,898 | B2 | 12/2003 | Milstein |
| 6,668,826 | B1 | 12/2003 | Myrman et al. |
| 6,672,304 | B1 | 1/2004 | Casper et al. |
| 6,676,931 | B2 | 1/2004 | Dugger, III. |
| 6,679,255 | B2 | 1/2004 | Pera |
| 6,681,767 | B1 | 1/2004 | Patton et al. |
| 6,681,768 | B2 | 1/2004 | Haaije de Boer et al. |
| 6,685,967 | B1 | 2/2004 | Patton et al. |
| 6,698,421 | B2 | 3/2004 | Attolini |
| 6,698,422 | B2 | 3/2004 | Fugelsang et al. |
| 6,701,917 | B2 | 3/2004 | O'Leary |
| 6,703,361 | B2 | 3/2004 | Weiner et al. |
| 6,703,365 | B2 | 3/2004 | Galloway et al. |
| 6,703,381 | B1 | 3/2004 | Ekwuribe et al. |
| 6,705,313 | B2 | 3/2004 | Niccolai |
| 6,715,486 | B2 | 4/2004 | Gieschen et al. |
| 6,715,487 | B2 | 4/2004 | Nichols et al. |
| 6,718,972 | B2 | 4/2004 | O'Leary |
| 6,720,407 | B1 | 4/2004 | Hughes et al. |
| 6,722,363 | B1 | 4/2004 | von Schuckmann |
| D489,448 | S | 5/2004 | Shayan |
| 6,729,324 | B2 | 5/2004 | Casper et al. |
| 6,729,328 | B2 | 5/2004 | Raul |
| 6,737,045 | B2 | 5/2004 | Patton |
| 6,745,761 | B2 | 6/2004 | Christup et al. |
| 6,747,006 | B2 | 6/2004 | Efendic |
| 6,748,946 | B1 | 6/2004 | Rand et al. |

(56) References Cited

U.S. PATENT DOCUMENTS 6,748,947 B2 6/2004 Keane et al.
6,752,145 B1 6/2004 Bonney et al.
6,755,190 B2 6/2004 Rasmussen
D492,769 S 7/2004 Hatanaka
D493,220 S 7/2004 Burge et al.
D493,519 S 7/2004 Jonsson et al.
6,774,112 B2 8/2004 Gougoutas
6,787,152 B2 9/2004 Kirby et al.
6,790,496 B1 9/2004 Levander et al.
6,792,945 B2 9/2004 Davies et al.
6,797,258 B2 9/2004 Platz et al.
6,799,572 B2 10/2004 Nichols et al.
6,800,643 B2 10/2004 Cuenoud et al.
6,803,044 B1 10/2004 Catania et al.
6,821,949 B2 11/2004 Bridon et al.
6,823,863 B2 11/2004 Huxham et al.
D499,802 S 12/2004 Pinon et al.
6,830,046 B2 12/2004 Blakley et al.
6,838,075 B2 1/2005 Stevenson et al.
6,838,076 B2 1/2005 Platton et al.
6,847,595 B2 1/2005 Tanaka
6,848,443 B2 2/2005 Schmidt et al.
6,849,708 B1 2/2005 Habener
6,852,690 B1 2/2005 Nauck et al.
6,858,199 B1 2/2005 Edwards et al.
6,860,262 B2 3/2005 Christup et al.
6,866,037 B1 3/2005 Aslin et al.
6,871,646 B2 3/2005 Keane et al.
6,871,647 B2 3/2005 Allan et al.
6,880,554 B1 4/2005 Coffee
6,881,423 B2 4/2005 Dohi et al.
6,884,435 B1 4/2005 O'Hagan et al.
6,887,459 B1 5/2005 Haeberlin
6,887,849 B2 5/2005 Bridon et al.
6,889,687 B1 5/2005 Olsson
6,892,728 B2 5/2005 Helgesson et al.
6,896,906 B2 5/2005 Hastedt et al.
D506,680 S 6/2005 Saelzer
6,904,907 B2 6/2005 Speldrich et al.
6,906,030 B2 6/2005 Milstein
6,916,354 B2 7/2005 Elliot
6,918,991 B2 7/2005 Chickering, III et al.
6,921,458 B2 7/2005 Chickering, III et al.
6,921,528 B2 7/2005 Edwards et al.
6,923,175 B2 8/2005 Poole et al.
D509,296 S 9/2005 Minshull et al.
D509,898 S 9/2005 Bunce et al.
6,948,496 B2 9/2005 Eason et al.
6,949,258 B2 9/2005 Zhang
6,951,215 B1 10/2005 Hoffman
6,953,812 B2 10/2005 Joregenson et al.
D511,208 S 11/2005 Pardonge et al.
D511,977 S 11/2005 Saelzer
6,962,006 B2 11/2005 Chickering, III et al.
D512,777 S 12/2005 Beisner et al.
6,979,437 B2 12/2005 Bartus et al.
D514,222 S 1/2006 Andersson et al.
6,981,499 B2 1/2006 Andersson et al.
6,989,155 B1 1/2006 Ganderton et al.
6,991,779 B2 1/2006 Steiner et al.
D515,696 S 2/2006 Lucking et al.
D515,924 S 2/2006 Grant
D516,211 S 2/2006 Minshull et al.
6,998,387 B1 2/2006 Goke et al.
D518,170 S 3/2006 Clarke et al.
D518,171 S 3/2006 Anderson et al.
7,022,674 B2 4/2006 DeFelippis et al.
7,025,056 B2 4/2006 Eason et al.
7,028,686 B2 4/2006 Gonda et al.
7,030,084 B2 4/2006 Ekwuribe et al.
7,032,593 B2 4/2006 Johnston et al.
7,035,294 B2 4/2006 Dove et al.
7,047,967 B2 5/2006 Knudsen
7,048,908 B2 5/2006 Basu et al.
7,060,274 B2 6/2006 Blumberg et al.
7,067,129 B2 6/2006 Blumberg et al.
7,077,130 B2 7/2006 Nichols et al.
7,080,642 B2 7/2006 Hodson et al.
7,084,243 B2 8/2006 Glaesner et al.
7,093,594 B2 8/2006 Harrison et al.
7,093,595 B2 8/2006 Nesbitt
D527,817 S 9/2006 Ziegler et al.
7,101,843 B2 9/2006 Glaesner et al.
7,101,866 B2 9/2006 Biggadike et al.
7,107,988 B2 9/2006 Pinon et al.
D529,604 S 10/2006 Young et al.
7,125,566 B2 10/2006 Etter
7,128,067 B2 10/2006 Byron et al.
7,131,441 B1 11/2006 Keller et al.
7,132,115 B2 11/2006 Musa et al.
7,140,365 B2 11/2006 Poole et al.
D533,268 S 12/2006 Olfati
7,143,764 B1 12/2006 Dagsland et al.
7,143,765 B2 12/2006 Asking et al.
7,144,863 B2 12/2006 DeFelippis et al.
7,146,978 B2 12/2006 Edwards et al.
7,151,456 B2 12/2006 Godfrey
7,163,014 B2 1/2007 Nichols et al.
D537,522 S 2/2007 Cox et al.
7,171,965 B2 2/2007 Young et al.
7,172,768 B2 2/2007 Hastedt et al.
7,179,788 B2 2/2007 DeFelippis et al.
D537,936 S 3/2007 Cox et al.
D538,423 S 3/2007 Berube et al.
7,185,650 B2 3/2007 Huber et al.
7,198,806 B2 4/2007 Berndt
7,211,557 B2 5/2007 DiMarchi et al.
7,219,664 B2 5/2007 Ruckdeschel et al.
7,223,728 B2 5/2007 Yakubu-Madus et al.
D544,093 S 6/2007 Eriksen
7,231,919 B2 6/2007 Giroux
7,232,897 B2 6/2007 Hotamisligil et al.
7,234,459 B2 6/2007 Del Bon
7,234,460 B2 6/2007 Greenleaf et al.
7,234,464 B2 6/2007 Goede et al.
7,238,663 B2 7/2007 DeFelippis et al.
7,246,617 B1 7/2007 Hammer et al.
D548,330 S 8/2007 Cox et al.
D548,618 S 8/2007 Ferguson et al.
D548,619 S 8/2007 Ferguson et al.
D548,833 S 8/2007 Young et al.
D549,111 S 8/2007 Ferguson et al.
7,258,118 B2 8/2007 Goede et al.
7,259,233 B2 8/2007 Dodd et al.
D550,835 S 9/2007 Tanaka et al.
7,270,124 B2 9/2007 Rasmussen
D552,729 S 10/2007 Cox et al.
7,276,534 B2 10/2007 Milstein
7,278,419 B2 10/2007 Gonda
7,278,426 B2 10/2007 Mryman et al.
7,278,843 B2 10/2007 Feldstein et al.
7,279,457 B2 10/2007 Pohl et al.
7,284,553 B2 10/2007 Hochrainer
D557,799 S 12/2007 Greenhalgh et al.
7,305,986 B1 12/2007 Steiner
7,306,787 B2 12/2007 Tarara et al.
D560,793 S 1/2008 Pearl et al.
7,314,859 B2 1/2008 Green et al.
7,316,748 B2 1/2008 Li et al.
7,331,340 B2 2/2008 Barney
7,334,577 B2 2/2008 Gumaste et al.
7,344,734 B2 3/2008 Heijerman et al.
7,368,102 B2 5/2008 Tarara et al.
7,373,938 B2 5/2008 Nichols et al.
7,377,277 B2 5/2008 Hickey et al.
7,387,122 B2 6/2008 Nishibayashi et al.
7,399,528 B2 7/2008 Caponetti et al.
7,401,713 B2 7/2008 Ede et al.
7,402,564 B1 7/2008 Schteingart et al.
7,414,720 B2 8/2008 Wachtel et al.
D577,815 S 9/2008 Gokhale et al.
7,422,013 B2 9/2008 Burr et al.
D579,549 S 10/2008 Birath et al.
7,448,375 B2 11/2008 Gonda et al.

(56) References Cited

U.S. PATENT DOCUMENTS 7,448,379 B2 11/2008 Yamashita et al.
7,451,761 B2 11/2008 Hickey et al.
7,453,556 B2 11/2008 Hochrainer et al.
D583,463 S 12/2008 Wood et al.
7,461,653 B2 12/2008 Oliva
7,462,367 B2 12/2008 Schmidt et al.
7,464,706 B2 12/2008 Steiner et al.
7,469,696 B2 12/2008 Yang et al.
7,500,479 B2 3/2009 Nichols et al.
7,503,324 B2 3/2009 Barney et al.
7,504,538 B2 3/2009 Chang et al.
7,517,874 B2 4/2009 Beckett et al.
7,520,278 B2 4/2009 Crowder et al.
7,521,069 B2 4/2009 Patton et al.
7,533,668 B1 5/2009 Widerstrom
D594,753 S 6/2009 Eadicicco et al.
7,556,798 B2 7/2009 Edwards et al.
7,559,322 B2 7/2009 Foley et al.
D597,418 S 8/2009 Stojek
D597,657 S 8/2009 Kinsey et al.
D598,785 S 8/2009 Stojek
7,584,846 B2 9/2009 Senter
7,598,222 B2 10/2009 Prouty, Jr. et al.
D604,832 S 11/2009 Smutney
D604,833 S 11/2009 Polidoro
D605,752 S 12/2009 Polidoro
D605,753 S 12/2009 Smutney
7,625,865 B2 12/2009 Colombo
7,648,960 B2 1/2010 Steiner et al.
D613,849 S 4/2010 Smutney
D614,045 S 4/2010 Gaudenzi et al.
D614,760 S 4/2010 Smutney et al.
7,694,676 B2 4/2010 Wachtel
7,708,014 B2 5/2010 Yamashita et al.
7,709,639 B2 5/2010 Stevenson
7,713,937 B2 5/2010 Schteingart et al.
7,727,963 B2 6/2010 Schteingart et al.
7,735,485 B2 6/2010 Yamashita et al.
D620,812 S 8/2010 Gaudenzi et al.
7,794,754 B2 9/2010 Feldstein et al.
7,799,344 B2 9/2010 Oberg
7,803,404 B2 9/2010 Hokenson
7,820,676 B2 * 10/2010 Leone-Bay .......... A61K 31/357
514/255.02
D628,090 S 11/2010 Stuiber et al.
7,833,549 B2 11/2010 Steiner et al.
7,833,550 B2 11/2010 Steiner et al.
7,842,662 B2 11/2010 Schteingart et al.
D629,505 S 12/2010 Adamo
D629,506 S 12/2010 Adamo
D629,886 S 12/2010 Adamo
D629,887 S 12/2010 Adamo
D629,888 S 12/2010 Adamo
D635,241 S 3/2011 McLean
D635,242 S 3/2011 Adamo
D635,243 S 3/2011 Kinsey
7,913,688 B2 3/2011 Cross
D636,867 S 4/2011 Polidoro et al.
D636,868 S 4/2011 Kinsey et al.
D636,869 S 4/2011 Laurenzi et al.
7,919,119 B2 4/2011 Straub et al.
7,943,178 B2 5/2011 Steiner et al.
7,943,572 B2 5/2011 Cheatham et al.
7,954,491 B2 6/2011 Hrkach
7,959,609 B2 6/2011 Gaydos et al.
D641,076 S 7/2011 Grunstad et al.
D643,308 S 8/2011 Bergey
D645,954 S 9/2011 Hately
D647,195 S 10/2011 Clarke et al.
D647,196 S 10/2011 Clarke et al.
8,037,880 B2 10/2011 Zhu et al.
8,037,881 B2 10/2011 Pentafragas
8,039,431 B2 10/2011 Wilson et al.
8,047,203 B2 11/2011 Young et al.
D652,322 S 1/2012 Stuiber et al.
8,109,267 B2 2/2012 Villax et al.
8,119,593 B2 2/2012 Richardson
D655,622 S 3/2012 Sadler et al.
8,133,514 B2 3/2012 Milstein
8,146,588 B2 4/2012 Steiner et al.
8,156,936 B2 4/2012 Steiner et al.
D659,020 S 5/2012 Kemner
D659,022 S 5/2012 Kemner
8,166,970 B2 5/2012 Poole et al.
8,172,817 B2 5/2012 Michaels et al.
8,196,576 B2 6/2012 Kriksunov et al.
8,201,555 B2 6/2012 Chawla
8,202,992 B2 6/2012 Stevenson
D664,640 S 7/2012 Smutney et al.
8,215,300 B2 7/2012 Steiner et al.
8,217,007 B1 7/2012 Schteingart et al.
8,227,409 B2 7/2012 Kraft
8,236,766 B2 8/2012 Schteingart et al.
8,252,916 B2 8/2012 Simard et al.
8,258,095 B2 9/2012 Boss et al.
8,278,308 B2 10/2012 Leone-Bay et al.
8,293,869 B2 10/2012 Bossard
8,314,106 B2 11/2012 Kraft
D671,842 S 12/2012 Bergey
D674,893 S 1/2013 Kinsey et al.
8,372,804 B2 2/2013 Richardson
8,377,869 B2 2/2013 Richardson
8,389,470 B2 3/2013 Steiner
8,394,414 B2 3/2013 Steiner et al.
8,408,200 B2 4/2013 Clark et al.
8,420,604 B2 4/2013 Hokenson
8,424,518 B2 4/2013 Smutney
8,485,180 B2 7/2013 Smutney et al.
8,486,894 B2 7/2013 Schteingart et al.
8,499,757 B2 8/2013 Smutney
8,512,932 B2 8/2013 Wilson et al.
8,522,775 B2 9/2013 Malhotra et al.
8,536,131 B2 9/2013 Schteingart et al.
8,538,707 B2 9/2013 Adamo et al.
8,539,946 B2 9/2013 Esteve et al.
8,551,528 B2 10/2013 Grant et al.
8,563,101 B2 10/2013 Spallek
8,636,001 B2 1/2014 Smutney
8,642,548 B2 2/2014 Richardson et al.
8,671,937 B2 3/2014 Steiner et al.
8,677,992 B2 3/2014 Villax
8,763,606 B2 7/2014 Mosier et al.
8,778,403 B2 7/2014 Grant et al.
8,783,249 B2 7/2014 Poole et al.
8,808,786 B2 8/2014 Jinks et al.
8,820,324 B2 9/2014 Smith et al.
8,909,487 B2 12/2014 Adamo et al.
8,925,726 B2 1/2015 Bergey
9,041,925 B2 5/2015 Adamo et al.
9,138,407 B2 9/2015 Caponetti et al.
9,278,902 B2 3/2016 Tang et al.
9,278,903 B2 3/2016 Tang et al.
9,289,388 B2 3/2016 Guarnieri
9,381,243 B2 7/2016 Johansson et al.
9,498,437 B2 11/2016 Chaudry
9,504,663 B2 11/2016 Freissmuth et al.
9,713,599 B2 7/2017 Wade
9,758,465 B2 9/2017 Laing
2001/0020147 A1 9/2001 Staniforth et al.
2001/0039442 A1 11/2001 Gorge et al.
2002/0000225 A1 1/2002 Schuler et al.
2002/0033177 A1 3/2002 Ohki et al.
2002/0052381 A1 5/2002 Bar-Or et al.
2002/0053344 A1 5/2002 Davies et al.
2002/0053347 A1 5/2002 Ziaee
2002/0065239 A1 5/2002 Caplan et al.
2002/0088462 A1 7/2002 Genova et al.
2002/0101590 A1 8/2002 Shimaoka
2002/0144680 A1 10/2002 Nilsson et al.
2002/0161001 A1 10/2002 Kanstrup et al.
2003/0000524 A1 1/2003 Andersson et al.
2003/0010794 A1 1/2003 Herdtle et al.
2003/0013641 A1 1/2003 Steiner et al.
2003/0017211 A1 1/2003 Steiner

(56) References Cited

U.S. PATENT DOCUMENTS

| | | | |
|---|---|---|---|
| 2003/0053960 | A1 | 3/2003 | Heijerman et al. |
| 2003/0064097 | A1 | 4/2003 | Patel et al. |
| 2003/0068378 | A1 | 4/2003 | Chen et al. |
| 2003/0099636 | A1 | 5/2003 | Epshtein et al. |
| 2003/0136405 | A1 | 7/2003 | Goede et al. |
| 2003/0194420 | A1 | 10/2003 | Holl et al. |
| 2003/0235538 | A1 | 12/2003 | Zirenberg |
| 2004/0024180 | A1 | 2/2004 | Drauz |
| 2004/0025875 | A1 | 2/2004 | Reber et al. |
| 2004/0034014 | A1 | 2/2004 | Kanstrup et al. |
| 2004/0038865 | A1 | 2/2004 | Gelber et al. |
| 2004/0053819 | A1 | 3/2004 | Dodd et al. |
| 2004/0062722 | A1 | 4/2004 | Gonda et al. |
| 2004/0076588 | A1 | 4/2004 | Batycky et al. |
| 2004/0077528 | A1 | 4/2004 | Steiner et al. |
| 2004/0096403 | A1 | 5/2004 | Steiner |
| 2004/0105819 | A1 | 6/2004 | Hale et al. |
| 2004/0107963 | A1 | 6/2004 | Finlay et al. |
| 2004/0121964 | A1 | 6/2004 | Madar et al. |
| 2004/0138099 | A1 | 7/2004 | Draeger |
| 2004/0151059 | A1 | 8/2004 | Robert, II et al. |
| 2004/0151774 | A1 | 8/2004 | Pauletti et al. |
| 2004/0157928 | A1 | 8/2004 | Kim et al. |
| 2004/0163648 | A1 | 8/2004 | Burton |
| 2004/0182387 | A1 | 9/2004 | Steiner et al. |
| 2004/0187869 | A1 | 9/2004 | Bjorndal et al. |
| 2004/0204439 | A1 | 10/2004 | Staniforth et al. |
| 2004/0204440 | A1 | 10/2004 | Staniforth et al. |
| 2004/0211419 | A1 | 10/2004 | Eason et al. |
| 2004/0234615 | A1 | 11/2004 | Sabetsky |
| 2004/0234616 | A1 | 11/2004 | Sabetsky |
| 2004/0241232 | A1 | 12/2004 | Brown et al. |
| 2004/0247628 | A1 | 12/2004 | Lintz et al. |
| 2004/0250812 | A1 | 12/2004 | Davies et al. |
| 2005/0000518 | A1 | 1/2005 | Dunkley et al. |
| 2005/0039743 | A1 | 2/2005 | Taylor |
| 2005/0043228 | A1 | 2/2005 | DeFelippis et al. |
| 2005/0043247 | A1 | 2/2005 | Trunk et al. |
| 2005/0056281 | A1 | 3/2005 | Snow |
| 2005/0070469 | A1 | 3/2005 | Bloom |
| 2005/0080000 | A1 | 4/2005 | Thurow et al. |
| 2005/0119604 | A1 | 6/2005 | Bonney et al. |
| 2005/0124644 | A1 | 6/2005 | Nilsson et al. |
| 2005/0147581 | A1 | 7/2005 | Zamiri et al. |
| 2005/0153874 | A1 | 7/2005 | Cheatham et al. |
| 2005/0155601 | A1 | 7/2005 | Steiner et al. |
| 2005/0183723 | A1 | 8/2005 | Pinon et al. |
| 2005/0187749 | A1 | 8/2005 | Singley |
| 2005/0214251 | A1 | 9/2005 | Pohl et al. |
| 2005/0252508 | A1 | 11/2005 | Koerner |
| 2005/0265927 | A1 | 12/2005 | Lee |
| 2005/0274378 | A1 | 12/2005 | Bonney et al. |
| 2006/0000469 | A1 | 1/2006 | Tseng |
| 2006/0003316 | A1 | 1/2006 | Simard et al. |
| 2006/0040953 | A1 | 2/2006 | Leone-Bay et al. |
| 2006/0041133 | A1 | 2/2006 | Stevenson et al. |
| 2006/0099269 | A1 | 5/2006 | Cheatham et al. |
| 2006/0120969 | A1 | 6/2006 | Nilsson et al. |
| 2006/0153778 | A1 | 7/2006 | Gelber et al. |
| 2006/0160722 | A1 | 7/2006 | Green et al. |
| 2006/0165756 | A1 | 7/2006 | Catani et al. |
| 2006/0239933 | A1 | 10/2006 | Nilsson et al. |
| 2006/0239934 | A1 | 10/2006 | Cheatham et al. |
| 2006/0243275 | A1 | 11/2006 | Ruckdeschel et al. |
| 2006/0249419 | A1 | 11/2006 | Taylor et al. |
| 2006/0260777 | A1 | 11/2006 | Rashba-Step et al. |
| 2006/0283758 | A1 | 12/2006 | Pasbrig |
| 2007/0006876 | A1 | 1/2007 | Finlay et al. |
| 2007/0017506 | A1 | 1/2007 | Bell et al. |
| 2007/0020191 | A1 | 1/2007 | Boss et al. |
| 2007/0027063 | A1 | 2/2007 | Boss et al. |
| 2007/0044793 | A1 | 3/2007 | Kleinstreuer et al. |
| 2007/0049576 | A1 | 3/2007 | Barlow et al. |
| 2007/0059373 | A1 | 3/2007 | Oberg |
| 2007/0059374 | A1 | 3/2007 | Hokenson et al. |
| 2007/0074989 | A1 | 4/2007 | Merboth et al. |
| 2007/0077219 | A1 | 4/2007 | Fahl et al. |
| 2007/0086952 | A1 | 4/2007 | Steiner |
| 2007/0099454 | A1 | 5/2007 | Gordon |
| 2007/0111983 | A1 | 5/2007 | Fong |
| 2007/0125375 | A1 | 6/2007 | Finlay et al. |
| 2007/0128193 | A1 | 6/2007 | O'Neil et al. |
| 2007/0151562 | A1 | 7/2007 | Jones |
| 2007/0191462 | A1 | 8/2007 | Hettiarachchi |
| 2007/0196503 | A1 | 8/2007 | Wilson et al. |
| 2007/0207958 | A1 | 9/2007 | Bridon et al. |
| 2007/0225587 | A1 | 9/2007 | Burnell et al. |
| 2007/0235029 | A1 | 10/2007 | Zhu et al. |
| 2007/0240708 | A1 | 10/2007 | Schuckmann |
| 2007/0272763 | A1 | 11/2007 | Dunne et al. |
| 2007/0277820 | A1 | 12/2007 | Crowder et al. |
| 2007/0277821 | A1 | 12/2007 | Oliva et al. |
| 2007/0295332 | A1 | 12/2007 | Ziegler |
| 2007/0299074 | A1 | 12/2007 | Netz et al. |
| 2008/0008764 | A1 | 1/2008 | Milstein |
| 2008/0015457 | A1 | 1/2008 | Silva |
| 2008/0047550 | A2 | 2/2008 | Steiner et al. |
| 2008/0066739 | A1 | 3/2008 | LeMahieu et al. |
| 2008/0108554 | A1 | 5/2008 | Jackson et al. |
| 2008/0108574 | A1 | 5/2008 | Barlow et al. |
| 2008/0115785 | A1 | 5/2008 | Eason et al. |
| 2008/0127970 | A1 | 6/2008 | Steiner et al. |
| 2008/0127974 | A1 | 6/2008 | Lastow |
| 2008/0129791 | A1 | 6/2008 | King et al. |
| 2008/0168987 | A1 | 7/2008 | Denny et al. |
| 2008/0190424 | A1 | 8/2008 | Lucking et al. |
| 2008/0197044 | A1 | 8/2008 | Hickey et al. |
| 2008/0200449 | A1 | 8/2008 | Olschewski et al. |
| 2008/0216824 | A1 | 9/2008 | Ooida |
| 2008/0217199 | A1 | 9/2008 | Burress et al. |
| 2008/0226736 | A1 | 9/2008 | Caponetti et al. |
| 2008/0255468 | A1 | 10/2008 | Derchak et al. |
| 2008/0260838 | A1 | 10/2008 | Hokenson et al. |
| 2008/0260840 | A1 | 10/2008 | Alessi |
| 2008/0295833 | A1 | 12/2008 | Rohrschneider et al. |
| 2008/0314384 | A1 | 12/2008 | Harris et al. |
| 2008/0319333 | A1 | 12/2008 | Gavish et al. |
| 2009/0025720 | A1 | 1/2009 | Chen |
| 2009/0036465 | A1 | 2/2009 | Roscigno et al. |
| 2009/0068274 | A1 | 3/2009 | Edwards et al. |
| 2009/0084379 | A1 | 4/2009 | Goeckner et al. |
| 2009/0084380 | A1 | 4/2009 | Gieschen et al. |
| 2009/0134051 | A1 | 5/2009 | Rapp et al. |
| 2009/0149727 | A1 | 6/2009 | Truitt et al. |
| 2009/0151720 | A1 | 6/2009 | Inoue et al. |
| 2009/0178676 | A1 | 7/2009 | Villax et al. |
| 2009/0205657 | A1 | 8/2009 | Barney et al. |
| 2009/0209502 | A1 | 8/2009 | Haeberlin et al. |
| 2009/0232891 | A1 | 9/2009 | Gelber et al. |
| 2009/0241949 | A1 | 10/2009 | Smutney |
| 2009/0250058 | A1 | 10/2009 | Lastow |
| 2009/0258818 | A1 | 10/2009 | Surolia et al. |
| 2009/0314292 | A1 | 12/2009 | Overfield |
| 2009/0320837 | A1 | 12/2009 | Smith et al. |
| 2010/0012120 | A1 | 1/2010 | Herder |
| 2010/0048693 | A1 | 2/2010 | Geraci et al. |
| 2010/0086609 | A1 | 4/2010 | Steiner et al. |
| 2010/0113363 | A1 | 5/2010 | Holst et al. |
| 2010/0163042 | A1 | 7/2010 | Bhowmick et al. |
| 2010/0180894 | A1 | 7/2010 | Jones et al. |
| 2010/0181225 | A1 | 7/2010 | Spallek et al. |
| 2010/0190701 | A1 | 7/2010 | Day et al. |
| 2010/0193380 | A1 | 8/2010 | Sullivan et al. |
| 2010/0197565 | A1 | 8/2010 | Smutney et al. |
| 2010/0212667 | A1 | 8/2010 | Smith et al. |
| 2010/0235116 | A1 | 9/2010 | Adamo et al. |
| 2010/0238457 | A1 | 9/2010 | Adamo et al. |
| 2010/0278924 | A1 | 11/2010 | Oberg |
| 2010/0288276 | A1 | 11/2010 | Ganderton et al. |
| 2010/0326438 | A1 | 12/2010 | Dunne |
| 2011/0000482 | A1 | 1/2011 | Gumaste et al. |
| 2011/0003004 | A1 | 1/2011 | Hokenson |
| 2011/0011394 | A1 | 1/2011 | Edwards et al. |
| 2011/0083667 | A1 | 4/2011 | Briant |

(56) References Cited

U.S. PATENT DOCUMENTS

| | | | |
|---|---|---|---|
| 2011/0158935 | A1 | 6/2011 | Kraft |
| 2011/0183901 | A1 | 7/2011 | Cheatham |
| 2012/0014999 | A1 | 1/2012 | Grant et al. |
| 2012/0040899 | A1 | 2/2012 | Costello |
| 2012/0071510 | A1 | 3/2012 | Leone-Bay et al. |
| 2012/0094905 | A1 | 4/2012 | Costello |
| 2012/0115777 | A1 | 5/2012 | Richardson |
| 2012/0122775 | A1 | 5/2012 | Boss et al. |
| 2012/0160241 | A1 | 6/2012 | Oliva |
| 2012/0164186 | A1 | 6/2012 | Grant et al. |
| 2012/0177693 | A1 | 7/2012 | Cipolla et al. |
| 2012/0178935 | A1 | 7/2012 | Stevenson |
| 2012/0192865 | A1 | 8/2012 | Steiner et al. |
| 2012/0207913 | A1 | 8/2012 | Smyth |
| 2012/0240929 | A1 | 9/2012 | Steiner et al. |
| 2012/0247235 | A1 | 10/2012 | Adamo et al. |
| 2012/0247465 | A1 | 10/2012 | Wachtel |
| 2012/0328676 | A1 | 12/2012 | Leone-Bay et al. |
| 2013/0012710 | A1 | 1/2013 | Freeman et al. |
| 2013/0039847 | A1 | 2/2013 | Gessler et al. |
| 2013/0040898 | A1 | 2/2013 | Johansson |
| 2013/0053309 | A1 | 2/2013 | Kraft |
| 2013/0104887 | A1 | 5/2013 | Smutney et al. |
| 2013/0118491 | A1 | 5/2013 | Richardson et al. |
| 2013/0125886 | A1 | 5/2013 | Richardson et al. |
| 2013/0143801 | A1 | 6/2013 | Steiner et al. |
| 2013/0189365 | A1 | 7/2013 | Hokenson |
| 2013/0199527 | A1 | 8/2013 | Smutney et al. |
| 2013/0261177 | A1 | 10/2013 | Johansson et al. |
| 2013/0289278 | A1 | 10/2013 | Kraft |
| 2013/0291866 | A1 | 11/2013 | Smutney |
| 2013/0291867 | A1 | 11/2013 | Smutney |
| 2013/0303445 | A1 | 11/2013 | Wilson et al. |
| 2013/0338065 | A1 | 12/2013 | Smutney |
| 2014/0007873 | A1 | 1/2014 | Smutney |
| 2014/0014106 | A1 | 1/2014 | Smutney |
| 2014/0044797 | A1 | 2/2014 | Johansson et al. |
| 2014/0083421 | A1 | 3/2014 | Smutney |
| 2014/0096771 | A1 | 4/2014 | Remmelgas et al. |
| 2014/0100158 | A1 | 4/2014 | Richardson et al. |
| 2014/0187490 | A1 | 7/2014 | Richardson et al. |
| 2014/0199398 | A1 | 7/2014 | Grant et al. |
| 2014/0227359 | A1 | 8/2014 | Leone-Bay et al. |
| 2014/0243530 | A1 | 8/2014 | Stevenson et al. |
| 2014/0271888 | A1 | 9/2014 | Grant et al. |
| 2014/0290654 | A1 | 10/2014 | Poole et al. |
| 2014/0302151 | A1 | 10/2014 | Leone-Bay et al. |
| 2014/0308358 | A1 | 10/2014 | Oberg et al. |
| 2014/0315953 | A1 | 10/2014 | Leone-Bay et al. |
| 2015/0031609 | A1 | 1/2015 | Steiner et al. |
| 2015/0045295 | A1 | 2/2015 | Smutney et al. |
| 2015/0052977 | A1 | 2/2015 | Adamo et al. |
| 2015/0057325 | A1 | 2/2015 | Johansson et al. |
| 2015/0065422 | A1 | 3/2015 | Kraft |
| 2015/0080298 | A1 | 3/2015 | Costello et al. |
| 2015/0108023 | A1 | 4/2015 | Bergey |
| 2015/0122258 | A1 | 5/2015 | Steiner et al. |
| 2015/0150980 | A1 | 6/2015 | Leone-Bay et al. |
| 2015/0174210 | A1 | 6/2015 | Boss et al. |
| 2015/0196516 | A1 | 7/2015 | Yacoub et al. |
| 2015/0196724 | A1 | 7/2015 | Adamo et al. |
| 2015/0226656 | A1 | 8/2015 | Adamo et al. |
| 2015/0231067 | A1 | 8/2015 | Mann |
| 2015/0246188 | A1 | 9/2015 | Steiner et al. |
| 2015/0283069 | A1 | 10/2015 | Smutney et al. |
| 2015/0283213 | A1 | 10/2015 | Costello et al. |
| 2015/0290132 | A1 | 10/2015 | Gelber et al. |
| 2015/0359744 | A1 | 12/2015 | Hokenson et al. |
| 2016/0175319 | A1 | 6/2016 | Freissmuth et al. |

FOREIGN PATENT DOCUMENTS

| | | | |
|---|---|---|---|
| CN | 101851213 | | 10/2010 |
| DE | 2840442 | C2 | 2/1982 |
| DE | 3639836 | A1 | 6/1988 |
| DE | 19519840 | A1 | 12/1996 |
| EP | 69715 | | 1/1983 |
| EP | 122036 | | 10/1984 |
| EP | 143524 | | 6/1985 |
| EP | 180543 | | 5/1986 |
| EP | 220958 | | 5/1987 |
| EP | 237507 | | 8/1987 |
| EP | 257915 | | 2/1988 |
| EP | 308637 | A1 | 3/1989 |
| EP | 360340 | | 3/1990 |
| EP | 364235 | | 4/1990 |
| EP | 387222 | A | 9/1990 |
| EP | 388621 | A | 9/1990 |
| EP | 606486 | | 12/1993 |
| EP | 581473 | A1 | 2/1994 |
| EP | 655237 | | 5/1995 |
| EP | 666085 | A1 | 8/1995 |
| EP | 748213 | | 12/1996 |
| EP | 558879 | B1 | 5/1997 |
| EP | 844007 | | 12/1998 |
| EP | 1060741 | A1 | 12/2000 |
| EP | 1114644 | | 7/2001 |
| EP | 640354 | B1 | 12/2001 |
| EP | 1364967 | | 11/2003 |
| EP | 825885 | B1 | 3/2004 |
| EP | 96911738 | | 6/2004 |
| EP | 1598066 | | 11/2005 |
| EP | 833652 | B1 | 2/2008 |
| EP | 1923087 | A2 | 5/2008 |
| EP | 2060268 | A1 | 5/2009 |
| EP | 2314298 | A1 | 4/2011 |
| GB | 475440 | A | 11/1937 |
| GB | 716815 | | 10/1954 |
| GB | 2072536 | A | 10/1981 |
| GB | 2148841 | A | 6/1985 |
| GB | 2240337 | | 7/1991 |
| GB | 2253200 | A | 9/1992 |
| GB | 2262452 | | 6/1993 |
| GB | 2398065 | A | 8/2004 |
| JP | 63-020301 | | 1/1988 |
| JP | 2115154 | A | 4/1990 |
| JP | 2-149545 | | 2/1992 |
| JP | H07-041428 | | 2/1995 |
| JP | 09-208485 | | 8/1997 |
| JP | 10234827 | A | 9/1998 |
| JP | 2002322294 | | 11/2002 |
| JP | 2003-503420 | | 1/2003 |
| JP | 2004-121061 | | 4/2004 |
| JP | 2006-280620 | A | 10/2006 |
| JP | 2007-061281 | | 3/2007 |
| TW | 200505517 | A | 2/2005 |
| WO | 1990/013285 | | 11/1990 |
| WO | 1991/004011 | | 4/1991 |
| WO | 1991/006287 | | 5/1991 |
| WO | 1991/016038 | | 10/1991 |
| WO | 1991/016882 | | 11/1991 |
| WO | 1991/019524 | | 12/1991 |
| WO | 1992/004069 | | 3/1992 |
| WO | 1992/008509 | | 5/1992 |
| WO | 1993/002712 | | 2/1993 |
| WO | 1993/014110 | | 7/1993 |
| WO | 1993/017728 | | 9/1993 |
| WO | 1993/018754 | A1 | 9/1993 |
| WO | 1994/000291 | | 1/1994 |
| WO | 1994/008552 | | 4/1994 |
| WO | 1994/008599 | | 4/1994 |
| WO | 1994/019041 | | 9/1994 |
| WO | 1994/023702 | | 10/1994 |
| WO | 1994/025005 | A1 | 11/1994 |
| WO | 1995/000127 | A1 | 1/1995 |
| WO | 1995/005208 | | 2/1995 |
| WO | 1995/011666 | | 5/1995 |
| WO | 1995/024183 | A1 | 9/1995 |
| WO | 1995/031979 | | 11/1995 |
| WO | 1995/034294 | | 12/1995 |
| WO | 1996/001105 | | 1/1996 |
| WO | 1996/005810 | | 2/1996 |
| WO | 1996/013250 | | 5/1996 |
| WO | 1996/022802 | A | 8/1996 |

(56) References Cited

FOREIGN PATENT DOCUMENTS

| | | | | |
|---|---|---|---|---|
| WO | 1996/027386 | A1 | 9/1996 |
| WO | 1996/032149 | | 10/1996 |
| WO | 1996/036314 | | 11/1996 |
| WO | 1996/036317 | A1 | 11/1996 |
| WO | 1996/040206 | A1 | 12/1996 |
| WO | 1997/001365 | | 1/1997 |
| WO | 1997/004747 | | 2/1997 |
| WO | 1997/025086 | A2 | 7/1997 |
| WO | 1997/030743 | | 8/1997 |
| WO | 1997/035562 | A1 | 10/1997 |
| WO | 1997/046206 | | 12/1997 |
| WO | 1997/049386 | | 12/1997 |
| WO | 1998/026827 | A1 | 6/1998 |
| WO | 1998/039043 | | 9/1998 |
| WO | 1998/041255 | A2 | 9/1998 |
| WO | 1998/043615 | | 10/1998 |
| WO | 1999/014239 | A1 | 3/1999 |
| WO | 1999/018939 | A1 | 4/1999 |
| WO | 1999/032510 | A1 | 7/1999 |
| WO | 1999/033862 | | 7/1999 |
| WO | 1999/052506 | | 10/1999 |
| WO | 2000/12116 | | 3/2000 |
| WO | 2000/033811 | A2 | 6/2000 |
| WO | 2000/059476 | A1 | 10/2000 |
| WO | 2000/071154 | A2 | 11/2000 |
| WO | 2001/000654 | | 1/2001 |
| WO | 2001/081321 | A | 1/2001 |
| WO | 2001/049274 | A2 | 7/2001 |
| WO | 2001/051071 | | 7/2001 |
| WO | 2001/052813 | A1 | 7/2001 |
| WO | 2001/066064 | | 9/2001 |
| WO | 2001/068169 | | 9/2001 |
| WO | 2001/097886 | A1 | 12/2001 |
| WO | 2001/007107 | | 2/2002 |
| WO | 2002/011676 | | 2/2002 |
| WO | 2002/012201 | A1 | 2/2002 |
| WO | 2002/047659 | A2 | 6/2002 |
| WO | 2002/058735 | | 8/2002 |
| WO | 2002/059574 | A1 | 8/2002 |
| WO | 2002/067995 | A1 | 9/2002 |
| WO | 2002/085281 | | 10/2002 |
| WO | 2002/098348 | | 12/2002 |
| WO | 2002/102444 | | 12/2002 |
| WO | 2003/000202 | | 1/2003 |
| WO | 2003/022304 | A1 | 3/2003 |
| WO | 2003/055547 | A1 | 7/2003 |
| WO | 2003/057170 | | 7/2003 |
| WO | 2003/061578 | A2 | 7/2003 |
| WO | 2003/072195 | A2 | 9/2003 |
| WO | 2003/080149 | A2 | 10/2003 |
| WO | 2003/086345 | | 10/2003 |
| WO | 2003/094951 | | 11/2003 |
| WO | 2004/012672 | | 2/2004 |
| WO | 2004/012720 | | 2/2004 |
| WO | 2004/033010 | | 4/2004 |
| WO | 2004/035121 | | 4/2004 |
| WO | 2004/041338 | | 5/2004 |
| WO | 2004/050152 | | 6/2004 |
| WO | 2004/054647 | A1 | 7/2004 |
| WO | 2004/056314 | | 7/2004 |
| WO | 2004/060458 | | 7/2004 |
| WO | 2004/064862 | | 8/2004 |
| WO | 2004/075919 | | 9/2004 |
| WO | 2004/080401 | | 9/2004 |
| WO | 2004/080482 | | 9/2004 |
| WO | 2004/103304 | A2 | 12/2004 |
| WO | 2005/020964 | | 3/2005 |
| WO | 2005/023348 | A | 3/2005 |
| WO | 2005/028699 | A1 | 3/2005 |
| WO | 2005/067964 | | 7/2005 |
| WO | 2005/081977 | A2 | 9/2005 |
| WO | 2005/089722 | | 9/2005 |
| WO | 2005/089843 | | 9/2005 |
| WO | 2005/102428 | A1 | 11/2005 |
| WO | 2005/102429 | | 11/2005 |
| WO | 2005/113042 | A1 | 12/2005 |
| WO | 2005/113043 | | 12/2005 |
| WO | 2005/120616 | | 12/2005 |
| WO | 2006/010248 | | 2/2006 |
| WO | 2006/017688 | A2 | 2/2006 |
| WO | 2006/023849 | | 3/2006 |
| WO | 2006/023943 | | 3/2006 |
| WO | 2006/023944 | | 3/2006 |
| WO | 2006/037636 | | 4/2006 |
| WO | 2006/059939 | | 6/2006 |
| WO | 2006/061637 | A2 | 6/2006 |
| WO | 2006/086107 | A2 | 8/2006 |
| WO | 2006/090149 | | 8/2006 |
| WO | 2006/105501 | | 10/2006 |
| WO | 2007/007110 | A1 | 1/2007 |
| WO | 2007/016600 | A2 | 2/2007 |
| WO | 2007/019229 | | 2/2007 |
| WO | 2007/024953 | A1 | 3/2007 |
| WO | 2007/030706 | | 3/2007 |
| WO | 2007/033316 | | 3/2007 |
| WO | 2007/033372 | A2 | 3/2007 |
| WO | 2007/042822 | | 4/2007 |
| WO | 2007/068896 | | 6/2007 |
| WO | 2007/075534 | A2 | 7/2007 |
| WO | 2007/093310 | | 8/2007 |
| WO | 2007/098500 | | 8/2007 |
| WO | 2007/100535 | | 9/2007 |
| WO | 2007/118342 | | 10/2007 |
| WO | 2007/118343 | A1 | 10/2007 |
| WO | 2007/121411 | | 10/2007 |
| WO | 2007/132217 | | 11/2007 |
| WO | 2007/144607 | | 12/2007 |
| WO | 2007/144614 | | 12/2007 |
| WO | 2008/001744 | | 1/2008 |
| WO | 2008/008021 | | 1/2008 |
| WO | 2008/014613 | A1 | 2/2008 |
| WO | 2008/020217 | | 2/2008 |
| WO | 2008/060484 | A2 | 5/2008 |
| WO | 2008/092864 | | 8/2008 |
| WO | 2008/110809 | | 9/2008 |
| WO | 2009/005546 | A1 | 1/2009 |
| WO | 2009/008001 | A2 | 1/2009 |
| WO | 2009/009013 | A2 | 1/2009 |
| WO | 2009/047281 | A1 | 4/2009 |
| WO | 2009/055030 | | 4/2009 |
| WO | 2009/055740 | | 4/2009 |
| WO | 2009/055742 | | 4/2009 |
| WO | 2009/095684 | A1 | 8/2009 |
| WO | 2009/121020 | A1 | 10/2009 |
| WO | 2009/140587 | A1 | 11/2009 |
| WO | 2009/152477 | A2 | 12/2009 |
| WO | 2009/155581 | A1 | 12/2009 |
| WO | 2010/021879 | A2 | 2/2010 |
| WO | 2010/078373 | A1 | 7/2010 |
| WO | 2010/080964 | | 7/2010 |
| WO | 2010/102148 | | 9/2010 |
| WO | 2010/105094 | A1 | 9/2010 |
| WO | 2010/108046 | A1 | 9/2010 |
| WO | 2010/125103 | A1 | 11/2010 |
| WO | 2010/144785 | A2 | 12/2010 |
| WO | 2010/144789 | | 12/2010 |
| WO | 2011/017554 | A2 | 2/2011 |
| WO | 2011/056889 | A1 | 5/2011 |
| WO | 2011/163272 | | 12/2011 |
| WO | 2012/064892 | A1 | 5/2012 |
| WO | 2012107364 | A1 | 8/2012 |
| WO | 2012/135765 | | 10/2012 |
| WO | 2012/174472 | A1 | 12/2012 |
| WO | 2012/174556 | A1 | 12/2012 |
| WO | 2013/063160 | A1 | 5/2013 |
| WO | 2014/012069 | A2 | 1/2014 |
| WO | 2014/036323 | A1 | 3/2014 |
| WO | 2014/066856 | A1 | 5/2014 |
| WO | 2014085813 | A1 | 6/2014 |
| WO | 2014/0144895 | A1 | 9/2014 |
| WO | 2015/010092 | A1 | 1/2015 |
| WO | 2015/021064 | A1 | 2/2015 |
| WO | 2015138423 | A1 | 9/2015 |

(56) References Cited

FOREIGN PATENT DOCUMENTS

| | | | |
|---|---|---|---|
| WO | 2015/148905 | A1 | 10/2015 |
| WO | 2016120311 | A1 | 8/2016 |
| WO | 2017192993 | A1 | 11/2017 |

OTHER PUBLICATIONS

Shields, Irritable bowel syndrome, archived Jun. 21, 2009, available at: https://web.archive.org/web/200906211 00502/http://www.gastroenterologistpaloalto.com/conditions-diseases-irritable-bowelsyndrome-palo-alto-ca. html; on Aug. 26, 2015 is U.S. Appl. No. 14/139,714.
Smith et al., Evaluation of novel aerosol formulations designed for mucosal vaccination against infleunza virus. Vacine, vol. 21, pp. 2805-2812 (2003).
U.S. Appl. No. 14/873,041, filed Oct. 1, 2015.
Design U.S. Appl. No. 29/504,212, filed Oct. 2, 2014.
U.S. Appl. No. 14/863,136, filed Sep. 23, 2015.
Young et al., Encapsulation of lysozyme in a biodegradable polymer by preparation with a vapor-over-liquid antisolvent. Journal of Pharmaceutical Sciences, 88:640-650 (1999).
Hazard Prevention and Control in the Work Environment: Airborne Dust WHO/SDE/OEH/99. 14 Chapter 1—Dust: Definitions and Concepts [retrieved from internet by Examiner in European case on Sep. 22, 2015]. <URL: http://www.who.int/occupational_health/publications/airdust/en/> published on Oct. 29, 2004 as per Wayback Machine.
Owens et al., Blood glucose self-monitoring in type 1 and type 2 diabetes: reaching a multidisciplinary consensus. Diabetes and Primary Care, vol. 6, No. 1, pp. 8-16 (2004).
Bilheimer DW, Ren H, Boss AH. Analysis of cardiovascular adverse events in patients with type 1 or type 2 diabetes enrolled in selected therapeutic trials in the phase 2/3 Technosphere® insulin development program. ADA 2011. Poster 922-P.
Billings CC, Smutney CC, Howard CP, et al. Handleability and characterization of inhalation profiles using the Gen2 delivery system in a pediatric population. Diabetes Technology Meeting 2010; poster.
Biodel's Intellecutal Property position strengthened for ultra-rapid-acting insulin programs by notice of intent to grant from European Patent Office. Newswire Feed, published May 2, 2012.
Blazquez E et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Boer et al., Design and application of a new modular adapter for laser diffraction characterization of inhalation aerosols. International Jornal of Pharmaceutics 249, pp. 233-245 (2002).
Boer et al., Inhalation characteristics and their effects on in vitro drug delivery from dry powder inhalers. Part 1. Inhalation characteristics, work of breathing and volunteers' preference in dependence of the inhaler resistance. Int. J. Pharm. 130 (1996) 231-244.
Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Bonner-Weir S et al. "New sources of pancreatic beta-cells." Nat Biotechnol 23:857-61, 2005.
Boss AH et al. "Inhaled Technosphere®/Insulin: Glucose elimination at the right time?" Poster presented at the American Diabetes Association 65th Scientific Sessions, Jun. 2005, abstract 443-P.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Does kinetics matter? Physiological consequences of the ability of Technosphere®/Insulin inhalation to mimic first phase insulin release." Presented at the 5th Annual Meeting of the Diabetes Technology Society, Nov. 2005, abstract A14.
Boss AH et al. "Markedly reduced post prandial glucose excursions through inhaled Technosphere®/Insulin in comparison to SC injected regular insulin in subjects with type 2 diabetes." 1st Annual Meeting of the European Association for the Study of Diabetes, Sep. 2005, abstract 816.
Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.
Boss et al. "Prandial Insulin: Is Inhaled Enough?" Drug Development Research 69(3):138-142 (2008).
Boss A H, Petrucci R, Lorber D. Coverage of prandial insulin requirements by means of an ultra-rapid-acting inhaled insulin. Journal of diabetes science and technology 2012;6:773-779.
Boss AH, Baughman RA, Evans SH, et al. A 3 month comparison in type 1 diabetes of inhaled Technosphere®/Insulin (TI) to Sc administered rapid-acting insulin analogue (RAA) as prandial insulin in a basal/prandial regimen. Diabetes 2006; 55:A97.
Boss AH, Evans SH, Firsov I, et al. Technosphere® insulin as effective as sc rapid acting insulin analogue in providing glycemic control in a 6-month study of patients with type 2 diabetes. Diabetes Technology Meeting 2006; poster.
Boss AH, Evans, SH, Ren, H, et al. Superior post prandial glucose control in patients with type 1 diabetes when using prandial technosphere insulin compared to NovoLog. Diabetologia 2006; Abstract 181.
Boss AH, Marino MT, Cassidy JP, et al. C-peptide correction method to determine exogenous insulin levels in pharmacokinetic studies using Technosphere® insulin. Diabetologia 2009; 52 (suppl 1).
Boss AH, Raskin P, Philips M, et al. Glycosylated hemoglobin and hypoglycaemia in patients with Type 2 diabetes mellitus: Technosphere® insulin and usual antihyperglycaemic regimen vs usual antihyperglycaemic regimen. Diabetologia 2010;53(suppl 1).
Brandt D, Boss AH. The next generation insulin therapy. OndrugDelivery 2006 (published online).
Grange et al., "Insulin Structure and Stability", Pharm Biotechnol, 5:315-50 (1993).
Bray "Exanatide" Am J Health-Sys Pharm 63:411, 2006.
Brownlee et al. "Glycemic variability: a hemoglobin A1c-independent risk factor for diabetic complications." JAMA 295:1707,2006.
Bruce, D.G., et al. "Physiological importance of deficiency of early prandial insulin secretion in non-insulin-dependent diabetes." Diabetes 37:736-44, 1988.
Bullock BP et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.
Calles-Escandon, J. and Robbins, D.C. "Loss of early phase insulin release in humans impairs glucose tolerance and blunts thermic effect of glucose." Diabetes 36:1167-72, 1987.
Camilleri, Clinical Practice: Diabetic Gastroparesis. The New England Journal of Medicine, 356: 820-829 (2007).
Campos et al. "Divergent tissue-specific and developmental expression of receptors for glucagon and glucagon0like peptide-1 in the mouse." Endocrinology 134:2156, 1994.
Cassidy J P, Amin N, Marino M, et al. Insulin lung deposition and clearance following Technosphere® insulin inhalation powder administration. Pharmaceutical Research 2011; 28:2157-2164.
Cassidy J, Amin N, Baughman R, et al. Insulin kinetics following Technosphere® insulin inhalation powder administration unchanged in albuterol-treated asthmatics. ADA 2010; Poster 522.

(56) References Cited

OTHER PUBLICATIONS

Cassidy J, Baughman RA, Tonelli G, et al. Use of rapid acting insulin analog as the baseline infusion during glucose clamping improves pharmacokinetic evaluation. ADA 2007; 56: Abstract 602-P.
Cassidy JP, Baughman RA, Schwartz SL, et al. AFRESA® (Technosphere® insulin) dosage strengths are interchangeable ADA 2009; Poster 433.
Cassidy JP, Marino MT, Amin N, et al. Lung deposition and absorption of insulin from AFRESA® (Technosphere® insulin) ADA 2009; Poster 425.
Cassidy JP, Potocka E, Baughman RA, et al. Pharmacokinetic characterization of the Technosphere® inhalation platform Diabetes Technology Meeting 2009. poster.
Caumo et al. "First-phase insulin secretion: does it exist in real life" Considerations on shape and function. Am J Physiol Endocrinol Metab 287:E371-E385, 2004.
Cefalu "Concept, Strategies and Feasibility of Noninvasive Insulin Delivery." Diabetes Care 27:239-246, 2004.
Cefalu "Novel routes of insulin delivery for patients with type 1 or type 2 diabetes." Ann Med 33:579-586, 2001.
Cefalu et al., Inhaled human insulin treatment in patients with type 2 diabetes mellitus. Ann. Int. Med., 2001, 134(3):203-207.
Ceglia et al. "Meta-analysis: efficacy and safety of inhaled insulin therapy in adults with diabetes mellitus." Ann Intern Med 145:665, 2006.
Cerasi, et al. Decreased sensitivity of the pancreatic beta cells to glucose in prediabetic and diabetic subjects. A glucose dose-response study. Diabetes 21(4):224-34, 1972.
Cernea et al. "Dose-response relationship of oral insulin spray in healthy subjects." Diabetes Care 28:1353-1357, 2005.
Cernea et al. "Noninjectable Methods of Insulin Administration." Drugs of Today 2006, 42 (6): 405-424.
Chan et al., "Pharmacological Management of Type 2 Diabetes Mellitus: Rationale for Rational Use of Insulin", Mayo Clin Proc, 2003, 78, 459-467.
Chase et al., "Redefining the clinical remission period in children with type 1 diabetes", Pediatric Diabetes, 2004, 5, 16-19.
Cheatham et al. "Desirable Dynamics & Performance of Inhaled Insulin Compared to Subcutaneous Insulin Given at Mealtime in Type 2 Diabetes: A Report from the Technosphere/Insulin Study Group." Diabetes Technology and Therapeutics, vol. 6, p. 234 (2004).
Cheatham et al. "A novel pulmonary insulin formulation replicates first phase insulin release and reduces s-proinsulin levels." Presented at the American Diabetes Association 64th Scientific Sessions, Jun. 2004, abstract 457-P.
Standl et al. "Good Glycemic Control With Flexibility in Timing of Basal Insulin Supply." Diabetes Care, vol. 28, No. 2, Feb. 2005.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement 1, Abstract 1545-PO, A368, 2000.
Steiner et al. "Bioavailability and pharmacokinetic properties of inhaled dry powder Technosphere®/Insulin" Diabetes 49 Supplement, May 2000, A126.
Steiner et al. "Technosphere®, a novel drug delivery system for oral administration of calcitonin." Pharmaceutical Res 11:S299, 1994.
Steiner et al. Technosphere(TM)/Insulin—proof of concept study with a new insulin formulation for pulmonary delivery. Exp Clin Endocrinol Diabetes, 110:17-21, 2002.
Steiner, K. et al. "The relative importance of first- and second-phase insulin secretion in countering the action of glucagon on glucose turnover in the conscious dog." Diabetes 31:964-972, 1982.
Steiner S, Rave K, Heise T, et al. Pharmacokinetic properties and bioavailablility of inhaled drug powder Technosphere™/insulin. Exp Clin Endocrinol Diabetes 2000; 108:S161.
Steiner S, Rave K, Heise T, et al. Technosphere™/insulin: Bioavailability and pharmacokinetic properties in healthy volunteers. Diabetologia 2000;43:Abstract 511-P.
Steiner SS, Burrell BB, Feldstein R, et Al. Pulmonary delivery of Technosphere™/insulin: Increased bioefficacy and bioavailability in clinical trials using the PDC Medtone™ inhaler. Proceed Int'l Symp Control Rel Bioact Mater 2000; 27: 1000-1001.
Stowell et al. "Development of GLP-1 Technosphere(TM) powder: an inhaled GLP-1 product." Diabetes Technology Meeting, San Francisco, Oct. 2007.
Strack "Inhaled Human Insulin." Drugs of Today 2006, 42 (4): 207-221.
Sturis et al., GLP-1 deriative liraglutide in rats with beta-cell deficiences: influence of metabolic state on beta-cell mass dynamics. British Journal of Pharmacology, 140 : 123-132 (2003).
Svartengren et al., Added External Resistance Reduces Oropharyngeal Deposition and Increases Lung Deposition of Aerosol Particles in Asthmatics. Am. J. Respir. Crit. Care Med., vol. 152, pp. 32-37, 1995.
Sympatecs. Dry Dispersion for Laser Diffraction and Image Analysis, 2011. XP-002586530.
Leone-Bay et al., Innovation in drug delivery by inhalation. Ondrugdelivery, No. 7, pp. 4-8 (2010).
Tack CJ, Boss AH, Baughman RA, et al. A randomized, double blind, placebo controlled study of the forced titration of prandial Technosphere®/Insulin in patients with type 2 diabetes mellitus. Diabetes 2006;55:Abstract 428-P.
Tack CJ, Christov V, deGalan BE, et al. Randomized forced titration to different doses of Technosphere® insulin demonstrates reduction in postprandial glucose excursions and hemoglobin A1c in patients with type 2 diabetes. J Diabetes Sci Technol 2008; 2(1) :47-57.
Tang-Christensen et al. "Central administration of GLP-1-(7-36) amide inhibits food and water intake in rats." Am J Physiol 271 (Regulatory Integrative Comp Physiol 40):R848, 1996.
Taylor et al. "Aerosols for macromolecule delivery. Design challenges and solutions." Am J Drug Deliv 2:143-155, 2004.
Teeter et al. "Dissociation of lung function changes with humoral immunity during inhaled human insulin therapy." Am J Resp Crit Care Med 173:1194, 2006.
Telko et al., Dry Powder Inhaler Formulation. Respiratory Care, Sep. 2005, vol. 50, No. 9, 1209-1227.
The American Diabetes Association "Insulin Administration" Diabetes Care, vol. 27, Supplement 1, S106-S109 (2004).
The Lancet. 1989, vol. 333, p. 1235-1236.
Thorens "Expression cloning of the pancreatic b-cell receptor for the gluco-incretin hormone glucagon-like peptide-1." PNAS 89:8641, 1992.
Thorens B et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in non-insulin-dependent diabetes mellitus." Eur J Clin Invest 27:533, 1997.
Todd et al. Subcutaneous glucagon-like peptide-1 improves postprandial glucaemic control over a 3-week period in patients with early type 2 diabetes. Clinical Science 95:325, 1998.
Toft-Nielson et al. "Determinants of the effectiveness of glucagon-like peptide-1 in type 2 diabetes." J Clin Endocrinol Metab 86:3853, 2001.
Toft-Nielson et al. "Exaggerated secretion of glucagon-like peptide-1 (GLP-1) could cause reactive hypoglcaemia." Diabetologia 41:1180, 1998.
Toft-Nielson et al. "The effect of glucagon-like peptide-1 (GLP-1) on glucose elimination in healthy subjects depends on the pancreatic glucoregulatory hormones." Diabetes 45:552, 1996.
Tornusciolo D.R. et al., Biotechniques 19(5):800-805, 1995. Simultaneous detection of TDT-mediated dUTP-biotin nick end-labeling (TUNEL)-positive cells and multiple immunohistochemical markers in single tissue sections.

(56) References Cited

OTHER PUBLICATIONS

Triantafyllidis et al., Structural, compositional and acidic characteristics of nanosized amorphous or partially crystalline ZSM-5 zeolite based materials. Microporous and Mesoporous Materials, 75:89-100 (2004).
Tu N, Kramer DA, Baughman RA. Inhaled Technosphere® Insulin improves glycemic control without weight gain. Diabetes 2007;56:Abstract 471-P.
Tuley et al., Experimental observations of dry powder inhaler dose fluidisation. International Journal of Pharmaceutics, 358, pp. 238-247 (2007).
Utah Valley University. Saponification. © 2009. Available from: <http://science.uvu.edu/ochem/index.php/alphabetical/s-t/saponification/printpage/>.
Vaczek, Accelerating drug delivery firms exploring new drug-delivery routes and devices intently awaiting the commercial launch of Exubera. Pharmaceutical & Medical Packaging News, vol. 14, No. 6 (2006).
Vahl et al. "Effects of GLP-1-(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.
Van Alfen-Van Der Velden et al. "Successful treatment of severe subcutaneou insulin resistance with inhaled insulin therapy", Pediatric Diabetes 2010: 11:380-382.
Vara E et al. "Glucagon-like peptide-1 (7-36) amide stimulates surfactant secretion in human type II pneumocytes." Am J Resp Crit Care Med 163:840-846, 2001.
Vella A et al. "Effect of glucagon-like peptide 1(7-36) amide on glucose effectiveness and insulin action in people with type 2 diabetes." Diabetes 49:611, 2000.
Vella A et al. "The gastrointestinal tract and glucose tolerance." Curr Opin Clin Nutr Metab Care 7:479, 2004.
Vendrame et al. "Prediabetes: prediction and prevention trials." Endocrinol Metab Clin N Am, 2004, vol. 33, pp. 75-92.
Verdich C, et al., A meta-analysis of the effect of glucagon-like peptide-1 (7-36) amide on ad libitum energy intake in humans. J Clin Endocrinol Metab., 86:4382-4389, 2001.
Vilsboll et al. "Reduced postprandial concentrations of intact biologically active glucagon-like peptide-1 in type 2 diabetic patients." Diabetes 50:609, 2001.
Vilsboll et al. "Similar elimination rates of glucagon-like peptide-1 in obese type 2 diabetic patients and healthy subjects." J Clin Endocrinol Metab 88:220, 2003.
Vilsboll et al., "Evaluation of β-Cell Secretary Capacity Using Glucagon-Like Peptide 1", Diabetes Care, vol. 23, No. 6, pp. 807-812, Jun. 2000.
Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.
Amorij et al., Development of stable infleunza vaccine powder formulations challenges and possibilities. Pharmaceutical Research, vol. 25, No. 6, pp. 1256-1273 (2008).
Audouy et al., Development of a dried influenza whole inactivated virus vaccine for pulmonary immunization. Vaccine, vol. 29, pp. 4345-4352 (2011).
Volund "Conversion of insulin units to SI units." American Journal of Clinical Nutrition, Nov. 1993, 58(5), pp. 714-715.
Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 is a physiological incretin in rat J. Clin. Invest., 95 : 417-421 (1995).
Wang et al., Glucagon-like peptide-1 regulates proliferation and apoptosis via activation of protein kinase B in pancreatic INS-1 beta cells. Diabetologia, 47:478-487, 2004.
Wareham et al., "Fasting Proinsulin Concentrations Predict the Development of Type 2 Diabetes", Diabetes Care, 1999, 22, 262-70.
Warren et al. "Postprandial versus prandial dosing of biphasic insulin aspart in elderly type 2 diabetes patients." Diabetes Res Clin Pract 66:23-29, 2004.
Waterhouse et al., "Comparatie assessment of a new breath-actuated inhaler in patients with reversible airways obstruction", Respiration 59:155-158 (1992).
WebMD (retrieved from http://www.webmd.com/pain-management/tc/pain-management-side-effects-of-pain-medicines in 2012, 4 pages).
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Weiss, SR et al. "Inhaled insulin provides improved glycemic control in patients with type 2 diabetes mellitus inadequately controlled with oral agents." Arch Intern Med 163:2277-2282, 2003.
Weissberger, "Mannkind: Overlooked Biotech with Excellent Prospects (Part V)," http://www.investorvillage.com/smbd.asp?mb=2885&mn=45817&pt=msg&mid=5021385 (posted on Jun. 19, 2008, accessed on Oct. 18, 2012).
West, Solid State Chemistry and its Applications, Chp 10, Solid Solutions. Wiley, New York, 358 (1998).
Wettergren A et al. "Truncated GLP-1 (proglucagon 78-107-Amide) inhibits gastric and pancreatic functions in man." Digestive Diseases and Sciences 38:665, 1993.
White JR et al. "Inhaled insulin: an overview." Clinical Diabetes 19:13-16, 2001.
Wigley et al., Insulin across respiratory mucosae by aerosol delivery. Diabetes 20(8): 552-556 (1971).
Willms B et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson BR et al. "Technospheres(TM) for pulmonary and nasal applications." Respiratory Drug Delivery VIII, 2002,p. 545.
Wilson et al., Spray-drying, a viable technosphere formulation process option to lyophilization, http://www.aapsj.org/abstracts/AM_2004/AAPS2004-002724.PDF, 1 page, 2004.
Witchert, Low molecular weight PLA: A suitable polymer for pulmonary administered microparticles. J. Microencapsulation, 10(2): 195-207 (1993).
Wright et al., Inhaled Insulin: Breathing new life into diabetes therapy. Nursing, vol. 37, No. 1, p. 46-48 (2007).
Wong et al. "From cradle to grave: pancreatic b-cell mass and glucagon-like peptide-1." Minerva Endocrinologica 31:107, 2006.
Wuts et al. "The Role of Protective Groups in Organic Synthesis," John Wiley, New York, 2nd Ed. 1991.
Yan et al., Analgesic action of microinjection of neurokinin A into the lateral reticular nucleus and nucleus raphe magnus in rats. Acta Physiologica Sinica, vol. 48, No. 5, pp. 493-496 (1996)—abstract.
Yang et al., Division and differentiation of natural antibody-producing cells in mouse spleen. PNAS, 104(11): 4542-4546 (2007).
Yoshida et al., Absorption of insulin delivered to rabbit trachea using aerosol dosage form. J. Pharm. Sci. 68(5): 670-671 (1979).
Yoshioka et al., "Serum proinsulin levels at fasting and after oral glucose load in patients with Type 2 (non-insulin dependent) diabetes mellitus", Diabetogia, 1988, 31, 355-60.
Yu W, Marino MT, Cassidy JP, et al. Insulin antibodies associated with Technosphere® insulin. ADA 2010; Abstract 216-OR.
Yusta B et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
Zimmerman, K., "Respiratory System: Fats, Function, and Diseases", <www.livescience.com/22616-respiratory-system.html>, copyright 2013, p. 1.

(56) References Cited

OTHER PUBLICATIONS

Zisser et al. "In Patients Using Technospere Insulin. Variation in PPG Stayed Within ADA-recommended Targets Despite Large Variations in Glucose Load." Mannkind Corporation (2010), ADA 2010; Poster 554.
Zisser H, Jovanovic L, Markova K, et al. Technosphere® insulin effectively controls postprandial glycemia in patients with type 2 diabetes mellitus. Diabetes Technology and Therapeutics 2012;14:997-1001.
Bosquillon et al., Pulmonary delivery of growth hormone using dry powders and visualization of its local fate in rates. Journal of Controlled Release 96: 233-244 (2004).
Cho et al., Targeting the glucagon receptor family for diabetes and obesity therapy. Pharmacology & Therapeutics 135: 247-278 (2012).
Definition of medicament from http://medical-dictionary.thefreedictionary.com/medicament, retrieved by the Examiner on Mar. 20, 2015 and cited in Office Action dated Mar. 26, 2015 in U.S. Appl. No. 13/942,482.
Definition of matrix from http://medical-dictionary.thefreedictionary.com/matrix, retrieved by the Examiner on Mar. 5, 2015 and cited in Office Action dated Mar. 26, 2015 in U.S. Appl. No. 12/471,260.
Diabetes Frontier, vol. 10, No. 5, p. 647-657 (1999) (full Japanese article with translated English portion provided in separate attachment, portion translated in English is the bottom of p. 655 and the left col. of p. 656).
Ely et al., Effervescent dry powder for respiratory drug delivery. European Journal of Pharmaceutics and Biopharmaceutics 65: 346-353 (2007).
European Search report for European Application 14192154.4 dated Mar. 19, 2015.
Extended European Search report for European Application 14187552.6 dated Mar. 2, 2015.
Gillespie et al., Using carbohydrate counting in diabetes clinical practice. Journal of the American Diabetic Association, vol. 98, No. 8, p. 897-905 (1998).
Yamamoto et al., Engineering of Poly (DL-lactic-co-glycolic acid) Nano-composite particle for dry powder inhalation dosage forms of insulin with spray fludized bed granulating system. J. Soc. Powder Technol., Japan, 41: 514-521 (2004).
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, 2008.
Rosenstock et al. "Inhaled Insulin Improves Glycemic Control when Substituted for or Added to Oral Combination Therapy in Type 2 Diabetes." Ann Intern Med 143:549-558, 2005.
Rosenstock et al., "Reduced hypoglycemia risk with insulin glargine: a meta-analysis comparing insulin glargine with human NPH insulin in type 2 diabetes", Diabetes Care, 28(4):950-5 (2005).
Rosenstock J, Baughman RA, Ribera-Schaub T, et Al. A randomized, double-blind, placebo controlled study of the efficacy and safety of inhaled Technosphere® insulin in patients with type 2 diabetes (T2DM). Diabetes 2005;54: Abstract 357-OR.
Rosenstock J, Lorber D, Petrucci R, et al. Basal/bolus with prandial inhaled Technosphere® insulin (TI) plus insulin glargine qd vs biaspart 70/30 insulin bid in T2 DM inadequately controlled on insulin with/without oral agents ADA 2009; Poster 466.
Rosenstock J, Lorger DL. Gnudi L, et al.Prandial inhaled insulin plus basal insulin glargine versus twice daily biaspart insulin for type 2 diabetes: a multicentre randomised trial. Lancet 2010;375:2244-2253.
Rossiter A, Amin N, Harris R, et al. Pulmonary safety of inhaled Technosphere® insulin therapy in adults with diabetes using high-resolution computerized tomography of the chest. Diabetologia 2009; 52 (suppl 1).
Rossiter A, Howard C, Amin N, et al. Technosphere® insulin: Safety in type 2 diabetes mellitus. ADA 2010; Poster 523.
Roumeliotis, New inhaler launched with a bag, in-Pharma Technologist.com, Decision News Media SAS (2006).
Rousseau et al. "Drug delivery by fumaryl diketopiperazine particles: evidence for passive transport." Presented at the American Diabetes Association 64th Scientific Sessions, Jun. 2004, abstract 484-P.
Rubin RR, Peyrot M. Psychometric properties of an instrument for assessing the experience of patients treated with inhaled insulin: The inhaled insulin treatment questionnaire (INTQ) Health & Quality of Life Outcomes 2010.8:32.
Rubin RR, Peyrot M; Patient reported outcomes in adults with type 1 diabetes using mealtime AFRESA® (inhaled Technosphere® insulin) or rapid acting insulin with basal insulin ADA 2009; Poster 1881.
Ryan EA et al. "Successful islet transplantation. Continued insulin reserve provides long-term glycemic control." Diabetes 51:2148-2157, 2002.
Sajeesh et al., Cyclodextrin-insulin complex encapsulated polymethacrylic acid based nanoparticles for oral insulin delivery. International Journal of Pharmaceuticals, 2006, 325, pp. 147-154.
Sakagami M et al. "Respirable microspheres for inhalation: the potential of manipulating pulmonary disposition for improved therapeutic efficacy." Clin Pharmacokinet 44(3):263-277, 2005.
Sakr, A new approach for insulin delivery via the pulmonary route: design and pharmacokinetics in non-diabetic-rabbits. International Journal of Pharmaceutics, 86: 1-7 (1992).
Salib, Utilization of sodium alginate in drug microencapsulation. Pharazeutische Industrie, 40(11a): 1230-1234 (1978).
Saraceni C et al. "Effects of glucagon-like peptide-1 and long-acting analogues on cardiovascular and metabolic function." Drugs R D 8:145, 2007.
Sarrach et al., "Binding and entrapment of insulin by liposomes made of lecithin-phosphotidix acid in acid solution" Pharmazie 40:642-645, 1985 (German and English Abstract).
Savage et al., "Effects of peptide YY (PYY) on mouth to caecum intestinal transit time and on the rate of gastric emptying healthy volunteers", Gut, vol. 28, pp. 166-170, 1987.
Sawhney et al., Bioerodible hydrogels based on photopolymerized poly(ethylene glycol)-co-poly(a-hydroxy acid) diacrylate macromers. Macromolecules, 26: 581-587 (1993).
Schaffer et al. "Assembly of high-affinity insulin receptor agonists and antagonists from peptide building blocks." PNAS 100:4435-4439, 2003.
Schepp et al., Eur. J. Pharmacol., 269:183-91, 1994.
Scherbaum "Unlocking the opportunity of tight glycaemic control. Inhaled insulin: clinical efficacy." Diabetes Obesity and Metabolism 7:S9-S13, 2005.
Schirra et al. "Gastric emptying and release of incretin hormones after glucose ingestion in humans." J Clin Invest 97:92-103,1996.
Schluter et al., "Pulmonary Administration of Human Insulin in volunteers and Type I Diabetics", Diabetes, 33, (Suppl) 298 (1984).
Schneider et al., "Stimulation by proinsulin of expression of plasminogen activator inhibitor type 1 in endothelial cells", Diabetes 41(7):890-895 (1992).
Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-494, 1979.
Schroder, "Crystallized carbohydrate spheres as a slow release matrix for biologically active substances", Biomaterials 5:100-104, 1984.
Scrocchi et al. "Glucose intolerance but normal satiety in mice with a null mutation in the glucagon-like peptide 1 receptor gene." Nature Medicine 2:1254-1258, 1996.
Seshiah & Balaji, "Early Insulin Therapy in Type 2 Diabetics", Int. J. Diabetes in Developing Countries, 2003, 23, 90-93.
Seville, P.C. et al., Preparation of dry powder dispersions for non-viral gene delivery by freeze-drying and spray drying. J. Gene Medicine 2002; 4:428-437.
Shah et al. "Lack of suprression of glucagon contributes to post-prandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.

(56) References Cited

OTHER PUBLICATIONS

Shimada et al. Translocation pathway of the intertracheally instilled ultrafine particles from the lung into the blood circulationin the mouse. Toxicologic Pathology pp. 949-957 (2006).
Shojania et al. "Effect of quality improvement strategies for type 2 diabetes on glycemic control." JAMA 296:427, 2006.
Silverstein et al., "Care of Children and Adolescens with Type 1 Diabetes, A Statement of the American Diabetes Association", Diabetes Care, Jan. 2005, vol. 28, p. 186-212.
Singh et al., Use of 125I-[Y39]exendin-4 to characterize exendin receptors on dispersed pancreatic acini and gastric chief cells from guinea pig. Regul. Pept. 53 : 47-59 (1994).
Simms JR, Carballo I, Auge CR, et al Assessment of immunotoxic effects on humoral and cellular immune parameters following repeated inhalation of Technosphere insulin in the rat Diabetes 2005;54:Abstract 2078-PO.
Skyler, Pulmonary insulin: current status. Diabetes Voice, vol. 51, Issue I, p. 23-25, 2006.
Skyler "Pulmonary Insulin Delivery—State of the Art 2007." Diabetes Tecnology & Therapeutics, vol. 9, Supplement 1, pp. S1-S3. 2007.
Skyler JS et al. "Use of inhaled insulin in a basal/bolus insulin regimen in Type 1 diabetic subjects." Diabetes Care 28:1630-1635,2005.
Smith et al. "New-onset diabetes and risk of all-cause and cardiovascular mortality." Diabetes Care 29:2012, 2006.
Smutney CC, Friedman EM, Amin N. Inspiratory efforts achieved in use of the Technosphere® insulin inhalation system. Diabetes Technology Meeting 2008; Poster SMUT8052.
Smutney CC, Friedman EM, Amin N. Inspiratory efforts achieved in use of the Technosphere® insulin inhalation system. Journal of Diabetes Science and Technology 2009 3(5):1175-1189.
Smutney CC, Polidoro JM, Adamo B, et al. In-vitro performance improvement realized in a next generation dry powder delivery system. Diabetes Technology Meeting 2009; poster.
Smutney CC, Polidoro JM, Adamo B, Shah S. In vitro performance improvement realized in a next generation dry powder delivery system. Third International Conference on Advanced Technologies and Treatments for Diabetes 2010; Poster 122.
Smutney CC, Polidoro JM. Easy-to-use next-generation pulmonary insulin delivery system. ADA 2010; Abstract 2093.
Smutney CC, Polidoro JM. Improvements realized in a next-generation pulmonary insulin delivery system. ADA 2010; Abstract 2097.
Sodium chloride is a natural product from http://www.wqpmag.com/potassium-chloride-vs-sodium-chloride, pp. 1-3. Accessed by Examiner on May 16, 2014 and in Non-Final Offfice Action dated May 22, 2014 for U.S. Appl. No. 13/797,657 and in Non-Final Office Action dated May 22, 2014 for U.S. Appl. No. 12/883,369.
Nathan DM et al. "Management of hyperglycemia in Type 2 diabetes: a consensus algorithm for the initiation and adjustment of therapy." Diabetes Care 29:1963-1972, 2006.
Nathan DM et al. "Management of hyperglycemia in Type 2 diabetes: a consensus algorithm for the initiation and adjustment of therapy." Diabetes Care 31:173-175, 2008.
Nathan DM et al. "Management of hyperglycemia in Type 2 diabetes: a consensus algorithm for the initiation and adjustment of therapy." Diabetes Care 32:193-203, 2009.
Nathan et al. "Intensive diabetes treatment and cardiovascular disease in patients with Type 1 diabetes." New Eng. J. Med. 353:2643-2653, 2005.
Nathan, "Initial Management of Glycemia in Type 2 Diabetes Melllitus" N. Eng. J. Med., 2002, 347, 1342-9.
Nauck "Is glucagon-like peptide 1 an incretin hormone?" Diabetologia 42:373-379, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46-52, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
Nemmar et al., Passage of inhaled particles into the blood circulation in humans. Circulation pp. 411-414 (2002).
Newman, Principles of metered-dose inhaler design. Respiratory Care, vol. 50, No. 9, pp. 1177-1190 (2005).
Next Generation Inhaler Nears Market, Manufacturing Chemist, Cambridge Consultants, Polygon Media Ltd. (2006).
NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.
Non-covalent interactions from UC Davis ChemWiki, pp. 1-5. Accessed by Examiner on Jul. 23, 2013 and related case U.S. Appl. No. 12/830,557.
Nystrom et al. "Effects of glucagon-like peptide-1 on endothelial function in type 2 diabetic patients with stable coronary artery disease." Am J Physiol Endocrinol Metabl 287:E1209, 2004.
Oberdorster et al., Correlation between particle size, in vivo particle persistence, and lung injury. Environ Health Perspect 102 Suppl 5, pp. 173-179 (1994).
Oberdorster et al.,Pulmonary effects of inhaled ultrafine particles. International Archives of Occupational and Environmental Health, vol. 74, pp. 1-8 (2001).
Okumura et al., Intratracheal delivery of insulin: absorption from solution and aerosol by rat lung. Int. J. Pharmaceuticals 88: 63-73 (1992).
O'Neill, Air pollution and inflammation in type 2 diabetes: a mechanism for susceptibility. Occup Environ Med. vol. 64, pp. 373-379 (2007).
Oshima et al. "Comparison of half-disappearance times, distribution volumes and metabolic clearance rates of exogenous glucagon-like peptide 1 and glucagon in rats." Regulatory Peptides 21:85, 1988.
Ostrovsky, Gene. Mannkind Inhalation Insulin Going to FDA to Seek Approval [on-line]. MedGadget.com, posted on Mar. 17, 2009, Retrieved from the Internet: <URL:http://medgadget.com/2009/03mannkind_inhalation_insulin_going_to_fda_to_seek_approval.html>.
Owens et al. "Inhaled human insulin." Nature Reviews, Drug Discovery, vol. 5, No. 5, pp. 371-372, May 2006.
Owens et al. "Alternative routes of insulin delivery." Diabetic Medicine 20:886-898, 2003.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Pacini P, Marino MT. Evaluation of endogenous and exogenous components to peripheral insulin concentration during administration of inhaled insulin. ADA 2010; Abstract 2094-PO.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Obesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.
Patton et al. "Clinical pharmacokinetics and pharmacodynamics of inhaled insulin." Clin Pharmacokinet 43:781-801, 2004.
Patton et al., "Inhaled Insulin", Advanced Drug Delivery Reviews, 35, Feb. 1999, p. 235-247.

(56) References Cited

OTHER PUBLICATIONS

Onoue et al., Dry powder inhalation systems for pulmonary delivery of therapeutic peptides and proteins. Expert Opin. Ther. Patents 18(4):429-442 (2008).
Pearson et al., Systematically Initiating Insulin, supplemental to vol. 32, No. 1, 19S-28S, 2006.
Perera et al. "Absorption and Metabolic Effect of Inhaled Insulin." Diabetes Care, vol. 25, No. 12, Dec. 2002, p. 2276-2281.
Pesic, Inhaler delivers more drug to the deep lung, says Cambridge Consultants. in-Pharma Technologist.com, http://www/in-pharmatechnologist.com/content/view/print/344335, Dec. 1, 2010.
Petkowicz et al., "Hypoglycemic effect of liposome-entrapped insulin adminstered by various routes into normal rats", Pol. J. Pharmacol. Pharm. 41:299-304 (1989).
Petrucci R, Amin N, Lovertin P. et al. Pulmonary function tests remain similar in patients who received Technosphere® insulin and in patients currently receiving standard antidiabetic therapy. Diabetologia 2009; 52 (suppl 1).
Peyrot et al. "Resistance to insulin therapy among patients and providers." Diabetes Care 28:2673-2679, 2005.
Peyrot M, Rubin RR, Otterbach K. Effect of Technosphere® inhaled insulin on treatment satisfaction, glycemic control and quality of life. Diabetes 2006; 55:Abstract 423-P.
Pezron et al., Insulin aggregation and asymmetric transport across human bronchial epithelial cell monolayers (Calu-3). J. Pharmaceutical Sci. 91: 1135-1146 (2002).
Pfeiffer MA et al. Insulin secretion in diabetes mellitus. Am J Med 70:579-88, 1981.
Pfutzner et al., Abstract 812: Influence of small dose i.v.s.c. and pulmonary insulin treatment on grandial glucose control in patients with type 2 diabetes. Internet Article [Online] 2001, 37th Annual Meeting of the EASD, Glasgow, Sep. 9-13, 2001.
Pfutzner A et al. "Pulmonary insulin delivery by means of the Technosphere(TM) drug carrier mechanism." Expert Opin Drug Deliv 2:1097-1106, 2005.
Pfützner A et al. "Technosphere®/Insulin—a new approach for effective delivery of human insulin via the pulmonary route." Diab Tech Ther 4:589-594, 2002.
Pfützner A et al. "Lung distribution of radiolabeled Technosphere™/Insulin." Diabetes 52 Supplement, Jun. 2003, A107.
Pfützner A et al. Pilot study with Technosphere/PTH(1-34)—a new approach for effective pulmonary delivery of parathyroid hormone (1-34). Horm Metab Res 35:319-323, 2003.
Pfützner A et al. "Variability of insulin absorption after subcutaneous and pulmonary application in patients with type 2 diabetes." Diabetes 51 Supplement, Jun. 2002, A47-48.
Pfutzner et al. "Inhaled Technosphere/Insulin Shows a Low Variability in Metabolic Action in Type 2 Diabetic Patients." Diabetes 49 Supplement, May 2000, A121.
Pfuetzner A, Rave K, Heise T, et al. Inhaled Technosphere™/insulin results in low variability in metabolic action in type 2 diabetic patients. Exp Clin Endocrinol Diabetes 2000; 108:S161.
Pfuetzner A, Rave K, Heise T, et al. Low variability in metabolic action in type 2 diabetic patients with inhaled Technosphere/insulin. Diabetologia 2000; 43:Abstract 774.
Phillips M, Amin N, Boss AH, et al. Pulmonary functions (over 2 years) in diabetic subjects treated with Technosphere® insulin or usual antidiabetic treatment. Diabetologia 2009; 52 (suppl 1).
Pohl R, Muggenberg BA, Wilson BR, et al. A dog model as predictor of the temporal properties of pulmonary Technosphere/insulin in humans. Respiratory Drug Delivery 2000; VII: 463-465.
Polonsky et al. "Abnormal Patterns of Insulin Secretion in Non-insulin-Dependent Diabetes Mellitus." N Eng J Med 318:1231-39, 1988.
Potocka E, Amin N, Cassidy J, et al. Insulin pharmacokinetics following dosing with Technosphere® insulin in subjects with chronic obstructive pulmonary disease. Current Medical Research and Opinion 2010; 26:2347-2353.
Potocka E, Baughman R A, Derendort H. Population pharmacokinetic model of human insulin following different routes of administration. Journal of Clinical Pharmacology 2011;51:1015-1024.
Potocka E, Baughman R, Derendort H. Population Pharmacokinetic Model of Regular Human Insulin Following Different Routes of Administration. AAPS Journal. 2009; 11(S1). Available from: http://www.aapsj.org. Presented at the 2009 AAPS (American Association of Pharmaceutical Scientists) National Biotechnology Conference, Jun. 21-24, Seattle, WA.
Potocka E, Baughman RA, Derendorf J. A population PK/PD model of Technosphere® insulin administered to healthy and type 2 diabetics. ADA 2010; Poster 624.
Potocka E, Baughman RA, Schwartz SL, et al. Pharmacokinetics of AFRESA® unchanged in patients with chronic obstructive pulmonary function ADA 2009; Poster 437.
Potocka E, Cassidy J P, Haworth P, et al. Pharmacokinetic characterization of the novel pulmonary delivery excipient fumaryl diketopiperazine. Journal of diabetes science and technology 2010;4:1164-1173.
Potocka E, Cassidy JP, Haworth P, et al. Pharmacokinetic characterization of fumaryl diketopiperazine. Third International Conference on Advanced Technologies and Treatments for Diabetes 2010; Poster 291.
Potocka E, Hovorka R, Baughman R, et al. Characterization of metabolism parameters following Technosphere® insulin and insulin Lispro. ADA 2010; Poster 1561.
Potocka E, Hovorka R, Baughman RA, et al. AFRESA™ supresses endogenous glucose production earlier than a rapid-acting analog (Lispro) and inhaled Exubera® ADA 2009; Oral 232.
Potocka E, Hovorka R, Baughman RA, et al. Technosphere® insulin suppresses endogenous glucose production earlier than a rapid-acting analog (lispro) and an inhaled insulin (exubera). Diabetologia 2009; 52 (suppl 1).
Prabhu et al. "A study of factors controlling dissolution kinetic of zinc complexed protein suspensions in various ionic species", Int. J. Pharm. 217(1-2):71-8 (2001).
Laube et al., The lung as an alternative route for delivery for insulin in controlling postrprandial glucose levels in patients with diabetes. Chest, Preliminary Report 114 (6) : 1734-1739 (1998).
Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.
Rachman et al. "Normalization of insulin responses to glucose by overnight infusion of glucagon-like peptide 1 (7-36) amide in patients with NIDDM." Diabetes 45:1524, 1996.
Raju et al., Naseseazines A and B: a new dimeric diketopiperazine framework from a marine-derived actinomycete, *Streptomyces* sp. Organic letters, vol. 11, No. 17, pp. 3862-3865 (2009).
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Raskin P, Heller S, Hanka M, et al. Pulmonary function over 2 years in diabetic patients treated with prandial inhaled Technosphere® Insulin or usual antidiabetes treatment: A randomized trial. Diabetes, Obesity and Metabolism 2012;14:163-173.
Raskin P, Phillips M, Amin N, et al. Hypoglycemia in patients with type 1 diabetes incorporating prandial inhaled Technosphere® insulin into their usual diabetes treatment regimen vs continuing their usual diabetes management. AACE 2010; Poster 283.
Raskin P, Phillips MD, Rossiter A, et al. A1C and hypoglycemia in patients with type 2 diabetes mellitus incorporating prandial inhaled Technosphere® insulin into their usual antihyperglycemic regimen vs continuing their usual antihyperglycemic regimen. ADA 2010; Abstract 359-OR.
Raufman et al., Exendin-3, a novel peptdie from Heloderma horridum venom, interacts with vasoactive intestinal peptide receptors and a newly described receptor on dispersed aciin from guinea pig pancreas. J. Biol. Chem. 266(5) : 2897-2902 (1991).

(56) References Cited

OTHER PUBLICATIONS

Raufman et al., Truncated glucagon-like peptide-1 interacts with exendin receptors on dispersed acini from guina pig pancreas. J. Biol. Chem. 267(30) : 21432-21437 (1992).
Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Dose Response of Inhaled Dry-Powder Insulin and Dose Equivalence to Subcutaneous Insulin Lispro." Diabetes Care 28:2400-2405, 2005.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.
Rave et al. "Results of a Dose-Response Study with a New Pulmonary Insulin Formulation and Inhaler." Diabetes 49, Supplement, May 2000, A75.
Rave et al. "Time-action profile of inhaled insulin in comparison with subcutaneously injected insulin lispro and regular hman insulin." Diabetes Care 28:1077, 2005.
Rave K, Heise T, Pfuetzner A, et al. Assessment of dose-response characteristics for a new pulmonary insulin formulation and inhaler. Exp Clin Endocrinol Diabetes 2000; 108:S161.
Rave K, Potocka E, Boss AH, et al. Pharmacokinetics and linear exposure of AFRESA™ compared with the subcutaneous injection of regular human insulin Diabetes, Obesity and Metabolism 2009; 11:715-720.
Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.
Razavi et al. "TRPVI+ sensory neurons control beta cell stress and islet inflammation in autoimmune disease." Cell 127:1123,2006.
Retrieved from website: http://groups.molbiosci.northwestern.edu/holmgren/Glossary/Definitions/Def-P/placebo.html, 1 page, Retrieved on Mar. 12, 2013.
Rhodes et al. "Technosphere: Microspherical Particles from Substituted Diketopiperazines for Use in Oral Drug Delivery." 208th ACS National Meeting, Aug. 1994.
Richardson et al. "Technosphere Insulin Technology." Diabetes Technology & Therapeutics, vol. 9, Supplement 1, pp. S65-S72, 2007.
Richardson PC, Potocka E, Baughman RA, et al. Pharmacokinetics of Technosphere® insulin unchanged in patients with chronic obstructive pulmonary disease. Diabetologia 2009; 52 (suppl 1).
Richter et al. "Characterization of glucagon-like peptide-1(7-36)amide receptors of rat membranes by covalent cross-linking." FEBS Letters 280:247, 1991.
Richter et al. "Characterization of receptors for glucagon-like peptide-1 (7-36)amide on rat lung membranes." FEBS Letters 267:78, 1990.
Riddle "Combining Sulfonylureas and Other Oral Agents." Am J Med, 2000, vol. 108(6A), pp. 15S-22S.
Riddle et al. "Emerging therapies mimicking the effects of amylin and glucagon-like peptide 1." Diabetes Care 29:435,2006.
Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.
Rosen et al., Substance P microinjected into the periaqueductal gray matter induces antinociception and is released folloing morphine administration. Brain Research, 1001: 87-94 (2004).
Rosenmund et al., Diketopiperazines from Leuchs Anhydrides. Angew Chem Intern. Edit. vol. , No. 2 (1970).
Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.
Li et al. "GLP-1; a novel zinc finger protein required in somatic cells of the gonad for germ cell development." Dev Biol 301:106, 2007.
Li, Jun. Chapter 15: Drug Therapy of Metabolic Diseases. Clinical Pharmacotherapy, People's Medical Publishing House, 1st Edition, pp. 333-335 (2007).
Lian et al. "A Self-Complimentary Self-Assembling Microsphere System: Application for Intravenous Delivery of the Antiepilpetic and Neuroprotectant Compound Felbanate." J Pharm Sci 89:867-875, 2000.
Lim, "Microencapsulation of Living Cells and Tissues", J. Pharm. Sci., 70: 351-354 (1981).
Linder et al., Increase in serum insulin levels is correlated with lung distribution after pulmonary delivery of Technosphere/Insulin. Diabetologia, No. 46, A277 (2003).
Liu et al., "Pulmonary delivery of free and liposomal insulin", Pharmaceuticals Res. 10:228-232, 1993.
Lorber D, Howard CP, Ren H, et al. Reduced incidence and frequency of hypoglycemia in an integrated analysis of pooled data from clinical trials of subjects with type 2 diabetes using prandial inhaled Technosphere® insulin. AACE 2010; Poster 270.
Luque et al. "Glucagon-like peptide-1 (GLP-1) and glucose metabolism in human myocytes." J. Endocrinol 173:465, 2002.
Luzi, L. and DeFronzo, R.A. "Effect of loss of first-phase insulin secretion on hepatic glucose production and tissue glucose disposal in humans." Am. J. Physiol. 257 (Endocrinol. Metab. 20):E241-E246, 1989.
Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67, 1991.
Malhotra et al., Exendin-4, a new peptide from Heloderma suspectum venom, potentiates cholecystokinin-induced amylase release from rat pancreatic acini. Regulatory Peptides, 41:149-56, 1992.
Mandal "Inhaled insulin for diabetes mellitus." Am J Health Sys Pharm 62:1359-64, 2005.
Mann "Pulmonary insulin—the future of prandial insulin therapy." Presented at the 5th Annual Meeting of the Diabetes Technology Society, Nov. 2005, abstract A94.
Mannkind Corporation "Postprandial hyperglycemia: clinical significance, pathogenesis and treatment." MannKind Corporation Monograph. 2009.
MannKind Corporation, Pulmonary Delivery: Innovative Technologies Breathing New Life into Inhalable Therapeutics, www.ondrugdelivery.com, 2006.
Burcelin et al., Long-lasting antidiabetic effect of a dipeptidyl peptidase IV-resistant analong of glucagon-like peptide-1. Metabolism, vol. 48, No. 2, pp. 252-258 (1999).
Marino MT, Cassidy JP, Smutney CC, et al. Bioequivalence and dose proportionality of Afrezza® inhalation powder administered using a Gen2 inhaler compared to the MedTone® inhaler. Diabetes Technology Meeting 2010; poster.
Marino MT, Cassidy JP, Smutney CC, et al. Improvement in bioavailability of FDKP with the NexGen2A device: Implications for delivery of pulmonary insulin. Third International Conference on Advanced Technologies and Treatments for Diabetes 2010; Poster 108.
Marino MT, Cassidy JP, Smutney CC, et al. Improvement in bioavailability of FDKP and insulin with the NGDSB device. Third International Conference on Advanced Technologies and Treatments for Diabetes 2010; Poster 107.
Marino MT. A pharmacokinetic/pharmacodynamic model of inhaled insulin with application to clinical trial simulation. ADA 2010; Abstract 2105-PO.
Marino MT. Cassidy JP, Baughman RA, et al. C-peptide correction method to determine exogenous insulin levels in pk studies using AFRESA® (Technosphere® insulin [TI]) ADA 2009; Poster 1451.
Marshall "Preventing and detecting complications of diabetes." BMJ 333:455, 2006.

(56) References Cited

OTHER PUBLICATIONS

Mastrandrea "A breath of life for inhaled insulin: severe subcutaneous insulin resistance as an indication." Pediatric Diabetes 2010: 11: 377-379.

Mathiowitz, Morphology of Polyanhydride Microsphere Delivery Systems, Scanning Microscopy, 4: 329-340 (1990).

Mathiowitz, Novel microcapsules for delivery systems. Reactive Polymers, 6: 275-283 (1987).

Mathiowitz, Polyanhydride microspheres as drug carriers I, hot-melt microencapsulation. J. Controlled Medicine, 5: 13-22 (1987).

Mathiowitz, Polyanhydride microspheres as drug carriers II, microencapsulation by solvent removal. J. Appl. Polymer Sci., 35: 755-774 (1988).

Mathiowitz, Polyanhydride microspheres IV, morphology and characterization systems made by spray drying. J. App. Polymer Sci., 45: 125-134 (1992).

Matsui et al. "Hyperplasia of type II pheumocytes in pulmonary lymphangioleiomyomatosis. Immunohistochemical and electron microscope study." Arch Pathol Lab Med 124:1642, 2000.

Matthews DR et al. "Homeostasis model assessment: insulin resistance and beta-cell function from fasting plasma glucose and insulin concentrations in man." Diabetologia. Jul. 1985;28(7):412-9.

McElduff A et al. "Influence of acute upper respiratory tract infection on the absorption of inhaled insulin using the AERx(R) insulin diabetes management system." Br J Clin Pharmacol 59:546, 2005.

Mcmahon et al., "Effects of basal insulin supplementation on disposition of mixed meal in obese patients with NIDDM", Diabetes, vol. 38, pp. 291-303 (1989).

Meier et al. "Absence of a memory effect for the insulinotropic action of glucagon-like peptide-1 (GLP-1) in healthy volunteers." Horm Metab Res 35:551, 2003.

Meier et al. "Secretion, degradation, and elimination of glucagon-like peptide-1 and gastric inhibitor polypeptide in patients with chronic renal insufficiency and healthy control subjects." Diabetes 53:654, 2004.

Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.

Mendes et al., A non-dimensional functional relationship for the fine particle fraction produced by dry powder inhalers, Aerosol Science 38, pp. 612-624 (2007).

Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.

Merck Manual 17th, Japanese Edition, NIKKEI BP Corp., 1999, p. 167-179.

Mitchell et al. "Intranasal Insulin: PK Profile Designed Specifically for Prandial Treatment of Type 2 Diabetes." Drug Development Research 69(3):143-152 (2008).

Monnier et al. "Activation of oxidative stress by acute glucose fluctuations compared with sustained chronic hyperglycemia in patients with type 2 diabetes." JAMA 295:1681, 2006.

Montrose-Rafizadeh et al. Diabetes, 45(Suppl. 2):152A, 1996.

Moren, Aerosols in Medicine (2nd Ed.), Elsevier, pp. 321-350 (1993).

Mudaliar et al., Insulin Therapy in Type 2 Diabetes. Endocrinology and Metabolism Clinics, vol. 30, No. 4, pp. 1-32 (2001).

Nagai et al., "Powder Dosage Form of Insulin for Nasal Administration", J. Control Ref., 1:15-22 (1984).

Narayan et al. "Impact of recent increase in incidence on future diabetes burden." Diabetes Care 29:2114, 2006.

Naslund E et al. "GLP-1 slows solid gastric emptying and inhibits insulin, glucagon, and PYY release in humans." Am J Physiol (Regulatory Integrative Comp Physiol 46):R910, 1999.

Naslund E et al. "Prandial subcutaneous injections of glucagon-like petide-1 cause weight loss in obese human subjects." Br J Nutrition 91:439, 2004.

International Search Report dated Nov. 21, 2013 for International Application No. PCT/US2013/057397 filed on Aug. 29, 2013.

Eavarone et al., A voxel-based monte carlo model of drug release from bulk eroding nanoparticles. Journal of Nanoscience and Nanotechnology, vol. 10, pp. 5903-5907 (2010).

Marino MT, Cassidy JP, Smutney CC, et al. Improvement in bioavailability of FDKP with the NexGen2A device: Implications for delivery of pulmonary insulin. Diabetes Technology Meeting 2009; poster.

"An inhaled insulin formulation (Technosphere Insulin) effectively improves glycaemic control in patients with type 2 diabetes mellitus." Inpharma Weekly, vol. 1522, Jan. 28, 2006, p. 8.

ACTOS Product Insert. Aug. 2008.

Adjusting Mealtime Insulin Doses. BD Diabetes. http://www.bd.com/diabetes/page.aspx?cat=7001&id=7280 (2014).

Ahren "GLP-1 and extra-islet effects." Horm. Med Res 36:842, 2004.

Ahren B et al. "Characterization of GLP-1 effects on b-cell function after meal ingestion in humans." Diabetes Care 26:2860, 2003.

Ahren B., Glucagon-like peptide-1 (GLP-1): a gut hormone of potential interest in the treatment of diabetes. BioEssays, V. 20, pp. 642-651 (1998).

Akerlund et al., Diketopiperazine-based polymers from common acids. Journal of Applied Polymer Science (2000), 78(12), 2213-2218.

Alabraba et al. Diabetes Technology & Therapeutics. Jul. 2009, 11(7): 427-430.

Alcohols limited. Alcohol speciality solvents—Go green! Jul. 24, 2010. Available from: <http://webarchive.org/web/20100724193725/http://www.alcohols.co.uk/speciality_solvents.php>.

Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.

Al-Showair et al., Can all patients with COPD use the correct inhalation flow with all inhalers and does training help? Respiratory Medicine, vol. 101, No. 11, p. 2395-2401 (2007).

American Diabetes Association, "Standards of medical care in diabetes—2009", Diabetes Care, Jan. 2009, 32 Suppl 1: S13-61.

Amin N, Boss AH, Petrucci R, et al. Pulmonary functions (over 2 years) in diabetic subjects treated with AFRESA® or usual antidiabetic treatment ADA 2009; Poster 570.

Amin N, et al. Long-term sustained safety and efficacy of continued use of Technosphere insulin in subjects with type 2 diabetes. Abstract—Oral Presentation 215, 48th EASD Annual Meeting, Sep. 29-Oct. 2, 2009, Vienna Austria.

Amin N, Marino MT, Cassidy JP, et al. Acute pulmonary effects of Technosphere® insulin inhalation powder administered using a Gen2B inhaler compared to MedTone® C inhaler. Diabetes Technology Meeting 2010; poster.

Amin N, Phillips M, Boss AH, et al. Pulmonary functions (over 2 years) in diabetic patients treated with Technosphere® insulin (TI) or usual antidiabetic treatment. Third International Conference on Advanced Technologies and Treatments for Diabetes. 2010; Poster 290.

Angelo et al., Technosphere Insulin: Defining the Role of Technosphere Particles at the Celluar Level. J. Diabetes Sci. Technol., vol. 3, Issue 3, pp. 545-554 (2009).

Angelo et al. Technosphere® insulin inhalation powder: Defining the mechanism of action. ADA 2008; 57: Poster 428-P.

Antosiewiez et al., Prediction of pH-dependent properties of proteins. J Mol. Biol., 238:415-436 (1994).

Arakawa et al., Preferential interactions determine protein solubility in three-component solutions: the MgCl2 system. Biochemistry, 29:1914-1923 (1990).

Ashwell et al. "Twice-daily compared with once-daily insulin glargine in people with Type 1 diabetes using meal-time insulin aspart." 2006 Diabetes UK, Diabetic Medicine, 23, 879-886.

Ashwell et al., "Optimal timing of injection of once-daily insulin gargine in people with Type 1 diabetes using insulin lispro at meal-times" 2005 Diabetes UK, Diabetic Medicine, 23, 46-52.

(56) References Cited

OTHER PUBLICATIONS

Atherton, F. et al. "Synthesis of 2(R)-A3(S)-Acylamino-2-OXO-1-Azetidinyloxy U-Acetic Acids." Tetrahedron, vol. 10, No. 6, Jan. 1, 1984, pp. 1039-1046.
AVANDIA Product Insert, Oct. 2008.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1." Treat Endocrinol 1:117, 2002.
Drucker et al., Minireview: The glucagon-like peptides. Endocrinology, vol. 142, No. 2, pp. 521-527 (2001).
Balkan B et al. "Portal GLP-1 administration in rats augments the insulin response to glucose via neuronal mechanisms." Am J. Physiol Regulatory Integrative Comp Physiol 279:R1449, 2000.
Barnett AH et al. "An open, randomized, parallel-group study to compare the efficacy and safety profile of inhaled human insulin (Exubera) with glibenclamide as adjunctive therapy in patients with Type 2 diabetes poorly controlled on metformin." Diabetes Care 29(8):1818-1825, 2006.
Barnett et al., An open, randomized, parallel-group study to compare the efficacy and safety profile of inhaled hman insulin (Exubera) with metformin as adjunctive therapy in patients with type 2 diabetes poorly controlled on a sulfonylurea. Diabetes Care, 29(6): 1282-1287 (2006).
Barragan et al. "Changes in arterial blood pressure and heart rate induced by glucagon-like peptide-1-(7-36) amide in rats." Am J. Physiol 266 (Endocrinol Metab 29):E459, 1994.
Basu A et al. "Effects of a change in the pattern of insulin delivery on carbohydrate tolerance in diabetic and nondiabetic humans in the presence of differing degrees of insulin resistance." J Clin Invest 97:2351-2361, 1996.
Bauer et al "Assessment o beta-adrenergic receptor blockade after isamoitane, a 5-HT1-receptor active compound, in healthy volunteer", Clin. Pharmacol Ther 53:76-83 (1993).
Bauer et al., "Pharmacodynamic effects of inhaled dry powder formulations of fenterol and colforsin in asthma", Clin Pharmacol Ther 53:76-83, 1993.
Baughman R, Cassidy J, Amin N, et al. A phase I, open-label study of the effect of albuterol or fluticasone on the pharmacokinetics of inhaled Technosphere® insulin inhalation powder in healthy subjects. ADA 2010; Poster 528.
Baughman R, Cassidy J, Levy B, et al. Technosphere® insulin inhalation powder pharmacokinetics unchanged in subjects who smoke. Diabetes 2008; 57: A128.
Baughman R, Haworth P, Litwin J, et al. No cardiac effects found with therapeutic and suprtherapeutic doses of Technosphere® inhalation powder: results from a thorough QTc clinical study. ADA 2011. Poster 933-P.
Baughman, RA, Evans, SH, Boss, AH, et al. Technosphere insulin does not affect pulmonary function in a 6 month study of patients with type 2 diabetes. Diabetologia 2006;49:177-118.
Bayés M et al. "Gateways to clinical trials" Methods Find Exp Clin Pharmacol 24:431-455, 2002.
Beers et al., Section 2—Chapter 13—Diabetes Mellitus, The Merck Manual of Diagnosis and Therapy, Merck Research Laboratories, pp. 165-177 (1999).
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Belmin J et al. "Novel drug delivery systems for insulin. Clinical potential for use in the elderly." Drugs Aging 20:303-12, 2003.
Benita, Charaterization of Drug-Loaded Poly(d,l-lactide) Microspheres. J. Pharm. Sci., 73: 1721-1724 (1984).
Benito E et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Bensch et al., Absorption of intact protein molecules across the pulmonary air-tissue barrier, Science 156: 1204-1206 (1967).
Berge et al. "Pharmaceutical Salts", J. Pharmaceutical Sciences, Review Article, 66(1):1-19 (1977).
Bergenstal R, Kapsner P, Rendell M, et al., Comparative efficacy and safety of AFRESA® and a rapid-acting analog both given with glargine in subjects with T1 DM in a 52-week study ADA 2009; Poster 479.
Bergeron et al. "Macromolecular Self-Assembly of Diketopiperazine Tetrapeptides." J. Am. Chem. Soc. 116, 8479-8484, 1994.
Amodeo et al., Pain peptides. Solution structure of orphanin FQ2. FEBS Letters, vol. 473, Issue 2, pp. 157-160 (2000).
Vanderah et al., FE200041 (D-Phe-D-Phe-D-Nle-D-Arg-NH2): A peripheral efficacious k opioid agonist with unprecedented selectivity. The Journal of Pharmacology and Experimental Therapeutics, vol. 310, No. 1, pp. 326-333 (2004).
Cheatham et al. "Prandial Technosphere®/Insulin inhalation provides significantly better control of meal-related glucose excursions than prandial subcutaneous insulin." Presented at the Diabetes Technology Society meeting, Oct. 2004.
Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.
Chemical Abstracts, vol. No. 114(22), Abstract No. 214519x (1990).
Chemicaland21.com. Solvents. Dec. 12, 2008. Available from: <http://web.archive.org/web20081212035748/http://www.chemicalland21.com/info/SOLVENTS.htm.
Chow et al., Particle Engineering for Pulmonary Drug Delivery. Pharmaceutical Research, vol. 24, No. 3, pp. 411-437 (2007).
Clee et al. Nature Genetics 38:688-693, 2006.
Cobble "Initiating and Intensifying Insulin Therapy for Type 2 Diabetes: Why, When, and How." Am J Ther. Jan. 8, 2009.
Coffey et al. "Valuing heath-related quality of life in diabetes." Diabetes Care 25:2238, 2002.
Colagiuri et al., Are lower fasting plasma glucose levels at diagnosis of type 2 diabetes associated with improved outcomes? Diabetes Care, vol. 25, pp. 1410-1417 (2002).
Combettes and Kargar, C, Newly Approved and Promising Antidiabetic Agents. Therapie, , Jul.-Aug. 2007: 62 (4): 293-310.
Coors et al., Polysorbate 80 in medical products and nonimmunologic anaphylactoid reactions. Ann. Allergy Astha Immunol., 95(6): 593-599 (2005).
Costello et al., "Zinc inhibition of mitochondrial aconitase and its importance in citrate metabolism in prostate epithelial cells", Journ. Biol. Chem. 272(46):28875-28881 (1997).
Cricket TM Single-Use Inhalers [on-line]. MannKind Technologies Website, posted in 2011, [retrieved on Jul. 30, 2012]. Retrieved from the Internet. <URL:mannkindtechnologies,com/DeviceTechnology/CricketSingleUseInhalers.aspx>.
Crosby, J. "Dog Normals", <http://vetmedicine.about.com/od/diseasesconditionsfaqs/tp/TP_dogfacts.htm>, copyright 2013.
Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., Elimination of the action of glucagon-like peptide 1 causes an impairment of glucose tolerance after nutrient ingestion by healthy baboons. J. Clin. Invest., 97:133-38 (1996).
Database adisinsight, "Gucagon-like peptide-1 inhalation—MannKind Corporation", Database accession No. 2009:1048 Abstract.
Davis "Postprandial Physiology and the Pathogenesis of Type 2 Diabetes Mellitus." Insulin, vol. 3, Apr. 1, 2008, pp. 132-140.
De Heer et al. "Sulfonylurea compounds uncouple the glucose dependence of the insulinotropic effect of glucagon-like peptide-1." Diabetes 56:438, 2007.
Deacon "Therapeutic strategies based on glucagon-like peptide 1." Diabetes. Sep.;53(9):2181-9, 2004.

(56) References Cited

OTHER PUBLICATIONS

Deacon et al., "Glucagon-like peptide 1 undergoes differential tissue-specific metabolism in the anesthetized pig", Am. J. Physiol. 271 (Endocrino. Metab. 34): E458-E464, 1996.
Decode study group. "Glucose tolerance and mortality: comparison of WHO and American Diabetes Association diagnostic criteria." Lancet. Aug. 21, 1999;354(9179):617-21.
DedicatedPhase, "Preclinical Trials and Research", <http://www.dedicatedphase1.com/preclinical-research.html>, copyright 2006-2011, p. 1.
Definition of analog from http://cancerweb.ncl.ac.uk/omd/about.html, pp. 1-5. Accessed by Examiner on Jul. 7, 2005 and cited in Office Action dated Jul. 26, 2013 in U.S. Appl. No. 12/830,557.
Del Prato S "Unlocking the opportunity of tight glycemic control" Diabetes Obesity and Metabolism 7:S1-S4, 2005.
Delgado-Aros et al. "Effect of GLP-1 on gastric volume, emptying, maximum volume ingested and postprandial symptoms in humans." Am J Physiol Gastrointest Liver Physiol 282:G424, 2002.
Diabetes: Counting Carbs if You Use Insulin, WedMD, http://diabetes.webmd.com/carbohydrate-counting-for-people-who-use-insulin#m Oct. 1, 2010.
Diez et al. "Inhaled insulin—a new therapeutic option in the treatment of diabetes mellitus" Expert Opin. Pharmacother., 2003, 4, 191-200.
Dorwald, F.A. Side reactions in organic synthesis. Wiley, (2005).
Doyle et al. "Glucagon-like peptide-1." Recent Prog Horm Res. 2001;56:377-99.
Dreamboat TM Reusable Inhalers [on-line]. MannKind Technologies Website, posted in 2011, Retrieved from the Internet: <URL: mannkindtechnologies.com/Device Technology/Dream Boat Reuseable Inhalers.aspx>.
Drucker "Development of glucagon-like peptide-1-based pharmaceuticals as therapeutic agents for the treatment of diabetes." Curr Pharma Design 7:1399, 2007.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Drug Delivery, Easing the drug delivery route, Jun. 2006, Pharmaceutical & Medical Packaging News, Canon Communications.
Dungan et al., Glucagon-like peptide 1-based therapies for type 2 diabetes: a focus on exntadtide. Clinical Diabetes, 23: 56-62 (2005).
Dunn, "Zinc-ligand interactions modulate assembly and stability of the insulin hexamer", Biometals, 18(4):295-303 (2005).
Edelman "Type II Diabetes Mellitus." Adv Int Med, 43:449-500, 1998.
Edited by Fukushima, Masanori, "Arterial Sclerosis," Merck Manual 17th, Japanese Edition, NIKKEI BP Corp., p. 1659-1663, 1999.
Edwards CMB et al. "Cardiovascular and pancreatic endocrine response to glucagon-like peptide-1(7-36) amide in the conscious calf." Exp Physiol 82:709, 1997.
Edwards CMB et al. "Subcutaneous glucagon-like peptide-1(7-36) amide is insulinotropic and can cause hypoglycaemia in fasted healthy subjects." Clinical Science 96:719, 1998.
Edwards et al., Recent advances in pulmonary drug delivery using large, porous inhaled particles. Journal of Applied Physiology, pp. 379-385 (1998).
Eggers et al., Molecular confinement influences protein structure and enhances thermal protein stability. Protein Sci., 10:250-261 (2001).
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Rat gastric somatostatin and gastrin relase: interactions of exendin-4 and truncated glucagon-like peptide-1 (GLP-1) amide. Life Sci., 55(8):629-634 (1994).
Elliot et al., Parenteral absorption of insulin from the lung in diabetic children. Austr. Paediatr. J. 23: 293-297 (1987).
Elrick et al. "Plasma insulin response to oral and intravenous glucose administration." J Clin Endocr 24:1076, 1964.
Engelgau MM "Screening for type 2 diabetes." Diabetes Care 23:1563-1580, 2000.
Engwerda et al., Improved pharmackinetic and pharmacodynamic profile of rapid-acting insulin using needle-free jet injection technology. Diabetes Care, vol. 34, Aug. 2011, pp. 1804-1808.
Erlanger et al., Phosphorous pentoxide as a reagent in peptide synthesis. College of Physicians and Surgeons—Columbia Univeristy, vol. 26, pp. 2534-2536 (1960).
Exubera indications, dosage, storage, stability. Http://www.rxlist.com/cgi/generic4/exubera_ids.htm, 2008.
Heine "Unlocking the opportunity of tight glycaemic control. Promise ahead: the role of inhaled insulin in clinical practice." Diabetes, Obesity and Metabolism 7:S19, 2005.
Heinemann "Variability of Insulin Absorption and Insulin Action." Diabetes Technology & Therapeutics, vol. 4, No. 5, pp. 673-682. 2002.
Heinemann et al. "Current status of the development of inhaled insulin." Br. J. Diabetes Vasc. Dis. 4:295-301, 2004.
Heinemann L et al. "Time-action profile of inhaled insulin." Diabetic Med 14:63-72, 1997.
Heinemann, L. "Intra-individual Variability of the Metabolic Effect of Inhales Insulin Together with an Absorption Enhancer", Diabetes Care, vol. 23, No. 9, Sep. 2000, p. 1343-1347.
Heise et al. "The effect of insulin antibodies on the metabolic action of inhaled and subcutaneous insulin." Diabetes Care 28:2161, 2005.
Herbst et al., Insulin Strategies for Primary Care Providers. Clinical Diabetes, vol. 20, No. 1, pp. 11-17 (2002).
Heubner et al. "On inhalation of insulin" Klinische Wochenschrift 16:2342, 1924. (Original and English translation provided in one document).
Heyder "Particle Transport onto Human Airway Surfaces", Eur. J. Respir. Dis, Suppl. 119, 29-50 (1982).
Heyder, "Alveolar deposition of inhaled particles in humans", Am. Ind. Hyg. Assoc. J. 43(11): 864-866 (1982).
Hirsch IB "Insulin analogues." N Engl J Med 352:174-83, 2005.
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.
Hite et al. "Exhuberance over Exubera." Clin Diabetes 24(3):110-114, 2006.
Hoet et al., Review: Nanoparticles—known and unknown health risks. Journal of Nanobiotechnology, vol. 2, No. 12, (15 pages) (2004).
Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann N Y Acad Sci. Dec. 26, 1996;805:729-36.
Howard C, Ren H, Rossiter A, et al. Reduced incidence and frequency of hypoglycemia in an integrated analysis of pooled data from clinical trials of subjects with type 1 diabetes using prandial inhaled Technosphere® insulin. Diabetologia 2009; 52 (suppl 1).
Howard CP, Gnudi L, Lorber D, et al. Prandial inhaled Technosphere® insulin plus insulin glargine vs. biaspart 70/30 insulin in type 2 diabetes inadequately controlled with/without oral agents. Third International Conference on Advanced Technologies and Treatments for Diabetes. 2010; Poster 300.
Howard CP, Lorber D, Ren H, et al. Reduced incidence and frequency of hypoglycemia in pooled data from trials of type 2 diabetics using prandial inhaled Technosphere® insulin. Third International Conference on Advanced Technologies and Treatments for Diabetes 2010; Poster 304.
Howard CP, Petrucci R,Amin N, et al. Pulmonary function test remain similar in patients who received Technosphere® insulin and in patients currently receiving standard antidiabetic therapy. AACE 2010; Poster 267.
Howard CP, Ren H, Rossiter A, Boss AH. Reduced incidence and frequency of hypoglycemia in pooled data from trials of type 1

(56) References Cited

OTHER PUBLICATIONS diabetics using prandial inhaled Technosphere® insulin. Third International Conference on Advanced Technologies and Treatments for Diabetes. 2010; Poster 302.
Howard CP, Ren H, Rossiter A, et al. Reduced incidence and frequency of hypoglycemia in an integrated analysis of pooled data from clinical trials of subjects with type 1 diabetes using prandial inhaled Technosphere® insulin. AACE 2010; Poster 269.
Howard CP, Rubin RR, Peyrot. M. Patient reported outcomes in adults with type 2 diabetes using mealtime AFRESAS® (inhaled Technosphere® insulin) and basal insulin versus premixed insulin ADA 2009; Poster 551.
http://www.pmpnews.com/article/blister-packaging-materials (May 26, 2009).
Huda et al. "Gut peptides and the regulation of appetite." Obesity Reviews 7:163, 2006.
Hui et al., The short half-life of glucagon-like peptide-1 in plasma does not reflect its long-lasting beneficial effects. European Journal of Endocrinology, 146: 863-869 (2002).
Hussain et al. "State of insulin self-association does not affects its absorption from the pulmonary route." Eur. J. Pharm. Sciences 25:289-298, 2005.
Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.
Imeryuz et al. "Glucagon-like peptide-1 inhibits gastric emptying via vagal afferent-mediated central mechanisms." Am J Physiol 273 (Gastrointest Liver Physiol 36):G920, 1997.
Insulin inhalation NN 1998, Drugs R & D, 2004, pp. 46-49, Adis Data Information BV.
Insulin is a natural product from http://www.levemir.com/startingoninsulin/whatisinulin.aspx, pp. 1-3. Accessed by Examiner on Apr. 30, 2014 and in Non-Final Offfice Action dated May 22, 2014 for U.S. Appl. No. 13/797,657 and in Non-Final Office Action dated May 22, 2014 for U.S. Appl. No. 12/883,369.
International Search Report for PCT International Application No. PCT/US2010/055323 filed on Nov. 3, 2010.
Written Opinion dated Jul. 1, 2013 for International Application No. PCT/US2013/032162 filed on Mar. 15, 2013.
International Search Report dated Jun. 21, 2010 for International Application No. PCT/US2010/027038 filed on Mar. 11, 2010.
Written Opinion for International Application No. PCT/US2011/060057 filed on Nov. 9, 2011.
International Search Report dated Mar. 18, 2013 for International Application No. PCT/US2012/061749 filed on Oct. 24, 2012.
International Search Report dated Jun. 20, 2012 for International Applicaion No. PCT/US2012/031695 filed on Mar. 30, 2012.
International Search Report dated Nov. 19, 2014 for International Application No. PCT/US2014/049817 filed on Aug. 5, 2014.
International Search Report for International Application No. PCT/US2010/020448 filed on Jan. 8, 2010.
International Search Report dated Mar. 11, 2010 for International Application No. PCT/US2009/069745 filed on Dec. 29, 2009.
International Search Report dated Oct. 17, 2011 for International Application No. PCT/US2010/026271 filed on Mar. 4, 2010.
International Search Report for International Application No. PCT/US2010/038287 filed on Jun. 11, 2010.
Ishibashi, Norio et al. "Studies on Flavord Peptides. Part V. A Mechanism for Bitter Taste Sensibility in Peptides." Agricultural and Biological Chemistry, 52(3), 819-27, 1988.
Iwanij et al., Characterization of the Glucagon Receptor and its Functional Domains Using Monoclonal Antibodies. The Journal of Biological Chemistry, vol. 265, No. 34, pp. 21302-21308, 1990.
Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.
Johnson et al., Peptide turn mimetics. Biotechnology and Pharmacy, p. 366-378 (1993).
International Search Report for International Application No. PCT/US2013/050392 filed on Jul. 12, 2013.
EXUBERA package insert, p. 1, 2008.
Fadl et al., Effects of MDI spray angle on aerosol penetration efficiency through an oral airway cast. Journal of Aerosol Science, vol. 38, No. 8, pp. 853-864 (2007).
Falsone et al., The Biginelli dihydropyrimidone synthesis using polyphosphate ester as a mild and efficient cyclocondensation/dehydration reagent. Institute of Chemistry, Organic and Bioorganic Chemistry, Karl-Franzens-University, pp. 122-134 (2001).
Farr, S.J. et al., Pulmonary insulin administration using the AERx® system:physiological and physiochemical factors influencing insulin effectiveness in healthy fasting subjects. Diabetes Tech. Ther. 2:185-197, 2000.
Fehmann et al. "Cell and molecular biology of the incretin hormones glucagon-like peptide-1 and glucose-dependent insulin releasing polypeptide." Endocrine Reviews 16:390, 1995.
Ferrin et al, Pulmonary retention of ultrafine and fine particles in rats. Am. J. Repir. Cell Mol. Biol., pp. 535-542 (1992).
Festa et al., "LDL particle size in relation to insulin, proinsulin, and insulin sensitivity" Diabetes Care, 22 (10):1688-1693 (1999).
Forst et al., "Metabolic Effects of Mealtime Insulin Lispro in Comparison to Glibenclamide in Early Type 2 Diabetes", Exp. Clin. Endocrinol. Diabetes, 2003, 111, 97-103.
Fritsche et al. "Glimepiride Combined with Morning Insulin Glargine, Bedtime Neutral Protamine Hagedorm Insulin, or Bedtime Insulin Glargine in Patients with Type 2 Diabetes." American College of Physicians 2003.
Galinsky et al., A synthesis of diketopiperazine's using polyphosphoric acid. Journal of the American Pharmaceutical Association, vol. 46, No. 7, pp. 391-393 (1957).
Garber, "Premixed insulin analogues for the treatment of diabetes mellitus", Drugs, 66(1):31-49 (2006).
Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.
Garg SK, Kelly W, Freson B, et al. Treat-to-target Technosphere® insulin in patients with type 1 diabetes. ADA 2011; Abstract 941-P.
Garg SK, McGill JB, Rosenstock J, et al. Technosphere® insulin vs insulin lispro in patients with type 1 diabetes using multiple daily injections. ADA, Abstract 917-P (2011).
Gates BJ "Update on advances in alternative insulin therapy." Advances in Pharmacy 1:159-168, 2003.
Glucagon for Injection (1999) glucagon for injection (rDNA origin), pp. 1-7.
Glucagon-like peptide-1; http://en.wikipedia.org/wiki/Glucagon-like peptide-1 (accessed Apr. 24, 2015).
GLUCOPHAGE Product Insert. Jan. 2009.
GLUCOTROL Product Insert. Sep. 2006.
Gnudi L, Lorber D, Rosenstock J, et al. Basal/bolus with prandial inhaled Technosphere® insulin (TI) plus insulin glargine qd vs biaspart 70/30 insulin bid in type T2 diabetes mellitus inadequately controlled on insulin with/without oral agents. Diabetologia 2009; 52 (suppl 1).
Goke et al., Exendin-4 is a high potency agonist and truncated exendin-(9-39)-amide an antagonist at the glucagon-like peptide 1-(7-36)-amide receptor of insulin-secreting beta-cells. J. Biol. Chem. 268(26):19650-19655 (1993).
Golpon et al. "Vasorelaxant effect of glucagon-like peptide-(7-36) amide and amylin on the pulmonary circulation of the rat." Regulatory Peptides 102:81, 2001.
Gonzalez et al., Actualizacion del tratamiento farmacologico de la diabetes mellitus tipo 2. Del Sistema Nacional de Salud. Volumen 32, No. 1, pp. 3-16 (2008)—full article in Spanish with English abstract.
Gotfried M, Cassidy JP, Marino MT, et al. Lung deposition and absorption of insulin from Technosphere® insulin. Diabetologia 2009; 52 (suppl 1).
Grant et al "Both insulin sensitivity and maximal glucose elimination rate are reduced in type 2 diabetes." Presented at the American Diabetes Association 65th Scientific Sessions, Jun. 2005, abstract 2202-PO.

(56) References Cited

OTHER PUBLICATIONS

Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Grant M, Harris E, Leone-Bay A, Rousseau K. Technosphere®/insulin: Method of action. Diabetes Technology Meeting 2006; Poster.
Grant ML, Greene S, Stowell GW, et al. Mimicking endogenous peptide secretion by inhalation APS 2009; poster.
Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Greene et al., Greene's protective groups in organic synthesis. 4th ed., pp. 781-783 (2007).
Gupta et al. "Contemporary Approaches in Aerosolized Drug Delivery to the Lung." J. Controlled Research, 17:129-148,1991.
Gurrieri et al., Thermal condensation of some alpha-aminoacids with phatalic acid. Thermochimica Acta, 7 (1973) 231-239.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects and patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Haak "New developments in the treatment of type 1 diabetes mellitus." Exp Clin Endocrinol Diabetes 107:Suppl 3: S108, 1999.
Haffner et al., "Proinsulin and insulin concentrations I relation to carotid wall thickness", Strock 29:1498-1503 (1998).
Hagedorn et al. "Protamine Insulin", JAMA, 106:177-180 (1936).
Haino, Takeharu et al. "On-beads Screening of Solid-Attached Diketopiperzines for Calix[5]Arene-Based Receptor." Tetrahedron Letters, 40(20), 3889-3892, 2003.
Halozyme Press Release. Jun. 6, 2009.
Hanley et al., "Cross-sectional and prospective associations between proinsulin and cardovascular disease risk factors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.
Hassan et al. "A Randomized, Controlled Trial Comparing Twice-a-Day Insulin Glargine Mixed with Rapid-Acting Insulin Analogs Versus Standard Neutral Protamine Hagedorn (NPH) Therapy in Newly Diagnosed Type 1 Diabetes." Pediatrics, 121(3), e466-e472, 2008.
Hassan et al. "In vivo dynamic distribution of 131I-glucagon0like peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hayasaka et al. "Proliferation of type II pneumocytes and alteration in their apical surface membrane antigenicity in pulmonary sarcoidosis." Chest 116:477, 1999.
Johnson et al: RyR2 and calpain-10 delineate a novel apoptosis pathway in pancreatic islets. J Biol Chem., 279 (23):24794-802, 2004.
Johnson, Keith A., Preparation of peptide and protein powders for inhalation. Advanced Drug Delivery Reviews 1997; 26:3-15.
Jones et al., An investigation of the pulmonary absorption of insulin in the rat. Third European Congress of Biopharmaceutics and Pharmacokinetics, (1987).
Joseph et al. "Oral delivery of glucagon-like peptide-1 in a modified polymer preparation normalizes basal glycaemia in diabetic db/db mice." Diabetologia 43:1319-1328, 2000.
Joy et al. "Incretin mimetics as emerging treatments for type 2 diabetes." Annal Pharmacother 39:110, 2005.
Juntti-Berggren et al. "The antidiabetogenic effect of GLP-1 is maintained during a 7-day treatment period and improves diabetic dyslipoproteinemia in NIDDM patients." Diabetes Care 19:1200-1206, 1996.
Kanse et al. "Identification and characterization of glucagon-like peptide-1 7-36 amide-binding sites in the rat brain and lung." FEBS Letters 241:209, 1988.
Kapitza C et al. "Impact of particle size and aerosolization time on the metabolic effect of an inhaled insulin aerosol." Diabetes Tech Ther 6:119, 2004.
Kapitza et al. "Dose-response characteristics for a new pulmonary insulin formulation and inhaler." Presented at the 35th Annual Meeting of the EASD, Sep. 2000, abstract OP29 184.
Kapsner P, Bergenstal RM, Rendell M, et al. Comparative efficacy and safety of Technosphere® insulin and a rapid-acting analog both given with glargine in subjects with type 1 diabetes in a 52-week study. Diabetologia 2009; 52 (suppl 1).
Katchalski E et al. "Synthesis of lysine anhydride", J. Amer Chem Soc 68:879-880, 1946.
Katz et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Ne-(Fumaroyl)diketopiperazine of L-Lys (FDKP) Interactions." Molecular Pharmaceutics, vol. 5, No. 2, 294-315, Accepted and Received 2007, published on web 2008.
Kawai et al. "Evidence that glucagon stimulates insulin secretion through its own receptor in rats." Diabetologia 38:274, 1995.
Kawamori et al. "Does hyperinsulinemia accelerate atherosclerosis?" Department of Medicine, Juntendo University School, vol. 13, No. 12, p. 954-960, 1994.
Kelley, D. et al. "Impaired postprandial glucose utilization in non-insulin dependent diabetes mellitus." Metabolism 43:1549-1557,1994.
Kenny AJ et al. "Dipeptidyl peptidase IV, a kidney brush-border serin peptidase." Biochem J. 155:169, 1976.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between African-American and non-hispanic white adults with diabetes." Diabetes Care 29:2130, 2006.
Kitabchi, Proinsulin and C-peptide:a review. May 26, 1977 (5):547-87, http://www/ncbi.nlm.nih.gov/pubmed/403392.
Klinger et al., Insulin-micro and nanoparticles for pulmonary delivery. International Journal of Pharmaceutics, vol. 377, pp. 173-179 (2009).
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler D et al. Non-radioactive approach for measuring lung permeability: inhalation of insulin. Atemw Lungenkrkh 13:230-232, 1987. (English translation attached).
Kohler, "Aerosols for Systemic Treatment", Lung (Suppl.) 677-684 (1990).

(56) References Cited

OTHER PUBLICATIONS

Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902, 1989.
Koning et al., Relationship between inspiratory flow through simulated dry powder inhalers and peak maximal inspiratory pressure. Flow Through a Simulated DPI, Chapter 3, pp. 43-56 (2001).
Labiris et al., Pulmonary drug delivery. Part I: Physiological factors affecting therapeutic effectiveness of aerosolized medications. British Journal of Clinical Pharmacology 56: 588-599 (2003).
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kraft KS, Grant M. Preparation of macromolecule-containing drug powders for pulmonary delivery Methods in Molecular Biology 2009;480:165-174.
Kreymann B et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Krueger et al. "Toxicological profile of pulmonary drug delivery agent." Presented at the American Diabetes Association 64th Scientific Sessions, Jun. 2004, abstract 465-P.
Kwon et al. "Signaling elements involved in the metabolic regulation of mTOR by nutrients, incretins, and growth factors in islets." Diabetes 53:S225, 2004.
Lankat-Buttgereit B et al. "Molecular cloning of a cDNA encoding for the GLP-1 receptor expressed in rat lung." Exp Clin Endocrinol 102:241, 1994.
Laureano et al. "Rapid absorption and elimination of insulin from the lung following pulmonary administration of Technosphere®/Insulin: A pharmacokinetic study in a rat model." Presented at the American Diabetes Association 65th Scientific Sessions, Jun. 2005, abstract 445-P.
Leahy et al. Beta-cell dysfunction in type II diabetes mellitus. Curr Opin Endocrinol Diabetes 2:300-306, 1995.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Lee et al., "Development of an Aerosol Dosage Form Containing Insulin", J. Pharm. Sci. 65(4), 567-572 (1976).
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Leiner et al. "The pharmacokinetic profile of insulin administered by inhalation in the rat." Diabetes 53 Supplement, Jun. 2004, A111.
Leone-Bay et al. "Evaluation of novel particles as an inhalation system for GLP-1." Diabetes, Obesity and Metabolism. 11:1050-1059, 2009.
Leone-Bay A, Grant M. Technosphere® Technology: A Platform for inhaled protein therapeutics. OndrugDelivery 2006 (published online).
Leone-Bay A, Grant M. Technosphere®/insulin: mimicking endogenous insulin release. In: Rathbone M, Hadgraft J, Roberts M, et al, eds. Modified Release Drug Delivery, 2e. New York, NY: Informa Healthcare USA, Inc; 2008.
Kieffer et al. "The glucagon-like peptides." Endocrine Reviews 20:876, 1999.
Kumar et al., "A Comprehensive Review of Treprostinil Pharmacokinetics via Four Routes of Administration", Clin Pharmacokinet, 2016, vol. 55, pp. 1495-1504.
Takatsuki et al., "Acute Pulmonary Vasodilator Testing With Inhaled Treprostinil in Children With Pulmonary Arterial Hypertension", Pediatr Cardiol. Apr. 2013 ; vol. 34(4): pp. 1-12.
Aradigm, "ARD-1550 and 1500—Treprostinil for the Treatment of Pulmonary Arterial Hypertension", 2013, http://www.aradigm.com/products_1500.html, p. 1.
Cipolla et al., "Deeper Lung Pulmonary Delivery of Treprostinil is Associated with Delayed Systemic Absorption", Aradigm Corp., p. 1.
Voswinckel et al., "Favorable Effects of Inhaled Treprostinil in Severe Pulmonary Hypertension: Results From Randomized Controlled Pilot Studies", Journal of the American College of Cardiology, vol. 48, No. 8, 2006, pp. 1672-1781.
Patel et al., "In Vitro Delivery of Aerosolized Treprostinil via Modern Mechanical Ventilation", Journal of Aerosol Medicine and Pulmonary Drug Delivery, vol. 26, No. 0, 2013, pp. 1-8.
Hill et al., "Inhaled Therapies for Pulmonary Hypertension", Respiratory Care, Jun. 2015, vol. 60, No. 6, pp. 794-805.
Parker et al., "Inhaled Treprostinil Drug Delivery During Mechanical Ventilation and Spontaneous Breathing Using Two Different Nebulizers", Pediatr Crit Care Med. Jun. 2017 ; 18(6), pp. 1-16.
Poms et al.,"Inhaled Treprostinil for the Treatment of Pulmonary Arterial Hypertension", CriticalCareNurse, vol. 31, No. 6, Dec. 2011, pp. 1-12.
Gupta et al., "Inhaled treprostinil sodium for pulmonary hypertension", Expert Opinion on Orphan Drugs, 2:3, pp. 283-291 (2014).
Ferrantino et al., "Inhaled treprostinil sodium for the treatment of pulmonary arterial hypertension", Expert Opin. Pharmacother, 2011, 12(16), pp. 2583-2593.
Huckaby et al., "Inhaled treprostinil via the Tyvaso Inhalation System through a tracheostomy", BMJ Case Rep 2015. doi:10, pp. 1-3.
Channick et al., "Inhaled treprostinil: a therapeutic review", Drug Design, Development and Therapy 2012, vol. 6 pp. 19-28.
Voswinckel et al., "Metered dose inhaler delivery of treprostinil for the treatment of pulmonary hypertension", Pulmonary Pharmacology & Therapeutics, vol. 22, 2009, pp. 50-56.
Madonna et al., "Pathways and Drugs in Pulmonary ArterialHypertension—Focus on the Role of Endothelin Receptor Antagonists", Cardiovasc Drugs Ther, Jul. 7, 2015, pp. 1-11.
Sandifer et al., "Potent effects of aerosol compared with intravenous treprostinil on the pulmonary circulation", J Appl Physiol 99, Sep. 1, 2005, pp. 2363-2368.
Channick et al., "Safety and Efficacy of Inhaled Treprostinil as Add-On Therapy to Bosentan in Pulmonary Arterial Hypertension", Journal of the American College of Cardiology, vol. 48, No. 7, 2006, pp. 1433-1437.
Zeenat Safdar, "Treatment of pulmonary arterial hypertension: The role of prostacyclin and prostaglandin analogs", Respiratory Medicine (2011) 105, pp. 818-827.

* cited by examiner

FIG. 1A
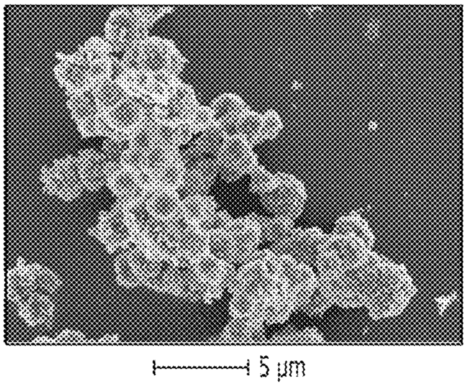
FIG. 1B
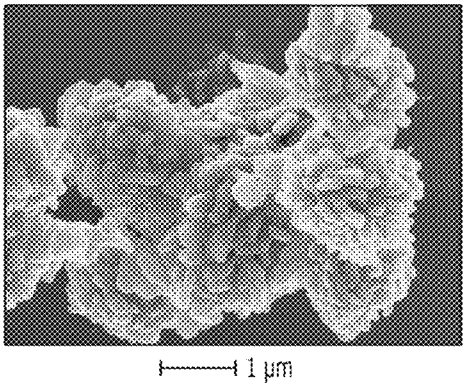
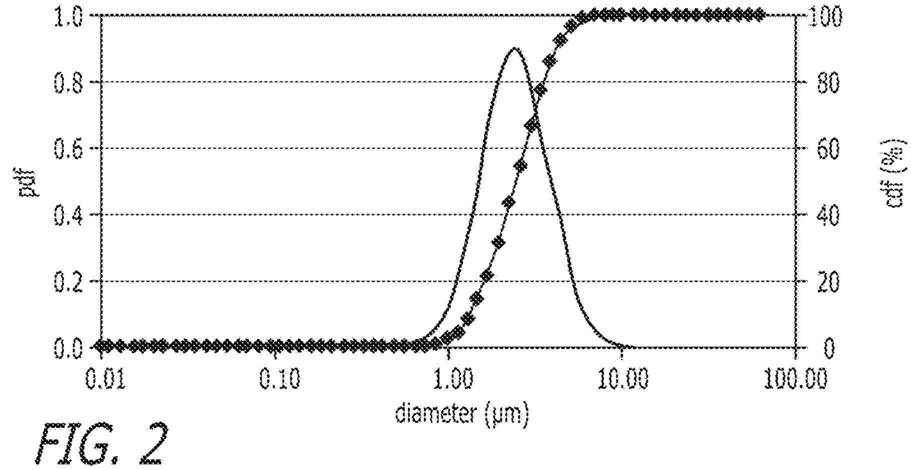
FIG. 2

FIG. 5
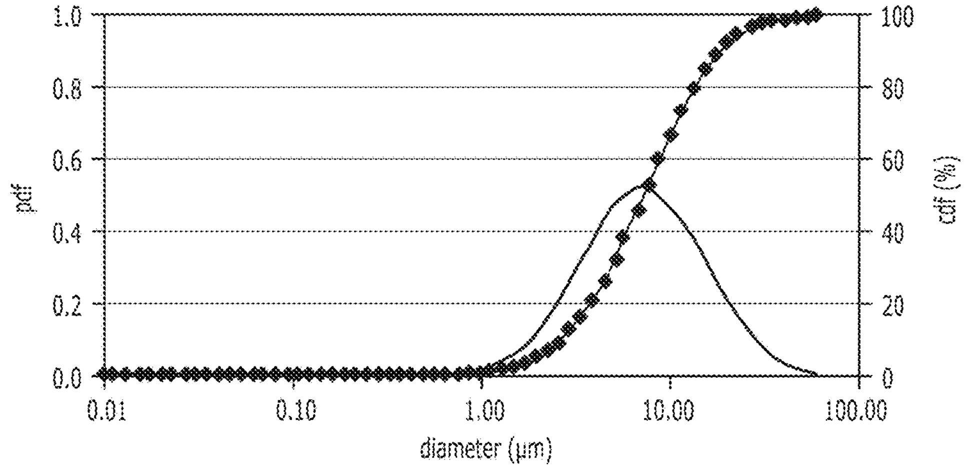
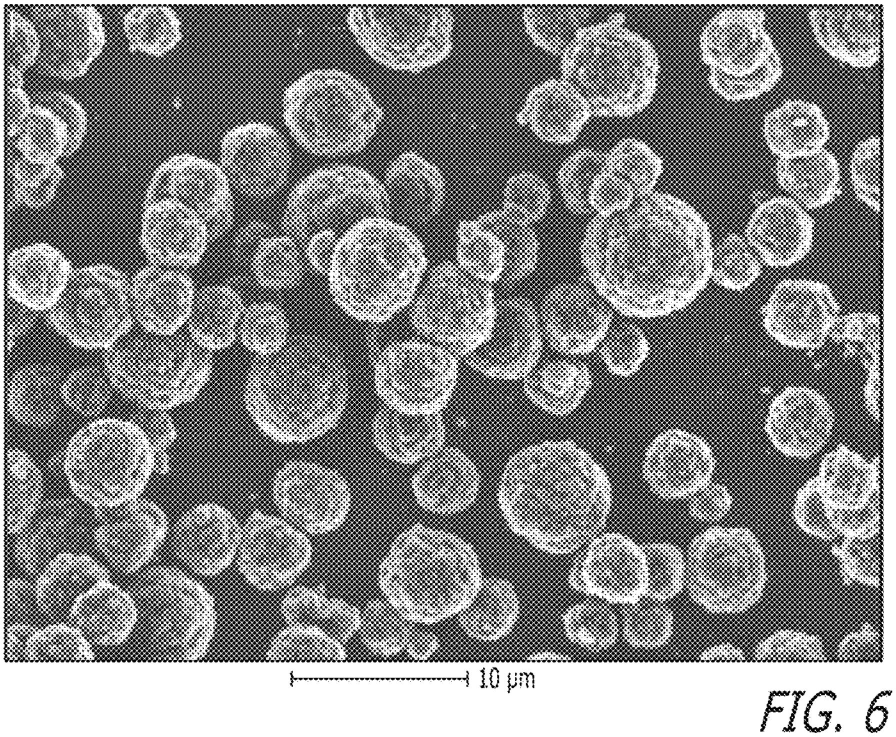
FIG. 6

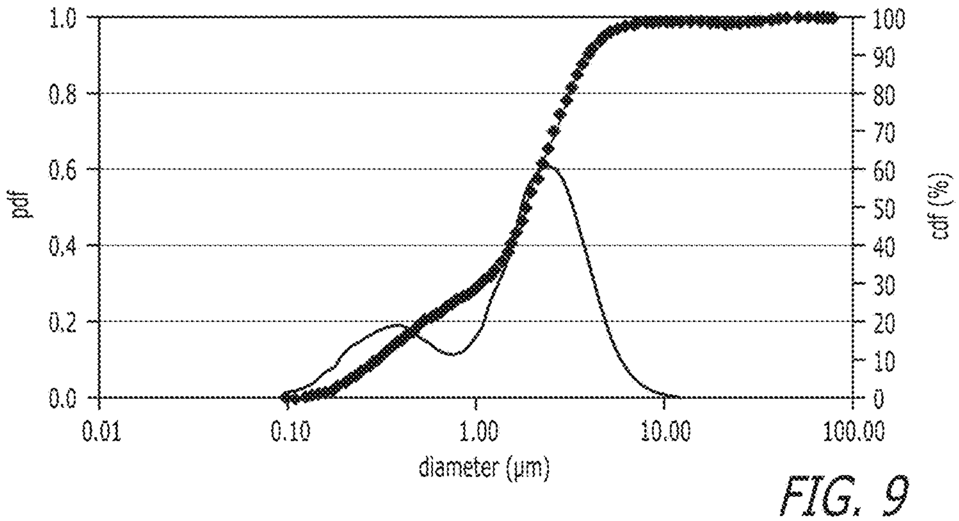
FIG. 9
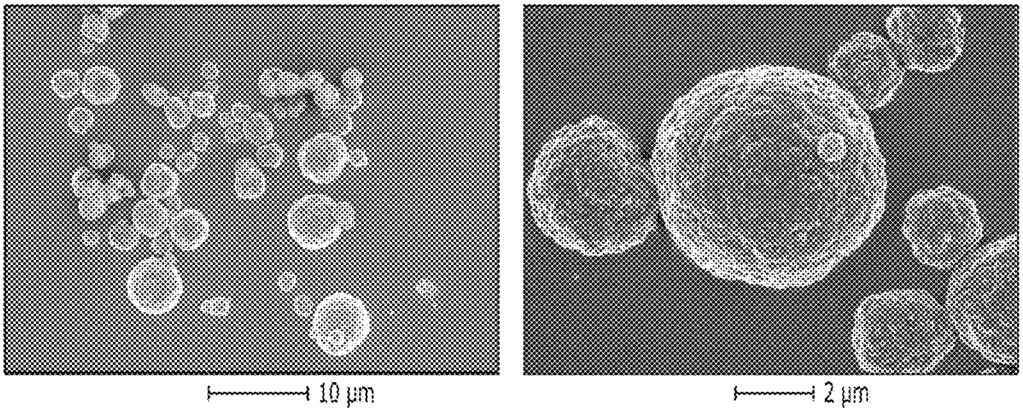
FIG. 10A
FIG. 10B

MICROCRYSTALLINE DIKETOPIPERAZINE COMPOSITIONS AND METHODS

CROSS REFERENCE TO RELATED APPLICATIONS

This application is a 371 of PCT/US2014/029491, filed Mar. 14, 2014, which claims the benefit of U.S. Provisional Patent Application Ser. No. 61/800,520, filed Mar. 15, 2013, the contents of each of which is incorporated herein by reference in its entirety.

TECHNICAL FIELD

Disclosed herein are microcrystalline diketopiperazine (DKP) particles, compositions, methods of making the particles and method of using the particles. In particular, the particles can be used as a delivery system for drugs or active agents in the treatment of disease or disorders, for example, those of endocrine origin, including diabetes and obesity.

BACKGROUND

Delivery of drugs has been a major problem for many years, particularly when the compound to be delivered is unstable under the conditions encountered in the gastrointestinal tract when administered orally to a subject, prior to reaching its targeted location. For example, it is preferable in many cases to administer drugs orally, especially in terms of ease of administration, patient compliance, and decreased cost. However, many compounds are ineffective or exhibit low or variable potency when administered orally. Presumably this is because the drugs are unstable to conditions in the digestive tract or because they are inefficiently absorbed.

Due to the problems associated with oral drug delivery, drug delivery to the lungs has been explored. For example, typically drugs delivered to the lungs are designed to have an effect on the tissue of the lungs, for example, vasodilators, surfactants, chemotherapeutic agents or vaccines for flu or other respiratory illnesses. Other drugs, including nucleotide drugs, have been delivered to the lungs because they represent a tissue particularly appropriate for treatment, for example, for genetic therapy in cystic fibrosis, where retroviral vectors expressing a defective adenosine deaminase are administered to the lungs.

Drug delivery to the lungs for agents having systemic effects can also be performed. Advantages of the lungs for delivery of systemic agents include the large surface area and the ease of uptake by the lung's mucosal surface. Pulmonary drug delivery systems present many difficulties, for example, the use of propellants, and aerosolization of biological agents such as proteins and peptides can lead to denaturation, and excessive loss of the agent to be delivered. One other problem associated with all of these forms of pulmonary drug delivery is that it is difficult to deliver drugs into the lungs due to problems in getting the drugs past all of the natural barriers, such as the cilia lining the trachea, and in trying to administer a uniform volume and weight of drug.

Accordingly, there is room for improvement in the pulmonary delivery of drugs.

SUMMARY

The present disclosure provides improved microcrystalline particles, compositions, methods of making the particles, and methods that allow for improved delivery of drugs to the lungs for treating diseases and disorders in a subject. Embodiments disclosed herein achieve improved delivery by providing crystalline diketopiperazine compositions comprising microcrystalline diketopiperazine particles having high capacity for drug adsorption yielding powders having high drug content of one or more active agents. Powders made with the present microcrystalline particles can deliver increased drug content in lesser amounts of powder dose, which can facilitate drug delivery to a patient. The powders can be made by various methods including, methods utilizing surfactant-free solutions or solutions comprising surfactants depending on the starting materials.

Certain embodiments disclosed herein can comprise powders comprising a plurality of substantially uniform, microcrystalline particles, wherein the particles have a substantially hollow spherical structure and comprise a shell which can be porous, and comprises crystallites of a diketopiperazine that do not self-assemble.

Certain embodiments disclosed herein comprises powders comprising a plurality of substantially uniform, microcrystalline particles, wherein the particles have a substantially hollow spherical structure and comprise a shell which can be porous, and comprises crystallites of a diketopiperazine that do not self-assemble, and the particles have a volumetric median geometric diameter less than 5 μm.

In a particular embodiment herein, up to about 92% of the microcrystalline particles have a volumetric median geometric diameter of≤5.8 μm. In one embodiment, the particle's shell is constructed from interlocking diketopiperazine crystals having one or more drugs adsorbed on their surfaces. In some embodiments, the particles can entrap the drug in their interior void volume and/or combinations of the drug adsorbed to the crystallites' surface and drug entrapped in the interior void volume of the spheres.

In certain embodiments, a diketopiperazine composition comprising a plurality of substantially uniformly formed, microcrystalline particles is provided, wherein the particles have a substantially hollow spherical structure and comprise a shell comprising crystallites of a diketopiperazine that do not self-assemble; wherein the particles are formed by a method comprising the step of combining diketopiperazine having a trans isomer content ranging from about 45% to 65% in a solution and a solution of acetic acid without the presence of a surfactant and concurrently homogenizing in a high shear mixer at high pressures of up to 2,000 psi to form a precipitate; washing the precipitate in suspension with deionized water; concentrating the suspension and drying the suspension in a spray drying apparatus.

The method can further comprise the steps of adding with mixing a solution comprising an active agent or an active ingredient such as a drug or bioactive agent prior to the spray drying step so that the active agent or active ingredient is adsorbed and/or entrapped on or within the particles. Particles made by this process can be in the submicron size range prior to spray-drying.

In certain embodiments, a diketopiperazine composition comprising a plurality of substantially uniformly formed, microcrystalline particles is provided, wherein the particles have a substantially hollow spherical structure and comprise a shell comprising crystallites of a diketopiperazine that do not self-assemble, and the particles have a volumetric mean geometric diameter less than equal to 5 μm; wherein the particles are formed by a method comprising the step of combining diketopiperazine in a solution and a solution of acetic acid without the presence of a surfactant and concurrently homogenizing in a high shear mixer at high pressures of up to 2,000 psi to form a precipitate; washing the precipitate in suspension with deionized water; concentrating the suspension and drying the suspension in a spray drying apparatus.

The method can further comprise the steps of adding with mixing a solution comprising an active agent or an active ingredient such as a drug or bioactive agent prior to the spray drying step so that the active agent or active ingredient is adsorbed and/or entrapped on or within the particles. Particles made by this process can be in the submicron size range prior to spray-drying.

In certain embodiments, a diketopiperazine composition comprising a plurality of substantially uniformly formed, microcrystalline particles is provided, wherein the particles have a substantially hollow spherical structure and comprise a shell comprising crystallites of a diketopiperazine that do not self-assemble, and the particles have a volumetric mean geometric diameter less than equal to 5 μm; wherein the particles are formed by a method comprising the step of combining diketopiperazine in a solution and a solution of acetic acid without the presence of a surfactant and without the presence of an active agent, and concurrently homogenizing in a high shear mixer at high pressures of up to 2,000 psi to form a precipitate; washing the precipitate in suspension with deionized water; concentrating the suspension and drying the suspension in a spray drying apparatus.

The method can further comprise the steps of adding with mixing a solution comprising an active agent or an active ingredient such as a drug or bioactive agent prior to the spray drying step so that the active agent or active ingredient is adsorbed and/or entrapped on or within the particles. Particles made by this process can be in the submicron size range prior to spray-drying.

In one embodiment, the composition can comprise microcrystalline particles comprising one or more active ingredients; wherein the active ingredients are peptides, proteins, nucleic acid molecules, small organic molecules, or combinations thereof. In embodiments wherein the active ingredient is a peptide, oligopeptide, polypeptide or protein, the peptide, oligopeptide, polypeptide or protein can be an endocrine hormone, a neurotransmitter, a vasoactive peptide, a receptor peptide, a receptor agonist or antagonist, and the like. In some embodiments, the endocrine hormone is insulin, parathyroid hormone, calcitonin, glucagon, glucagon-like peptide 1, oxyntomodulin, peptide YY, leptin, or an analog of said endocrine hormone. In embodiments, excipients can be incorporated into the particles by addition to one, another, or all feedstocks used in the spray drying step.

In one embodiment wherein the composition comprises insulin as the active ingredient, the compositions can contain insulin in amount up to, for example, 9 units or 10 units per milligram of powder to be delivered to a patient. In this embodiment, insulin can be delivered to a patient in amounts up to, for example, 100 units in a single inhalation using a dry powder inhaler. The compositions can be administered to a patient in need of insulin for the treatment of diabetes and/or hyperglycemia.

In an exemplary embodiment, the crystalline diketopiperazine composition comprises a diketopiperazine of the formula 2,5-diketo-3,6-bis(N-X-4-aminoalkyl)piperazine, wherein alkyl denotes an alkyl containing 3 to 20 carbon atoms, including propyl, butyl, pentyl, hexyl, heptyl and the like; and the formula is, for example, 2,5-diketo-3,6-bis(N-X-4-aminobutyl)piperazine, wherein X is selected from the group consisting of fumaryl, succinyl, maleyl, malonyl, and glutaryl, or a salt thereof. In a particular embodiment, the diketopiperazine is (3,6-bis(N-fumaryl-4-aminobutyl)-2,5-diketopiperazine having the formula:

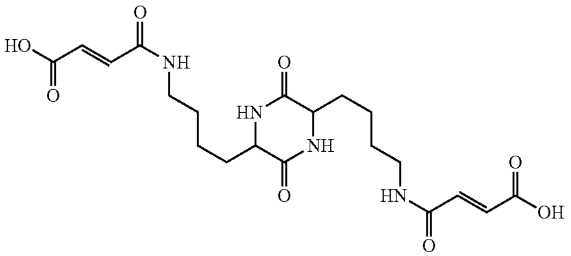 [SMILES: O=C(O)/C=C/C(=O)NCCCCC1NC(=O)C(CCCCNC(=O)/C=C/C(=O)O)NC1=O]

In various embodiments, a method of making dry powders comprising microcrystalline particles suitable for pulmonary administration is provided; wherein the method can be carried out using surfactant-free solutions, or solutions comprising a surfactant. In one aspect the diketopiperazine comprises a trans isomer content ranging from about 45% to 65%.

Certain embodiments disclosed herein include methods of producing dry powders comprising crystalline diketopiperazine microparticles from starting materials comprising free acid diketopiperazines.

Certain embodiments disclosed herein include methods of producing dry powders comprising crystalline diketopiperazine microparticles from starting materials comprising diketopiperazine salts.

In one embodiment, the method comprises:

dissolving a diketopiperazine in aqueous ammonia to form a first solution;

feeding the first solution and a second solution comprising about 10.5% acetic acid concurrently to a high shear mixer at an approximate pH of less than 6.0 under high pressure;

homogenizing the first solution and second solution to form a suspension comprising crystallites of the diketopiperazine in the suspension, wherein the suspension has a bimodal distribution of crystallites having particle sizes ranging from about 0.05 μm to about 10 μm in diameter;

atomizing the suspension under an air or gas stream; and reforming particles by spray-drying into a dry powder comprising the microcrystalline particles having substantially hollow spheres.

In another embodiment, the method comprises:

dissolving a diketopiperazine in aqueous sodium hydroxide and optionally a surfactant to form a first solution;

feeding the first solution and a second solution comprising about 10.5% acetic acid, and optionally a surfactant, concurrently to a high shear mixer at an approximate pH of less than 6.0 under high pressure;

homogenizing the first solution and second solution to form a suspension comprising crystallites of the diketopiperazine in the suspension, wherein the suspension has a bimodal distribution of crystallites having particle sizes ranging from about 0.05 μm to about 10 μm in diameter and comprising a trans isomer content ranging from about 45% to 65%;

atomizing the suspension under an air or gas stream; and reforming particles by spray-drying into a dry powder comprising the microcrystalline particles having substantially hollow spheres.

In one embodiment, the method comprises:

dissolving a diketopiperazine in aqueous ammonia to form a first solution;

feeding the first solution and a second solution comprising about 10.5% acetic acid concurrently to a high shear mixer at an approximate pH of less than 6.0 under high pressure to form a suspension comprising crystallites of the diketopiperazine in the suspension, wherein the suspension has a bimodal distribution of crystallites having particle sizes ranging from about 0.05 μm to about 10 μm in diameter;

atomizing the suspension under an air or gas stream; and reforming particles by spray-drying into a dry powder comprising the microcrystalline particles having substantially hollow spheres.

The method can further comprise the step of adding a third solution to the diketopiperazine crystallite suspension prior to atomizing the suspension; wherein the solution contains a drug or a pharmaceutically active ingredient, and the atomizing step can be performed using an external mixing 2-fluid nozzle into a spray dryer fitted with a high efficiency cyclone separator under air or gas, including nitrogen gas.

In certain embodiments, the particles in suspension have a particle size distribution as a bimodal curve as measured by laser diffraction; wherein a first peak of particles has an average particle size of about 0.2 μm to about 0.4 μm, and a second peak of particles having an average size of about 2.1 μm to about 2.4 μm in diameter.

In some embodiments, the step of atomizing the suspension uses a nitrogen stream of about 700 liters of nitrogen per hour as the process gas, and the nozzle temperature can be kept at about 25° C.

Microcrystalline particles formed by the method above do not self-assemble when suspended in a solution, such as water or other aqueous-based solvent. In a particular embodiment, the method comprises a diketopiperazine of the formula 2,5-diketo-3,6-bis(N-X-4-aminobutyl)piperazine, wherein X is selected from the group consisting of fumaryl, succinyl, maleyl, malonyl, and glutaryl. In a specific embodiment, the method comprises homogenizing in a high shear mixer a solution of a diketopiperazine, wherein the diketopiperazine is (bis-3,6-(N-fumaryl-4-aminobutyl)-2,5-diketo-diketopiperazine, or a salt thereof, including, disodium, dipotassium, magnesium, calcium, and dilithium salts.

In an embodiment, a crystalline diketopiperazine composition comprising a plurality of microcrystalline particles substantially uniform in size is obtained as a product of the spray drying step.

In an embodiment, a crystalline diketopiperazine composition comprising a plurality of microcrystalline particles with a bimodal size distribution is obtained as a product of the crystallite formation step.

When a disruption step is used, the larger species of the bimodal distribution can be shifted to smaller sizes.

Certain embodiments comprise a method of forming microcrystalline particles of a diketopiperazine acid for making dry powders carrying large drug content comprises using a salt of a diketopiperazine as a starting compound, including, 2,5-diketo-3,6-bis(N-fumaryl-4-aminobutyl)piperazine disodium salt, the method comprises:

dissolving a diketopiperazine salt in water comprising a surfactant in an amount from about 0.2% to about 6% (w/w) to form a first solution;

combining the first solution with a second solution comprising from about 8% to about 12% (w/w) acetic acid concurrently in a high shear mixer at an approximate pH of less than 6.0 under high pressure;

homogenizing the first solution and second solution to form a suspension comprising crystallites of the diketopiperazine in the suspension, wherein the suspension has a bimodal distribution of crystallites having particle sizes ranging from about 0.05 μm to about 10 μm in diameter;

atomizing the suspension under an air or gas stream; and reforming the particles by spray-drying into a dry powder comprising microcrystalline particles of the diketopiperazine acid having substantially hollow spheres.

In a specific embodiment, microcrystalline particles can be made by a process comprising, preparing a first solution comprising a diketopiperazine in water, for example, 2,5-diketo-3,6-(N-fumaryl-4-aminobutyl)piperazine disodium salt and a surfactant such as polysorbate 80; preparing a second solution comprising acetic acid at a concentration about 10.5% (w/w) and a surfactant at a concentration of about 0.5% (w/w); mixing the first solution and the second solution in a high shear mixer to form a suspension; optionally testing the suspension to determine the particle size distribution so that the suspension comprises a bimodal particle size distribution, with particles ranging in size from about 0.2 μm to about 10 μm in diameter, wherein a first peak of particles have an average diameter of about 0.4 μm and a second peak of particle have an mean diameter of about 2.4 μm, and spray-drying the suspension to obtain a dry powder.

Certain embodiments can comprise a disruption step to reduce the size of the larger-sized population in the bimodal distribution, for example utilizing sonication, stirring, or homogenization. In embodiments the disruption step can be performed prior to atomizing the suspension.

In embodiments herein, the method for making the microcrystalline diketopiperazine particles can further include a wash step using deionized water. In one embodiment, the atomizing step can be performed, for example, using an external mixing 2-fluid nozzle into a spray dryer fitted with a high efficiency cyclone separator.

The method can further comprise the step of adding a solution comprising one or more active agents to the suspension prior to dispersing and/or spray drying, wherein the active agent is a peptide, an oligopeptide, a polypeptide, a protein, a nucleic acid molecule, or a small organic molecule. The peptides can be endocrine hormones, including insulin, parathyroid hormone, calcitonin, glucagon, glucagon-like peptide 1, oxyntomodulin, peptide YY, leptin, or an analog of said endocrine hormone and the like. The method can optionally comprise the step of adding a solution comprising a surfactant, and/or a pharmaceutically acceptable carrier, including amino acids such as leucine, isoleucine, and/or monosaccharides, disaccharides, or oligosaccharides, such as lactose, trehalose, and the like, or sugar alcohols, including, mannitol, sorbitol, and the like.

In another embodiment, a composition comprising more than one active agent can be made using the present method. The method of making such composition comprises the steps of making microcrystalline diketopiperazine particles comprising more than one active agent wherein each active agent/ingredient is processed separately in a solution and added to separate suspensions of diketopiperazine particles and solution conditions are changed to promote adsorption of the active agent onto the surfaces of the crystallites, then the two or more separate suspensions comprising the active agents are blended prior to dispersing and spray-drying the particles. In a variant procedure, the blend includes a suspension containing diketopiperazine particles without active agent, for example in order to achieve a lower overall content of the active agent. In an alternate embodiment, the one or more independent solutions containing a single active agent can be combined with a single suspension comprising the diketopiperazine particles prior to dispersing and spray-drying the particles. The resultant dry powder comprises a composition comprising two or more active ingredients. In these embodiments, the amount of each ingredient in the composition can be controlled depending on the need of the patient population to be treated.

In another embodiment, the dry powder comprises a composition comprising 2,5-diketo-3,6-bis(N-X-4-aminobutyl)piperazine, wherein X is fumaryl and the composition comprises substantially homogeneous microcrystalline particles comprising a drug; wherein the particles are substantially spherical in shape having a substantially hollow core and the crystallites form a shell of the sphere. In another embodiment, the dry powders comprise a diketopiperazine of the formula 2,5-diketo-3,6-bis(N-X-4-aminobutyl)piperazine and a drug, wherein the drug is a peptide, wherein the peptide can be of various peptide lengths, molecular sizes or masses, including; insulin, glucagon-like peptide-1, glucagon, exendin, parathyroid hormone, calcitonin, oxyntomodulin, and the like.

Further embodiments include drug delivery systems comprising an inhaler with or without a cartridge, wherein the cartridge is a unit dose dry powder medicament container, for example, a cartridge, and a powder comprising the particles disclosed herein and an active agent. In one embodiment, the delivery system for use with the dry powders includes an inhalation system comprising a high resistance inhaler having air conduits which impart a high resistance to airflow through the conduits for deagglomerating and dispensing the powder. In one embodiment, the inhalation system has a resistance value of, for example, approximately 0.065 to about 0.200 (√kPa)/liter per minute. In certain embodiments, the dry powders can be delivered effectively by inhalation with an inhalation system wherein the peak inhalation pressure differential can range from about 2 to about 20 kPa, which can produce resultant peak flow rates of about between 7 and 70 liters per minute. In certain embodiments, the inhalation system is configured to provide a single dose by discharging powder from the inhaler as a continuous flow, or as one or more pulses of powder delivered to a patient. In some embodiments disclosed herewith, the dry powder inhaler system comprises a predetermined mass flow balance within the inhaler, wherein the inhaler conduits are designed to have varied flow distribution during an inhalation. For example, a flow balance of approximately 10% to 70% of the total flow exiting the inhaler and into the patient is delivered by one or more dispensing ports, which airflow passes through an air conduit designed with an area for containing a powder formulation, and wherein approximately 30% to 90% air flow is generated from other conduits of the inhaler during an inhalation maneuver. Moreover, bypass flow, or flow not entering and exiting the area of powder containment such as through a cartridge, can recombine with the flow exiting the powder dispensing port within the inhaler to dilute, accelerate and ultimately deagglomerate the fluidized powder prior to exiting the mouthpiece. In one embodiment, flow rates ranging from about 7 to 70 liters per minute result in greater than 75% of the container or the cartridge contents dispensed in fill masses between 1 and 50 mg. In certain embodiments, an inhalation system as described above can emit a respirable fraction/fill of a powder dose at percentages greater than 40% in a single inhalation, greater than 50%, greater than 60%, or greater than 70%.

In certain embodiments, drug delivery systems comprising inhalers can comprise inhalers particularly suited for use with the morphology of the particles comprising the dry powder, such as for example a crystalline or amorphous morphology.

In particular embodiments, an inhalation system is provided comprising a dry powder inhaler, a dry powder formulation comprising microcrystalline particles of fumaryl diketopiperazine having an FDKP trans isomer content between 45% and 65% and one or more than one active agents. In some aspects of this embodiment of the inhalation system, the dry powder formulation is provided in a unit dose cartridge. Alternatively, the dry powder formulation can be preloaded in the inhaler. In this embodiment, the structural configuration of the inhalation system allows the deagglomeration mechanism of the inhaler to produce respirable fractions greater than 50%; that is, more than half of the powder contained in the inhaler (cartridge) is emitted as particles of less than 5.8 μm. The inhalers can discharge greater than 85% of a powder medicament contained within a container during dosing. In certain embodiments, the inhalers can discharge greater than 85% of a powder medicament contained in a single inhalation. In one embodiment, the inhalers can discharge greater that 90% of the cartridge contents or container contents in less than 3 seconds at pressure differentials between 2 and 5 kPa with fill masses ranging up to 30 mg.

Embodiments disclosed herein also include methods. In one embodiment, a method of treating an endocrine-related disease or disorder comprising administering to a person in need thereof a dry powder formulation comprising FDKP microcrystalline particles comprising an FDKP that can have a trans isomer content of about 45 to about 65% and a drug suitable to treat said disease or disorder wherein the microparticles are produced by the present methods. One embodiment includes a method of treating an insulin-related disorder comprising administering a dry powder comprising microcrystalline particles of FDKP described above to a person in need thereof. The method comprises administering to a subject a dry powder formulation comprising microcrystalline particles of fumaryl diketopiperazine having a trans isomer content ranging from about 45% to 65%, which are particles are hollow spheres and do not contain any surfactant. In various embodiments an insulin-related disorder can specifically include or exclude any or all of pre-diabetes, type 1 diabetes mellitus (honeymoon phase, post-honeymoon phase, or both), type 2 diabetes mellitus, gestational diabetes, hypoglycemia, hyperglycemia, insulin resistance, secretory dysfunction, impaired early-phase release of insulin, loss of pancreatic β-cell function, loss of pancreatic β-cells, and metabolic disorder. In one embodiment, the dry powder comprises insulin. In other embodiments, the dry powder comprises oxyntomodulin, peptide YY, leptin, oxytocin, glucagon, an exendin, GLP-1 analogs thereof or combinations thereof.

Another embodiment disclosed herein includes a method of delivering a peptide including, GLP-1, oxyntomodulin, peptide YY, oxytocin, insulin to a patient in need thereof comprising administering a dry powder comprising diketopiperazine microcrystalline particles disclosed herein to the deep lung by inhalation of the dry powder by the patient. In aspects of this embodiment, particular features of an inhaler system are specified.

BRIEF DESCRIPTION OF THE DRAWINGS

The following drawings form part of the present specification and are included to further demonstrate certain aspects of the examples disclosed herein. The disclosure may be better understood by reference to one or more of these drawings in combination with the detailed description of specific embodiments presented herein.

FIGS. 1A and 1B are a scanning electron micrographs (SEM) of fumaryl diketopiperazine particles comprising insulin and showing the solid compositions of the particles lyophilized at low (1A) and high magnification (1B).

FIG. 2 depicts a graphic representation of the particle size distribution of the particles depicted in FIGS. 1A and 1B as measured by the probability density function (pdf, left y-axis) and cumulative distribution function (cdf, right y-axis) scale.

FIG. 5 depicts a graphic representation of the lyophilized particle size distribution in suspension as depicted in FIG. 4 formed without surfactant and showing an increase in particle size as measured by the probability density function (pdf, left y-axis) scale and cumulative distribution function (cdf, right y-axis) scale.

FIG. 6 depicts an SEM (at 2500×) of a claimed embodiment showing microcrystalline particles made from surfactant-free solutions which were spray-dried.

FIG. 9 depicts a graphic representation of the bimodal particle size distribution of a suspension formed by crystallizing $Na_2$FDKP with acetic acid in the presence of surfactant.

FIGS. 10A and 10B depict two scanning electron micrographs of particles prepared by spray drying the suspension of crystals prepared from $Na_2$FDKP at 2,500× (10A) and 10,000× (10B) magnifications.

DETAILED DESCRIPTION

Figure 3:
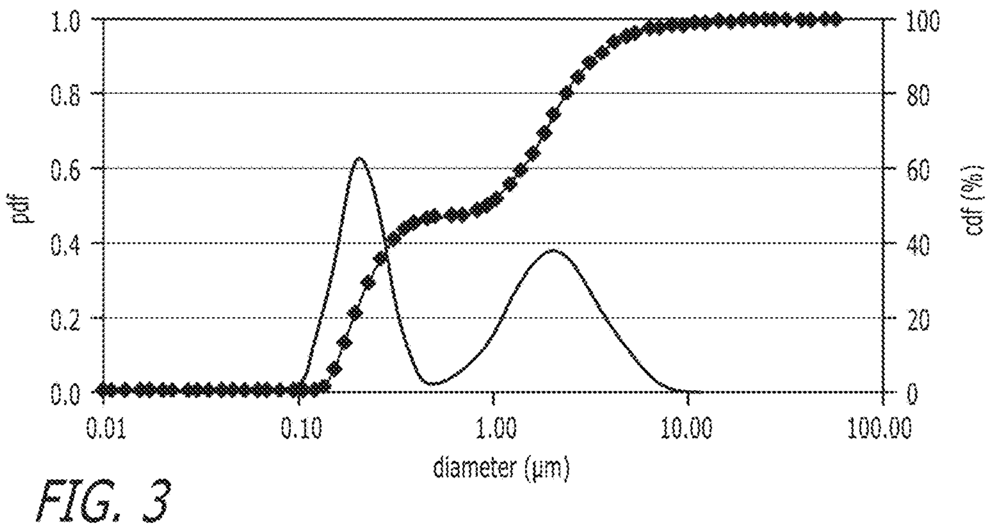
FIG. 3 depicts a graphic representation of the particle size distribution of particles obtained from an embodiment prepared from a suspension wherein the microcrystalline particles are formed without surfactant in any of the solutions used. The graph shows a typical bimodal distribution of the microcrystalline particles as measured by the probability density function (pdf, left y-axis) scale and cumulative distribution function (cdf, right y-axis) scale.

As stated, drug delivery to the lungs offers many advantages. It is difficult to deliver drugs into the lungs, however, due to problems in transporting the drugs past natural physical barriers in a uniform volume and weight of the drug. Disclosed herein are crystalline diketopiperazine compositions, dry powders and methods of making the particles. The crystalline composition and dry powder therefrom comprise diketopiperazines microcrystalline particles, which are substantially uniformly defined spheres comprising a shell comprising crystallites of the diketopiperazine and a core. In certain embodiments the core can be hollow. In one embodiment, the diketopiperazine has a defined trans isomer content which can be beneficial to the particles as drug delivery agents, methods of making the particles and methods of treatment using the particles. The particles disclosed herein have higher capacity for carrying and delivering drug content to the patient in smaller doses than standard, prior art particles.

As used herein, an "analog" includes compounds having structural similarity to another compound. Thus, compounds having structural similarity to another (a parent compound) that mimic the biological or chemical activity of the parent compound are analogs. There are no minimum or maximum numbers of elemental or functional group substitutions required to qualify a compound as an analog provided the analog is capable of mimicking, in some relevant fashion, either identically, complementarily or competitively, with the biological or chemical properties of the parent compound. In some instances an analog comprises a fragment of the parent compound either in isolation or linked to another molecule and may contain other alterations as well. Analogs of the compounds disclosed herein may have equal, lesser or greater activity than their parent compounds.

As used herein, the term "microparticle" refers to a particle with a diameter of about 0.5 to about 1000 μm, irrespective of the precise exterior or interior structure. Microparticles having a diameter of between about 0.5 and about 10 microns can reach the lungs, successfully passing most of the natural barriers. A diameter of less than about 10 microns is required to navigate the turn of the throat and a diameter of about 0.5 microns or greater is required to avoid being exhaled. To reach the deep lung (or alveolar region) where most efficient absorption is believed to occur, it is preferred to maximize the proportion of particles contained in the "respirable fraction" (RF), generally accepted to be those particles with an aerodynamic diameter of about 0.5 to about 5.7 microns, though some references use somewhat different ranges, as measured using standard techniques, for example, with an Andersen Cascade Impactor. Other impactors can be used to measure aerodynamic particle size such as the NEXT GENERATION IMPACTOR™ (NGI™, MSP Corporation), for which the respirable fraction is defined by similar aerodynamic size, for example <6.4 μm. In some embodiments, a laser diffraction apparatus is used to determine particle size, for example, the laser diffraction apparatus disclosed in U.S. patent application Ser. No. 12/727,179, filed on Mar. 18, 2010, which is incorporated herein in its entirety for its relevant teachings, wherein the volumetric median geometric diameter (VMGD) of the particles is measured to assess performance of the inhalation system. For example, in various embodiments cartridge emptying of ≥80%, 85%, or 90% and a VMGD of the emitted particles of ≤12.5 μm, ≤7.0 μm, ≤5.8 μm or ≤4.8 μm can indicate progressively better aerodynamic performance. Embodiments disclosed herein show that FDKP particles with a trans isomer content of between about 45% to about 65% exhibit characteristics beneficial to delivery of drugs to the lungs such as improved aerodynamic performance.

Respirable fraction on fill (RF/fill) represents the % of powder in a dose that is emitted from an inhaler upon discharge of the powder content filled for use as the dose, and that is suitable for respiration, i.e., the percent of particles from the filled dose that are emitted with sizes suitable for pulmonary delivery, which is a measure of particle aerodynamic performance. As described herein, a RF/fill value of 40% or greater than 40% reflects acceptable aerodynamic performance characteristics. In certain embodiments disclosed herein, the respirable fraction on fill can be greater than 50%. In an exemplary embodiment, a respirable fraction on fill can be up to about 80%, wherein about 80% of the fill is emitted with particle sizes <5.8 μm as measured using standard techniques.

As used herein, the term "dry powder" refers to a fine particulate composition that is not suspended or dissolved in a propellant, carrier, or other liquid. It is not meant to necessarily imply a complete absence of all water molecules.

Specific RF/fill values can depend on the inhaler used to deliver the powder. Powders generally tend to agglomerate and certain crystalline DKP particles form particularly cohesive powders. One of the functions of a dry powder inhaler is to deagglomerate the powder so that the resultant particles comprise a respirable fraction suitable for delivering a dose by inhalation. However, deagglomeration of cohesive powders is typically incomplete so that the particle size distribution seen when measuring the respirable fraction as delivered by an inhaler will not match the size distribution of the primary particles, that is, the profile will be shifted toward larger particles. Inhaler designs vary in their efficiency of deagglomeration and thus the absolute value of RF/fill observed using different designs will also vary. However, optimal RF/fill as a function of isomeric content will be the same from inhaler to inhaler.

As used herein, the term "about" is used to indicate that a value includes the standard deviation of the measurement for the device or method being employed to determine the value.

As used herein, the term "surfactant-free" is used to indicate that no surfactant was present in any of the reagents, including, solutions, and/or suspensions used in the process of making the microcrystalline particles.

As used herein, the term "crystallite" is used to refer to the integral crystalline units of a diketopiperazine particle, which can have varying sizes.

As used herein, "microcrystalline particles" comprise crystallites of a diketopiperazineand have a particle size distribution of from 0.05 μm to about 100 μm, as measured by laser diffraction having particles sizes of less than 50 μm, less than 20 μm, or less than 10 μm in diameter. In an embodiment the crystallites can range in size from 0.01 to 1 μm.

Diketopiperazines

One class of drug delivery agents that has been used to overcome problems in the pharmaceutical arts such as drug instability and/or poor absorption are the 2,5-diketopiperazines. 2,5-Diketopiperazines are represented by the compound of the general Formula 1 as shown below wherein $E_1$ and $E_2$ are independently N or more particularly NH. In other embodiments, $E_1$ and/or $E_2$ are independently an oxygen or a nitrogen so that wherein either one of the substituents for $E_1$ and $E_2$ is an oxygen and the other is a nitrogen the formula yields the substitution analog diketomorpholine, or when both $E_1$ and $E_2$ are oxygen the formula yields the substitution analog diketodioxane.

Formula 1

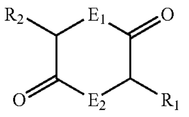

These 2,5-diketopiperazines have been shown to be useful in drug delivery, particularly those bearing acidic $R_1$ and $R_2$ groups as described in, for example, U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and 6,331,318 entitled "Carbon-Substituted Diketopiperazine Delivery System," each of which is incorporated herein by reference in its entirety for all that it teaches regarding diketopiperazines and diketopiperazine-mediated drug delivery. Diketopiperazines can be formed into microparticles that incorporate a drug or microparticles onto which a drug can be adsorbed. The combination of a drug and a diketopiperazine can impart improved drug stability and/or absorption characteristics. These microparticles can be administered by various routes of administration. As dry powders the microparticles can be delivered by inhalation to specific areas of the respiratory system, including the lungs.

Such prior art microparticles are typically obtained by pH-based precipitation of the free acid (or base) resulting in self-assembled microparticles comprised of aggregated crystalline plates with a roseate morphology. The stability of the particle can be enhanced by small amounts of a surfactant, such as polysorbate-80, in the DKP solution from which the particles are precipitated (see for example U.S. Pat. No. 7,799,344, entitled "Method of drug formulation based on increasing the affinity of crystalline microparticle surfaces for active agents" which is incorporated herein by reference in its entirety for all that it teaches regarding the formation and loading of DKP microparticles and dry powders thereof). Ultimately solvent can be removed to obtain a dry powder. Methods of solvent removal include lyophilization and spray drying (see for example U.S. Pat. No. 8,039,431 entitled "A method for improving the pharmaceutic properties of microparticles comprising diketopiperazine and an active agent" and U.S. Pat. No. 6,444,226 entitled "Purification and stabilization of peptide and protein pharmaceutical agents" each of which is incorporated herein by reference in its entirety for all that it teaches regarding the formation and loading of DKP microparticles and dry powders thereof). The particles disclosed herein are distinct from the prior art particles in that they are physically, and morphologically distinct entities and are made by an improved method. The present disclosure refers to FDKP to be understood as the free acid or the dissolved anion.

Other prior art particles are obtained by spray drying DKP solutions to obtain particles of the amorphous DKP salts typically with a collapsed-spherical morphology such as those disclosed in U.S. Pat. Nos. 7,820,676 and 8,278,308, entitled "Diketopiperazine salts for drug delivery and related methods."

Methods for synthesizing diketopiperazines are described in, for example, Katchalski, et al., J. Amer. Chem. Soc. 68, 879-880 (1946) and Kopple, et al., J. Org. Chem. 33(2), 862-864 (1968), the teachings of which are incorporated herein by reference in their entirety. 2,5-Diketo-3,6-di(aminobutyl)piperazine (Katchalski et al. refer to this as lysine anhydride) can also be prepared via cyclodimerization of N-ε-P-L-lysine in molten phenol, similar to the Kopple method, followed by removal of the blocking (P)-groups with an appropriate reagent and conditions. For example, CBz-protecting groups can be removed using 4.3 M HBr in acetic acid. This route uses a commercially available starting material, it involves reaction conditions that are reported to preserve stereochemistry of the starting materials in the product and all steps can be easily scaled up for manufacture. Methods for synthesizing diketopiperazines are also described in U.S. Pat. No. 7,709,639, entitled, “Catalysis of Diketopiperazine Synthesis,” which is also incorporated by reference herein for its teachings regarding the same.

Fumaryl diketopiperazine (bis-3,6-(N-fumaryl-4-aminobutyl)-2,5-diketo-diketopiperazine; FDKP) is one preferred diketopiperazine for pulmonary applications:

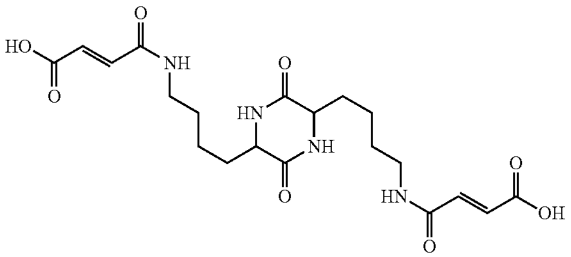 [SMILES: O=C(O)/C=C/C(=O)NCCCCC1NC(=O)C(CCCCNC(=O)/C=C/C(=O)O)NC1=O]

FDKP provides a beneficial microparticle matrix because it has low solubility in acid but is readily soluble at neutral or basic pH. These properties allow FDKP to crystallize and the crystals to self-assemble into microparticles under acidic conditions. The particles dissolve readily under physiological conditions where the pH is neutral. As noted, microparticles having a diameter of between about 0.5 and about 10 μm can reach the lungs, successfully passing most of the natural barriers. Particles in this size range can be readily prepared from FDKP.

FDKP possesses two asymmetric centers in the diketopiperazine ring. FDKP is manufactured as a mixture of geometric isomers that are identified as “cis-FDKP” and “trans-FDKP” according to the arrangement of side chains relative to the central “ring” of the diketopiperazine. The R,R and S,S enantiomers have the propenyl(amidobutyl) “side arms” projecting from the same planar side of the diketopiperazine ring (A and B below) and are thus referred to as the cis isomers while the R,S compound has the “side arms” projecting from opposite planar sides of the diketopiperazine ring (C below) and is referred to as the trans isomer.

A

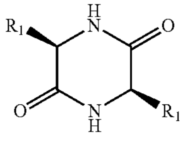

-continued

B

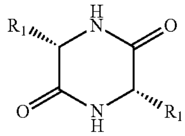

C

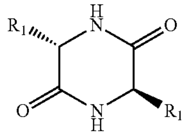

FDKP microparticle powders with acceptable aerodynamic performance, as measured by RF/fill with moderately efficient inhalers such as the MEDTONE® inhaler disclosed in U.S. Pat. No. 7,464,706 entitled, “Unit Dose Cartridge and Dry Powder Inhaler,” which is incorporated by reference herein for its teachings regarding the same, have been produced from FDKP with a trans isomer content ranging from about 45 to about 65%. Particles with isomer content in this range also perform well with high efficiency inhalers such as those disclosed in U.S. Pat. No. 8,499,757 entitled, “A Dry Powder Inhaler and System for Drug Delivery,” filed on Jun. 12, 2009, U.S. Pat. No. 8,424,518 entitled “Dry Powder Inhaler and System for Drug Delivery,” filed on Jun. 12, 2009, U.S. patent application Ser. No. 13/941,365 entitled “Dry Powder Drug Delivery System and Methods,” filed Jul. 12, 2013, and U.S. patent application Ser. No. 12/717,884, entitled, “Improved Dry Powder Drug Delivery System,” filed on Mar. 4, 2010, which disclosures are herein incorporated by reference for their teachings regarding the same. Powders comprising microparticles containing more than 65% trans-FDKP tend to have lower and more variable RF/fill. Trans isomer-enriched microparticles of FDKP have altered morphology and also lead to viscous suspensions which are difficult to process.

Formulations of FDKP microparticles having a trans isomer content of about 45% to about 65% provide powders with acceptable aerodynamic properties as disclosed in U.S. Pat. No. 8,227,409, which disclosures are incorporated herein by reference for its teachings regarding the same. Formulations of FDKP particles having a defined specific surface area less than 67 $m^2/g$ also provide dry powders for inhalation with acceptable aerodynamic properties as disclosed in U.S. Pat. No. 8,551,528 entitled “Diketopiperazine Microparticles with Defined Specific Surface Areas” filed Jun. 11, 2010, which disclosure is incorporated herein by reference for its teachings regarding the same. These FDKP powders, however, tend to be cohesive and the inhaler is designed to overcome this characteristic.

It is thus desirable to produce diketopiperazine powders having a particle composition which is less cohesive, which would allow more effective drug delivery and less inhaler design around. The present disclosure ascertains that the present method of making microcrystalline particles of diketopiperazine as exemplified by FDKP and FDKP disodium salt provides microcrystalline dry powders with acceptable aerodynamic performance which powders are less cohesive, differ in density, have an alternate physical structure that does not self assemble in suspension and provide increased capacity for drug content, including delivering one or more active agents, which was not anticipated.

It was determined that improved consistency in homogeneity of the particles could be obtained with a different process for making the diketopiperazine microparticles. The present methods for making the compositions, and compositions comprising the present microcrystalline diketopiperazine particles provide dry powders for pulmonary inhalation with beneficial physical and morphological aerodynamic characteristics.

Selection and Incorporation of Active Agents

In exemplary embodiments comprising FDKP, at least as long as the microcrystalline particles described herein retain the above isomer content, they can adopt other additional characteristics beneficial for delivery to the lung and/or drug adsorption. U.S. Pat. No. 6,428,771 entitled "Method for Drug Delivery to the Pulmonary System" describes DKP particle delivery to the lung and is incorporated by reference herein for its teachings regarding the same. U.S. Pat. No. 6,444,226, entitled, "Purification and Stabilization of Peptide and Protein Pharmaceutical Agents" describes beneficial methods for adsorbing drugs onto microparticle surfaces and is also incorporated by reference herein for its teachings regarding the same. Microparticle surface properties can be manipulated to achieve desired characteristics as described in U.S. Pat. No. 7,799,344, entitled "Method of Drug Formulation based on Increasing the Affinity of Crystalline Microparticle Surfaces for Active Agents," which is incorporated by reference herein for its teachings regarding the same. U.S. Pat. No. 7,803,404, entitled "Method of Drug Formation based on Increasing the Affinity of Active Agents for Crystalline Microparticle Surfaces" describes methods for promoting adsorption of active agents onto microparticles. U.S. Pat. No. 7,803,404 is also incorporated by reference herein for its teachings regarding the same. These teachings can be applied to the adsorption of active agent to crystallites in suspension, for example, prior to spray drying.

The microcrystalline particles described herein can comprise one or more active agents. As used herein "active agent", used interchangeably with "drug", refers to pharmaceutical substances, including small molecule pharmaceuticals, biologicals and bioactive agents. Active agents can be naturally occurring, recombinant or of synthetic origin, including proteins, polypeptides, peptides, nucleic acids, organic macromolecules, synthetic organic compounds, polysaccharides and other sugars, fatty acids, and lipids, and antibodies and fragments thereof, including, but not limited to, humanized or chimeric antibodies, F(ab), $F(ab)_2$, a single-chain antibody alone or fused to other polypeptides or therapeutic or diagnostic monoclonal antibodies to cancer antigens. The active agents can fall under a variety of biological activity and classes, such as vasoactive agents, neuroactive agents including opioid agonist and antagonists, hormones, anticoagulants, immunomodulating agents, cytotoxic agents, antibiotics, antiviral agents, antigens, infectious agents, inflammatory mediators, hormones, cell surface receptor agonist and antagonists, and cell surface antigens. More particularly, active agents can include, in a non-limiting manner, cytokines, lipokines, enkephalins, alkynes, cyclosporins, anti-IL-8 antibodies, IL-8 antagonists including ABX-IL-8; prostaglandins including PG-12, LTB receptor blockers including LY29311, BIIL 284 and CP105696; triptans such as sumatriptan and palmitoleate, insulin and analogs thereof, growth hormone and analogs thereof, parathyroid hormone (PTH) and analogs thereof, parathyroid hormone related peptide (PTHrP), ghrelin, obestatin, enterostatin, granulocyte macrophage colony stimulating factor (GM-CSF), amylin, amylin analogs, glucagon-like peptide 1 (GLP-1), clopidogrel, PPACK (D-phenylalanyl-L-prolyl-L-arginine chloromethyl ketone), oxyntomodulin (OXM), peptide YY(3-36) (PYY), adiponectin, cholecystokinin (CCK), secretin, gastrin, glucagon, motilin, somatostatin, brain natriuretic peptide (BNP), atrial natriuretic peptide (ANP), IGF-1, growth hormone releasing factor (GHRF), integrin beta-4 precursor (ITB4) receptor antagonist, analgesics, nociceptin, nocistatin, orphanin FQ2, calcitonin, CGRP, angiotensin, substance P, neurokinin A, pancreatic polypeptide, neuropeptide Y, delta-sleep-inducing peptide and vasoactive intestinal peptide; and analogs of the active agents.

The drug content to be delivered on microcrystalline particles formed from FDKP or FDKP disodium salt can typically be greater than 0.01% (w/w). In one embodiment, the drug content to be delivered with the microcrystalline particles can be from about 0.01% (w/w) to about 75% (w/w); from about 1% to about 50% (w/w), from about 10% (w/w) to about 30% (w/w), or from about 10% to about 20% (w/w). In one embodiment, for example, if the drug is insulin, the present microparticles typically comprise approximately 10% to 45% (w/w), or from about 10% to about 20% (w/w) insulin. In certain embodiments, the drug content of the particles can vary depending on the form and size of the drug to be delivered. In an embodiment wherein GLP-1 is used as an active agent, the GLP-1 content can be up to 40% (w/w) of the powder content.

In an embodiment, a composition comprising more than one active agent can be made using the present method by adsorption, for example by binding the active agent to the crystallites before forming the dry powder.

In an embodiment, a composition comprising more than one active agent can be made using the present method by entrapping the active agent between and amongst the crystallites, for example by spray drying the material, without first adsorbing the active agent to the crystallites.

The method of making such composition can comprise the steps of making microcrystalline diketopiperazine particles comprising more than one active agents; wherein each active agent/ingredient is processed separately in a solution and added to separate suspensions of diketopiperazine particles, then the two or more separate suspensions comprising the active agents are blended prior to dispersing and spray-drying the particles.

In certain embodiments, crystallites can be mixed with a solution comprising one or more active agents.

In certain embodiments, crystallites can be mixed with a solution comprising one or more active agents wherein solution conditions are changed to promote adsorption of the active agent on to the crystallite surface.

Each of multiple active agents can be adsorbed to a separate aliquot or species of crystallites. The aliquot-adsorbed crystallites can then be mixed together and spray dried. Alternatively, an aliquot can contain no active agent so as to asjust the overall content of the active agent in the dry powder without altering the conditions used to adsorb the active agent on to the crystallites.

In an alternate embodiment, the one or more independent solutions containing a single active agent can be combined with a suspension comprising the diketopiperazine particles prior to dispersing and spray-drying to reform particles. The resultant dry powder composition comprises two or more active ingredients. In this embodiment, the amount of each ingredient can be controlled in the composition depending on the need of the patient population to be treated.

As is evident from the foregoing disclosure, microparticles of embodiments disclosed herein can take many different forms and incorporate many different drugs or active agents.

EXAMPLES

The following examples are included to demonstrate embodiments of the disclosed microcrystalline diketopiperazine particles. It should be appreciated by those of skill in the art that the techniques disclosed in the examples which follow represent techniques developed by the inventors to function well in the practice of the present disclosure, and thus can be considered to constitute preferred modes for its practice. However, those of ordinary skill in the art should, in light of the present disclosure, appreciate that many changes can be made in the specific embodiments which are disclosed and still obtain a like or similar result without departing from the scope of the invention.

Example 1

Manufacture of Standard FDKP Microparticles—A prior art manufacturing process was used to produce FDKP microparticles for comparison purposes as standard particles as disclosed in U.S. Pat. Nos. 7,799,344; 7,803,404 and 8,227,409, which disclosures are incorporated herein by reference for their teachings of the relevant subject matter. In summary, the typical FDKP particle formation process, feed solutions of FDKP and acetic acid, each containing 0.05%(w/w) polysorbate 80 (PS80), are combined in a high shear mixer. Table 1 below shows the components for the FDKP and insulin stock solutions.

TABLE 1

10.5% Acetic Acid Solution filtered through 0.2 μm membrane

| Component | wt % |
|---|---|
| DI Water | 89.00 |
| GAA | 10.50 |
| 10% Polysorbate 80 | 0.50 |

TABLE 2

2.5% FDKP Solution filtered through 0.2 μm membrane

| Component | wt % |
|---|---|
| DI Water | 95.40 |
| FDKP | 2.50 |
| $NH_4OH$ | 1.60 |
| 10% Polysorbate 80 | 0.50 |

A concentrated insulin stock solution can be prepared with 1 part insulin and 9 parts about 2% wt acetic acid. The insulin stock can be added gravimetrically to the suspension to obtain a load of about 11.4% wt. The insulin-containing suspension can be mixed at least about 15 minutes, and then titrated with about 14 to about 15 wt % aqueous ammonia to a pH of about 4.5 from an initial pH of about 3.5. The suspension can be flash-frozen in liquid nitrogen to form pellets using a cryogranulator, for example, as disclosed in U.S. Pat. No. 8,590,320, which disclosure is incorporated herein by reference in its entirety, and lyophilized to yield the bulk insulin-loaded FDKP microparticles, which form small crystals or clusters that self-assemble into FDKP particles with an open structure as seen in FIGS. 1A and 1B.

Samples of particles formed were studied to measure the size distribution of these particles in suspension and the results are shown in FIG. 2. The data in FIG. 2 show a graphic representation of the particle size distribution measurements which are plotted in logarithmic scale as the probability density function (pdf, left y-axis) and the cumulative distribution function (cdf, right y-axis). The data show that the particles in suspension have a size distribution in a single peak which ranges from about 1.0 to about 10 μm in diameter centered on or about 2 μm.

Manufacture of Microcrystalline FDKP Particles—a 2.5% (w/w) FDKP was dissolved in a basic solution of aqueous ammonia (1.6% ammonia). A 10.5% (w/w) acetic acid stock solution was added in a high shear mixer (Sonolator) at an approximate pH of 2.0 under high pressure to make the particles. Particles formed were wash in deionized water. It was found that diketopiperazine microparticles are not stable without the presence of a surfactant in the solutions, however, no surfactant was added to any of the solutions or reagents in making the particles.

In these experiments, using a dual-feed high shear mixer, equal masses of about 10.5 wt % acetic acid and about 2.5 wt % FDKP solutions at about 16° C.±about 2° C. were fed at 2000 psi through a 0.001-$in^2$ orifice to form a precipitate by homogenization. The precipitate was collected in a deionized (DI) water reservoir of about equal mass and temperature. The precipitate was concentrated and washed by tangential flow filtration with deionized water. The suspension can be finally concentrated to about less than 5% solids, for example, from about 2 to 3.5% based on the initial mass of FDKP. The concentrated suspension can be assayed for solids content by an oven drying method. For samples containing the active ingredients, i.e., insulin and/or GLP-1, a suspension of FDKP from above was used to which an insulin stock solution (insulin dissolved in 2% acetic acid was added to the suspension while mixing, then the suspension pH was titrated with ammonium hydroxide to pH 4.5±0.3. Similarly, a GLP-1 dissolved in a 2% acetic acid stock solution was added gravimetrically with stirring to an FDKP-suspension. The GLP-1 FDKP suspension was titrated to pH 4.5±0.1. Each of the insulin-FDKP suspension and GLP-1-FDKP suspension were independently dispersed using an external mixing 2-fluid nozzle into a Niro SD-Micro™ Spray Dryer fitted with a high efficiency cyclone. Nitrogen was used as the process gas (25 kg/h) and the atomization fluid (2.8 kg/hr). Samples were processed using two processing conditions in the spray dryer which are listed in Table 3.

TABLE 3

| Sample ID | inlet T (° C.) | outlet T (° C.) | atomization P (bar) | ΔT (° C.) | % solids in feed | feed rate (g/min) | inlet flow (kg/hr) | atz flow (kg/hr) | % yield |
|---|---|---|---|---|---|---|---|---|---|
| 100 | 130 | 75 | 3.0 | 55 | 3.58 | 7.13 | 25 | 2.8 | 88.4 |
| 103 | 130 | 75 | 4.0 | 55 | 3.31 | 7.39 | 25 | 2.8 | 83.9 |

For control samples, blank FDKP microcrystalline particles were manufactured identically minus the insulin or GLP-1 loading step.

FIG. 3 shows data from the experiment above wherein the feed solutions were free of surfactant. FIG. 3 is a graph illustrating the particle size distribution of a particle suspension of FDKP which exhibits a typical bimodal size distribution of the particles. The particles sizes herein range from about 0.1 to about 10 μm in diameter with one population of particles being centered at 0.2 μm in diameter and the other particle population centered at 2.1 μm in diameter.

Figure 4:
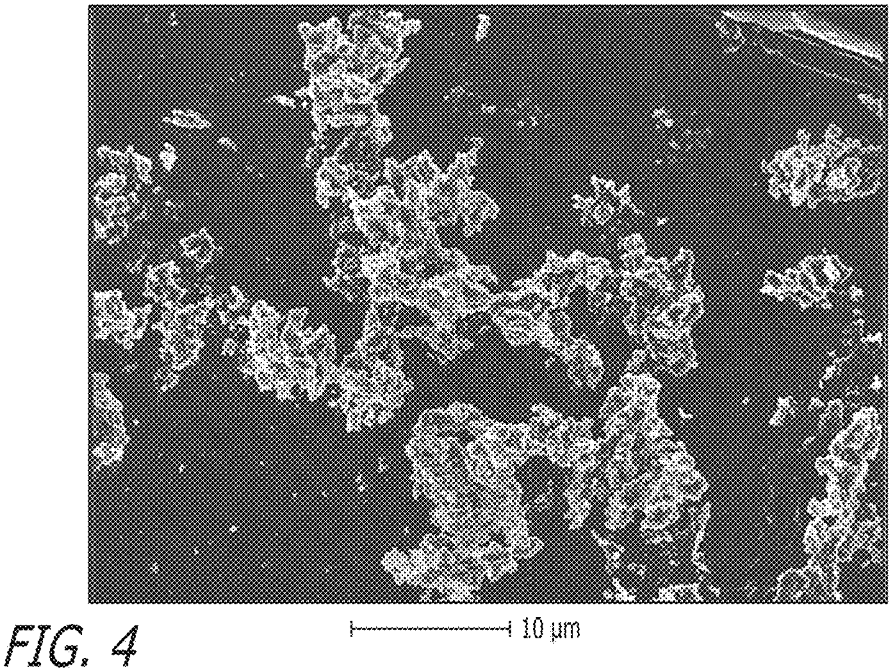
FIG. 4 depicts an SEM at low magnification (2500×) of FDKP particles recovered from an embodiment herein wherein a surfactant-free particle suspension is lyophilized.

Samples of the suspensions were lyophilized and not spray-dried. FIG. 4 is an SEM at 2,500× magnification of lyophilized particles. As seen in FIG. 4, upon lyophilization of a similar suspension, large flake-like particles were formed and gave a much larger average size when re-suspended in water as seen in FIG. 5. FIG. 5 shows the particle size distribution in suspension of a sample which was freeze-dried from particles made without the use of a surfactant. In this study, the particle size diameter of the resuspended particles increased from about 1 to about 90 μm or more.

Figure 7:
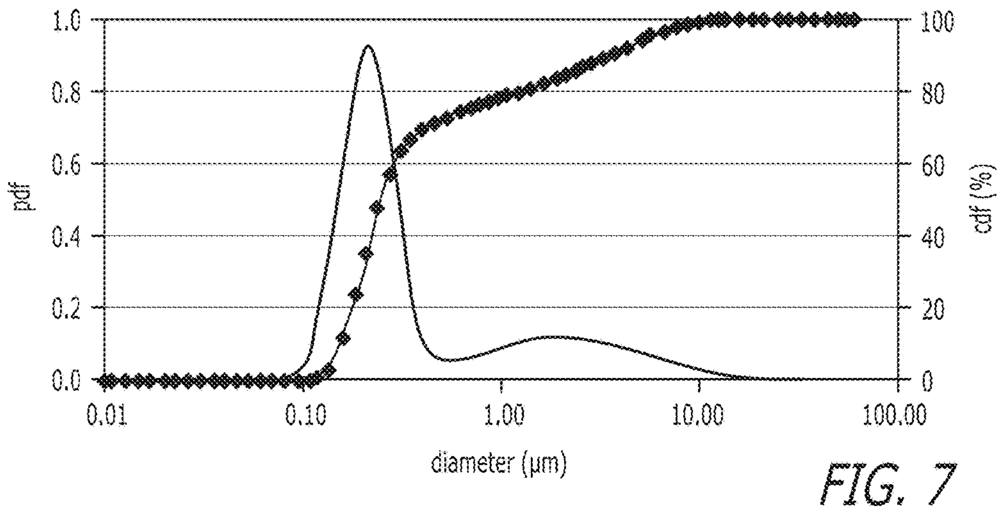
FIG. 7 depicts a graphic representation of particle size distribution of spray-dried surfactant-free particles dispersed in water.
Figure 8:
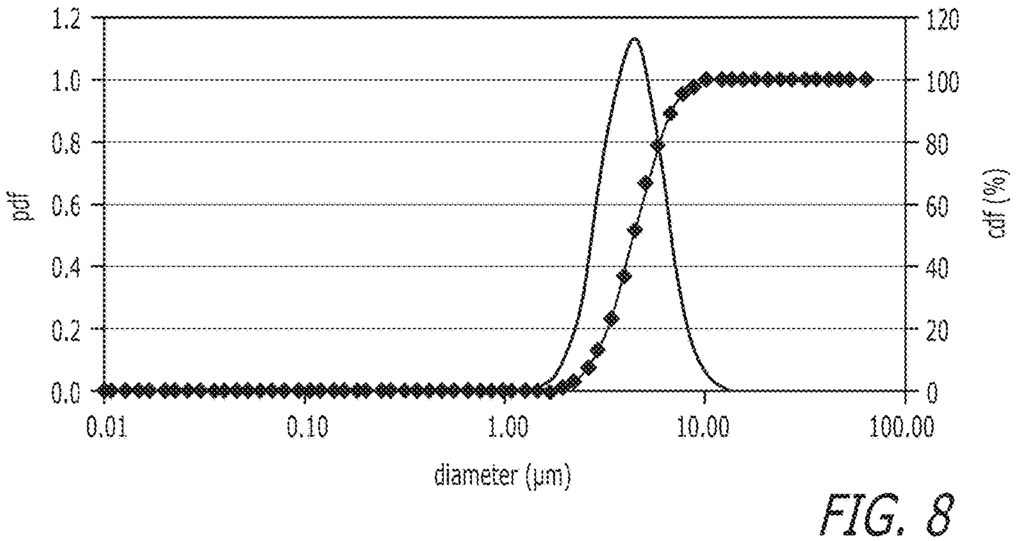
FIG. 8 depicts a graphic representation of the particle size distribution of spray-dried surfactant-free particles dispersed in 0.01 M HCl (pH 2).

FIG. 6 shows a typical 2,500× magnification of a scanning electron micrograph of powder sample from a surfactant-free preparation of microcrystalline FDKP particles which was formed using the present method and spray-dried as described above. As seen in FIG. 6 the particles are homogeneously spherical in structure comprising a shell of crystallites. When the surfactant-free suspension was spray-dried, particles with a physical diameter of approximately 4 μm were formed as shown in FIG. 6. Unlike standard FDKP particles, these particles dissociated into particles 0.2 μm in diameter when dispersed in water as shown in FIG. 7. Therefore, it is demonstrated that surfactants have a role in particle integrity. Dispersing the particles in 0.01 M hydrochloric acid inhibited particle dissociation as demonstrated in FIG. 8. It is possible that dissolved FDKP precipitates during spray drying and can be deposited along the boundaries between primary particles and can act as cement. The FDKP "cement" dissolves in water and the particles dissociate into the 0.2 μm primary particles; the lower solubility of FDKP in acid prevents dissolution and preserves particle integrity.

Example 2

Manufacture of Microcrystalline FDKP Particles by Alternate Process Using a Diketopiperazine Salt—Alternatively, crystallites of FDKP can be formed from feed solutions that contain surfactant. A feed solution of FDKP was prepared by dissolving the disodium salt of FDKP ($Na_2$FDKP) in water containing polysorbate 80 (PS80) as a surfactant without the use of ammonia as a reagent. A feed solution containing acetic acid (10.5% w/w), and PS80 (0.5% w/w) was also prepared. Mixing the two feed solutions in a DUAL FEED SONOLATOR crystallized the FDKP and yielded the bimodal particle size distribution illustrated in FIG. 9. As shown in FIG. 9, approximately 26% primary crystals formed were about 0.4 μm in diameter and about 74% of the larger particles have a diameter of about 2.4 μm. This suspension was processed and spray-dried to obtain particles and observed under SEM. The SEM micrographs were taken at 2,500× and 10,000× magnification and presented in FIGS. 10A and 10B. FIGS. 10A and 10B show that the particles are similar and spherical in shape, but smaller than those shown in FIG. 6 of Example 1, which particles were made using the FDKP as free acid. Table 4 below shows some of the physical characteristics measured for a powder made by lyophilization and a powder made by spray-drying (SD) using FDKP disodium salt.

TABLE 4

| process | % RF/fill | % CE | Bulk density g/mL | Tap density g/mL | SSA ($m^2/g$) |
|---|---|---|---|---|---|
| Lyophilized | 28.0 | 83.8 | 0.019 | 0.030 | 59.9 |
| SD | 62.8 | 88.2 | 0.159 | 0.234 | 49.6 |

The data show that the powder made from spray-dried particles exhibited higher respirable fraction (62.8 vs. 28%), higher cartridge emptying (% CE, 88.2% vs. 83.8%), and higher bulk (0.159 g/mL) and tap (0.234 g/mL) densities than the lyophilized powder (0.019 and 0.03 g/mL, respectively).

Example 3

Figure 11A:
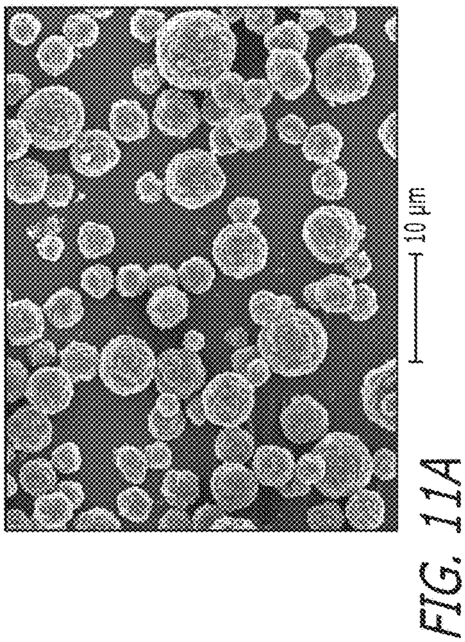
FIGS. 11A and 11B depict scanning electron micrographs of spray-dried surfactant-free FDKP particles with approximately 10 wt % insulin at 2,500× (11A) and at 5,000× (11B) magnifications.
Figure 11B:
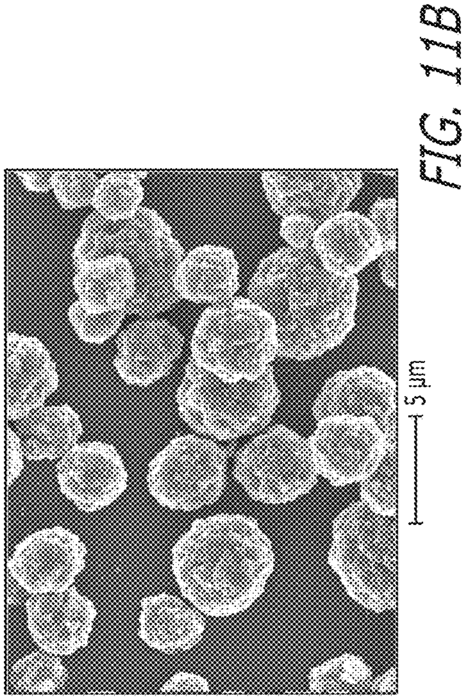

Manufacture of Microcrystalline FDKP Particles Containing an Active Agent—An active pharmaceutical ingredient (active agent) was incorporated into the particles by adding a solution of active agent to a suspension of surfactant-free FDKP crystallites and then spray drying the mixture to remove solvent as described in Example 1. Control particles (FDKP-insulin) were also made by the standard, self-assembly method using PS-80 in the solutions to make powder for pulmonary inhalation. In this study, insulin was dissolved in dilute acetic acid and added to a suspension of surfactant-free crystallites of FDKP (Samples 1 and 2 Table 5) prepared as in Example 1. The suspension was spray-dried to obtain a dry powder containing approximately 10 wt % insulin. Samples of the powders were taken for various analyses including delivery through a high resistance inhaler and scanning electron microscopy and the results are shown in Table 5. The particles were approximately the same size as the particles without insulin (Example 1) and the morphology of the particles (FIG. 11) was the same as those of FIG. 6. Moreover, both Samples 1 and 2 were less dense powder than the standard particles and Sample 1 particles have larger specific surface area (SSA) than the control. The distribution of insulin is not known, there are no obvious depositions of insulin on the particle surface to suggest the insulin is in the particle interior or incorporated into the particle wall.

TABLE 5

| Sample ID | % Insulin | % RF on Fill | % CE | SSA ($m^2/g$) | Bulk Density ($g/cm^3$) | Tapped Density ($g/cm^3$) |
|---|---|---|---|---|---|---|
| Control | 11.4 | 50 | 85 | 30-50 | 0.1 | 0.18 |
| 1 | 11.4 | 20.3 | 96.4 | 58.66 | 0.020 | 0.031 |
| 2 | 22.8 | 17.5 | 77.9 | 38.47 | 0.025 | 0.036 |

The data presented in Table 5, however, show that the surfactant-free powders behave differently from the standard particles at the same insulin content. For example, at the same insulin content the surfactant-free powder was released more effectively (96.4%) from the inhaler than the standard particle (85%). The increased in percent cartridge emptying (% CE) indicates that the powder has increased flowability. The respirable fraction (% RF on Fill) was higher for the control particles as the inhaler used to test the powders was designed for the control powders.

Example 4

Figure 12A:
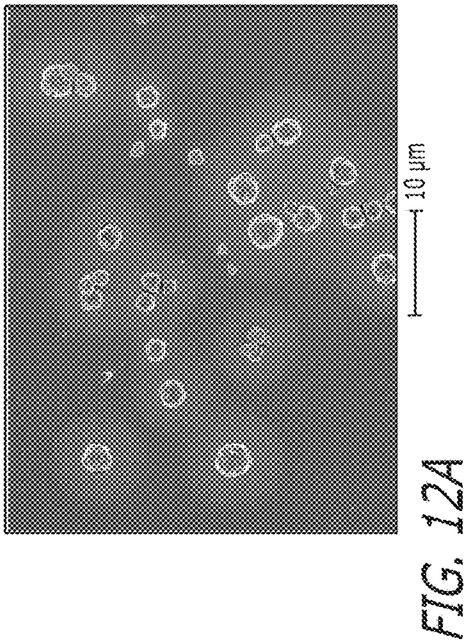
FIGS. 12A and 12B are two scanning electron micrographs of particles prepared by spray drying the suspension of crystals prepared from $Na_2$DKP at 2,500× (12A) and at 10,000× (12B) magnification.
Figure 12B:
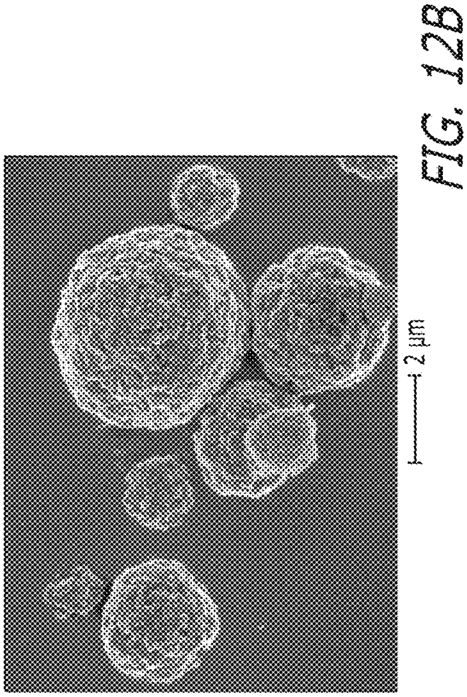
Figure 13:
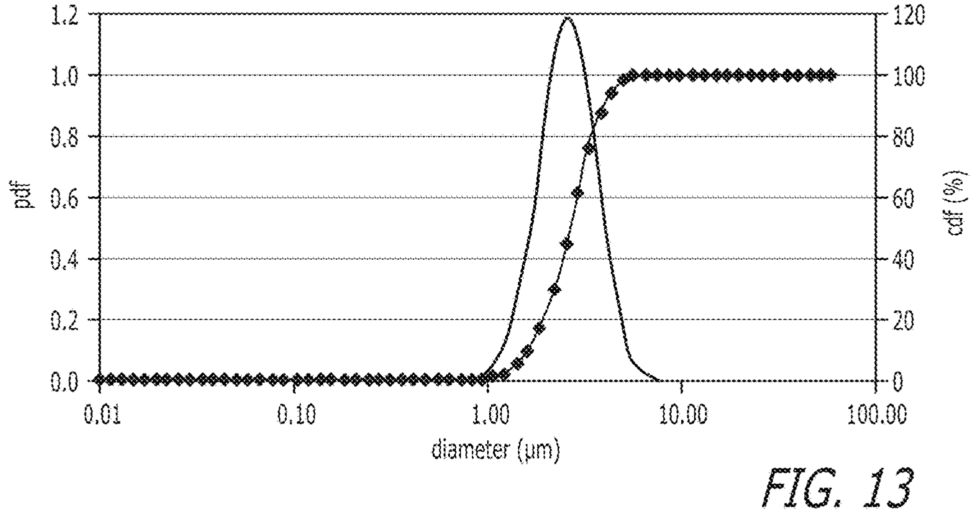
FIG. 13 depicts a graphic representation of the size distribution of particles formed by spray drying a suspension of FDKP crystallized from a solution of $Na_2$FDKP and polysorbate 80. The particles were dispersed in water for the measurement.

Manufacture of Microcrystalline FDKP Particles by Alternate Process Using a Diketopiperazine Salt—In this study, FDKP disodium salt was used to make an FDKP salt particle suspension as described in Example 2. An insulin solution was added to a suspension of surfactant-free microcrystals of FDKP prepared as in Example 2. The suspension was spray-dried to obtain a dry powder containing approximately 10 wt % insulin. The morphology of the particles formed is shown in the SEM at FIGS. 12A and 12B at 2,500× and 10,000× magnification (respectively). As seen in FIGS. 12A and 12B, the morphology was the same as the particles without insulin, showing a spherical shaped structure having a median diameter of the particles of 2.6 μm as shown in FIG. 13 and illustrated by the particles also ranging in diameter from about 1.0 μm to about 10 μm.

Example 5

Manufacture of Microcrystalline FDKP Particles Containing More than One Active Agent—In another embodiment, a composition comprising more than one active agent can be made using the present method. The method of making such composition comprises the steps as disclosed above for each individual active agent to form an active agent-FDKP suspension of each of the active agents to be incorporated into the composition. Then, the suspensions are combined and blended to form a mixture. Then the blended mixture is dispersed and spray-dried as described above to make the microcrystalline diketopiperazine particles comprising more than one active agent. In one exemplary study, insulin and GLP-1 combination powder was made.

Suspensions of FDKP crystallites prepared as in Example 1 were mixed with solutions of various active agents (e.g., ghrelin, low molecular heparin, oxyntomodulin) and spry dried to obtain particles similar in properties to those in Example 3.

Example 6

Figure 14:
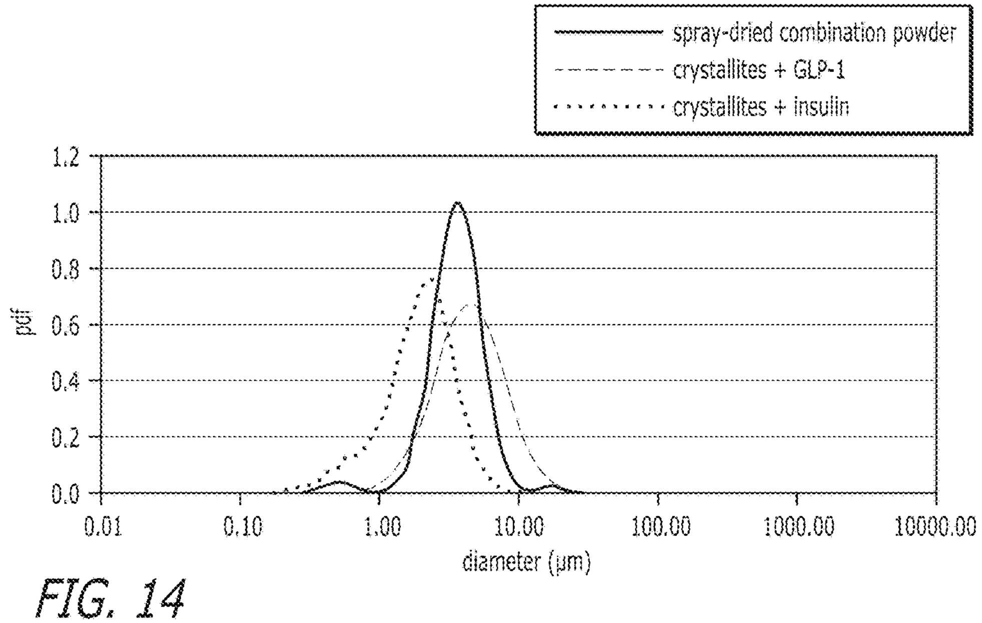
FIG. 14 depicts a graphic representation of the particle size distributions of a spray-dried combination powder and the crystallite suspension with the individual active agents. The number 1 represents the particle size distribution of the combined microcrystalline powder composition comprising two different active agents; in separate diketopiperazine-active agent particle suspension, wherein one composition contained particles of FDKP-GLP-1 and the other contained FDKP-insulin (3) in suspensions which were combined prior to being spray-dried.

Manufacture of Microcrystalline FDKP Particles Containing Two Active Agents —A combination powder with two active agents (GLP-1 and insulin) was produced by first preparing a suspension of FDKP crystallites with insulin and a second suspension of crystallites with GLP-1. The two suspensions were then mixed and the combined suspension was spray-dried to obtain a dry powder containing both active agents. The crystallite suspensions were prepared as in Example 1; after the active agents were added, the suspension was adjusted to pH 4.5 to promote adsorption onto the crystallites. FIG. 14 is a plot of data illustrating the particle size distribution of the spray-dried combination powder (1) and the crystallite suspension with the individual active agents, FDKP-insulin (2) and FDKP-GLP-1.

As seen in FIG. 14, the particle size distribution of the combination powder was centered between those of the two individual suspensions and was significantly narrower. The combination powder comprised particles having a diameter of from about 1 μm to about 10 μm. The crystallites containing the insulin were smaller (from about 0.25 μm to about 10 μm) than the GLP-1 containing crystallites which have a diameter ranging from about 0.5 μm to about 50 μm. The atomization step in spray drying probably dissociates the original clusters of crystallites in suspension and reforms the particles with a size distribution that depends on the conditions in the suspension and spray-drying conditions.

Example 7

Administration of a Dry Powder Composition Comprising Crystalline Diketopiperazine Particles to a Subject.

Dry powder formulations comprising microcrystalline diketopiperazine microparticles made with the disodium salt of FDKP ($Na_2FDKP$) were made as described in Example 1 above to contain 9 U of insulin per milligram of composition. High resistance inhalers containing a cartridge (Dreamboat™ inhaler, MannKind Corporation) were prepared containing 1 mg to 10 mg per dose were prepared to administer to subjects diagnosed with diabetes. An inhaler containing an insulin dose is provided to the patient to be treated and the patient inhales the insulin dose in a single inhalation at the start, during a meal or thereafter a meal.

Unless otherwise indicated, all numbers expressing quantities of ingredients, properties such as molecular weight, reaction conditions, and so forth used in the specification and claims are to be understood as being modified in all instances by the term “about.” Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms “a” and “an” and “the” and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. “such as”) provided herein is intended merely to better illuminate the invention and does not pose a limitation on the scope of the invention otherwise claimed. No language in the specification should be construed as indicating any non-claimed element essential to the practice of the invention.

The use of the term “or” in the claims is used to mean “and/or” unless explicitly indicated to refer to alternatives only or the alternatives are mutually exclusive, although the disclosure supports a definition that refers to only alternatives and “and/or.”

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A crystalline diketopiperazine composition comprising a plurality of microcrystalline particles comprising an active agent, said microcrystalline particles being substantially uniform in size and having a volumetric median geometric diameter less than 5 μm, and further having hollow spherical structures; each of said hollow spherical structures comprising a core and a shell, wherein said shell is porous and comprises crystallites of the diketopiperazine, said diketopiperazine having the formula:

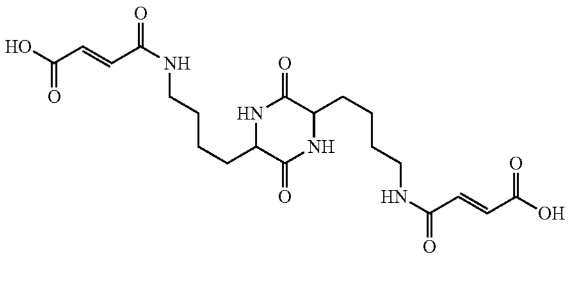 [SMILES: O=C(O)/C=C/C(=O)NCCCCC1NC(=O)C(CCCCNC(=O)/C=C/C(=O)O)NC1=O]

and a trans isomer content ranging from 45% to 65%, wherein said microcrystalline particles dissolve into crystallites when dispersed in water; wherein said microcrystalline particles are prepared in a surfactant-free solution, and said microcrystalline particles do not self-assemble in said solution, wherein the microcrystalline particles are formed by a method comprising the steps of; combining 3,6-bis(N-fumaryl-4-aminobutyl)-2,5-diketopiperazine dissolved in a solution of aqueous ammonia with a solution of acetic acid and concurrently homogenizing the solutions in a high shear mixer at high pressure of up to 2000 psi to form a precipitate; washing the precipitate in suspension with deionized water; concentrating the suspension; and drying the suspension in a spray drying apparatus.

2. The crystalline diketopiperazine composition of claim 1, wherein up to 92% of the microcrystalline particles have a volumetric median geometric diameter of <5.8 μm.

3. The crystalline diketopiperazine composition of claim 1, wherein the one or more active ingredients is a peptide, a protein, a nucleic acid molecule, or a small organic molecule.

4. The crystalline diketopiperazine composition of claim 3, wherein the peptide is an endocrine hormone.

5. The crystalline diketopiperazine composition of claim 4, wherein the endocrine hormone is insulin, parathyroid hormone, calcitonin, glucagon, glucagon-like peptide 1, oxyntomodulin, peptide YY, leptin, or an analog of said endocrine hormone.

6. A method of making microcrystalline diketopiperazine particles of claim 1 suitable for pulmonary administration as a dry powder comprising:

a) forming diketopiperazine particles in a suspension having a bimodal distribution in the particle sizes which range from about 0.05 pm to about 10 pm;

b) atomizing the suspension using a spray dryer under an air or gas stream, and c) reforming particles by spray-drying into a dry powder comprising the microcrystalline diketopiperazine particles having hollow spheres.

7. The method of claim 6 wherein a first peak of particles of the bimodal distribution in particle sizes has an average of about 0.2 pm to about 2.4 pm and a second peak of particles has an average size of about 2.1 pm to about 2.4 pm.

8. The method of claim 6, wherein the diketopiperazine is of the formula 3,6-bis(N-X-4-aminobutyl)-2,5-diketopiperazine, wherein X is selected from the group consisting of fumaryl, succinyl, maleyl, malonyl, and glutaryl.

9. The method of claim 8, wherein the diketopiperazine is 3,6-bis(N-fumaryl-4-aminobutyl)-2,5-diketopiperazine.

10. The method of claim 6, further comprising the step of adding a solution comprising one or more active agents to the suspension in step a).

11. The method of claim 6, further comprising the step of adding a surfactant to the solution or suspension.

12. The method of claim 11, wherein the surfactant is polysorbate 80.

13. The method of claim 10, wherein the one or more active agent is a peptide, a protein, a nucleic acid molecule, or a small organic molecule.

14. The method of claim 13, wherein the peptide is an endocrine hormone.

15. The method of claim 14, wherein the endocrine hormone is insulin, parathyroid hormone, calcitonin, glucagon, glucagon-like peptide 1, oxyntomodulin, peptide YY, leptin, or an analog of said endocrine hormone.

16. The crystalline diketopiperazine composition of claim 1, wherein said active agent comprises at least one of small molecule pharmaceuticals, biologicals, and bioactive agents.

17. The crystalline diketopiperazine composition of claim 1, wherein said active agent comprises at least one of proteins, polypeptides, peptides, nucleic acids, organic macromolecules, synthetic organic compounds, polysaccharides and other sugars, fatty acids, and lipids, and antibodies and fragments thereof.

18. The crystalline diketopiperazine composition of claim 1, wherein said agent comprises at least one of humanized or chimeric antibodies, F(ab), $F(ab)_2$, a single- chain antibody alone or fused to other polypeptides or therapeutic or diagnostic monoclonal antibodies to cancer antigens, vasoactive agents, neuroactive agents, hormones, anticoagulants, immunomodulating agents, cytotoxic agents, antibiotics, antiviral agents, antigens, infectious agents, inflammatory mediators, hormones, cell surface receptor agonists and antagonists, and cell surface antigens.

19. The crystalline diketopiperazine composition of claim 1, wherein said agent comprises at least one of cytokines, lipokines, enkephalins, alkynes, cyclosporins, anti-IL-8 antibodies, IL-8 antagonists including ABX-IL-8; PG-i2, LTB receptor blockers; triptans, insulin and analogs thereof, growth hormone and analogs thereof, parathyroid hormone (PTH) and analogs thereof, parathyroid hormone related peptide (PTHrP), ghrelin, obestatin, enterostatin, granulocyte macrophage colony stimulating factor (GM-CSF), amylin, amylin analogs, glucagon-like peptide 1 (GLP-1), clopidogrel, PPACK (D-phenylalanyl-L-prolyl-L-arginine chloromethyl ketone), oxyntomodulin (OXM), peptide YY(3-36) (PYY), adiponectin, cholecystokinin (CCK), secretin, gastrin, glucagon, motilin, somatostatin, brain natriuretic peptide (BNP), atrial natriuretic peptide (ANP), IGF-1, growth hormone releasing factor (GHRF), integrin beta-4 precursor (ITB4) receptor antagonist, analgesics, nociceptin, nocistatin, orphanin FQ2, calcitonin, CGRP, angiotensin, substance P, neurokinin A, pancreatic polypeptide, neuropeptide Y, delta-sleep-inducing peptide, vasoactive intestinal peptide; and analogs of the active agents.

20. The crystalline diketopiperazine composition of claim 1, wherein said agent comprises a prostaglandin.

21. The crystalline diketopiperazine composition of claim 20, wherein said prostaglandin comprises PG-I2.

* * * * *

UNITED STATES PATENT AND TRADEMARK OFFICE

CERTIFICATE OF CORRECTION

PATENT NO. : 10,421,729 B2
APPLICATION NO. : 14/774311
DATED : September 24, 2019
INVENTOR(S) : Wilson et al.

It is certified that error appears in the above-identified patent and that said Letters Patent is hereby corrected as shown below:

In the Claims

Column 24, Line 20, Claim 3 “one or more active ingredients” should be changed to --active agent--

Column 24, Line 53, Claim 10 “one or more active agents” should be changed to --the active agent--

Column 24, Lines 59-60, Claim 13 “the one or more active agent” should be changed to --the active agent--

Column 25, Line 11, Claim 18 “said agent” should be changed to --said active agent--

Column 25, Line 21, Claim 19 “said agent” should be changed to --said active agent--

Column 26, Line 20, Claim 20 “said agent” should be changed to --said active agent--

Signed and Sealed this
Third Day of December, 2019

Andrei Iancu
*Director of the United States Patent and Trademark Office*